(12) United States Patent
Kumar et al.

(10) Patent No.: US 9,198,986 B2
(45) Date of Patent: Dec. 1, 2015

(54) WDR13 AS A NOVEL BIOMARKER USEFUL FOR TREATING DIABETES AND CANCER

(75) Inventors: Satish Kumar, Hyderabad (IN); Vijay Pratap Singh, Hyderabad (IN)

(73) Assignee: Council of Scientific and Industrial Research (IN)

( * ) Notice: Subject to any disclaimer, the term of this patent is extended or adjusted under 35 U.S.C. 154(b) by 116 days.

(21) Appl. No.: 14/116,539

(22) PCT Filed: Apr. 27, 2012

(86) PCT No.: PCT/IB2012/052117
§ 371 (c)(1),
(2), (4) Date: Feb. 6, 2014

(87) PCT Pub. No.: WO2012/164413
PCT Pub. Date: Dec. 6, 2012

(65) Prior Publication Data
US 2014/0157444 A1 Jun. 5, 2014

(30) Foreign Application Priority Data

May 11, 2011 (IN) .......................... 2696/DEL/2010

(51) Int. Cl.
| | |
|---|---|
| *C12N 15/00* | (2006.01) |
| *A61K 49/00* | (2006.01) |
| *A01K 67/027* | (2006.01) |
| *C07K 14/47* | (2006.01) |

(52) U.S. Cl.
CPC .......... *A61K 49/0008* (2013.01); *A01K 67/0276* (2013.01); *C07K 14/47* (2013.01); *A01K 2217/072* (2013.01); *A01K 2227/105* (2013.01); *A01K 2267/0331* (2013.01); *A01K 2267/0362* (2013.01); *C07K 2319/41* (2013.01); *C07K 2319/43* (2013.01); *C12N 2710/10043* (2013.01)

(58) Field of Classification Search
None
See application file for complete search history.

(56) References Cited

U.S. PATENT DOCUMENTS

| | | | |
|---|---|---|---|
| 2005/0260572 A1 | 11/2005 | Kato et al. | |
| 2014/0157444 A1* | 6/2014 | Kumar | ............... A01K 67/0276 800/10 |

FOREIGN PATENT DOCUMENTS

| | | |
|---|---|---|
| WO | 2004/048938 A2 | 6/2004 |
| WO | 2010/037134 A2 | 4/2010 |

* cited by examiner

*Primary Examiner* — Michael Burkhart
(74) *Attorney, Agent, or Firm* — DLA Piper LLP (US)

(57) ABSTRACT

WD-repeat proteins are very diverse, yet these are structurally related proteins that participate in a wide range of cellular functions. WDR13, a member of this family, is conserved from fishes to humans and localizes into the nucleus. To understand the in vivo function(s) of Wdr13 gene, we have created and characterized a mutant mouse strain lacking this gene. The mutant mice had higher serum insulin levels and increased pancreatic islet mass as a result of the enhanced beta cell proliferation. While a known cell cycle inhibitor, p21, was down regulated in the mutant islets overexpression of WDR13 in the pancreatic MIN6 cell line resulted in upregulation of p21, accompanied by retardation of cell proliferation. We suggest that WDR13 is a novel negative regulator of the pancreatic beta cell proliferation. Co-immunoprecipitation experiments showed that this protein interacts with estrogen receptors and various HDACs. We provide evidence to show that WDR13 can regulate estrogen receptors-mediated transcription both in HDAC-dependent and HDAC-independent manner. Given the higher insulin levels, better glucose clearance and the lack of insulin resistance in WDR13 deficient mice, we propose that this protein may be a potential candidate drug target for ameliorating impaired glucose metabolism in diabetes.

Figure 1:
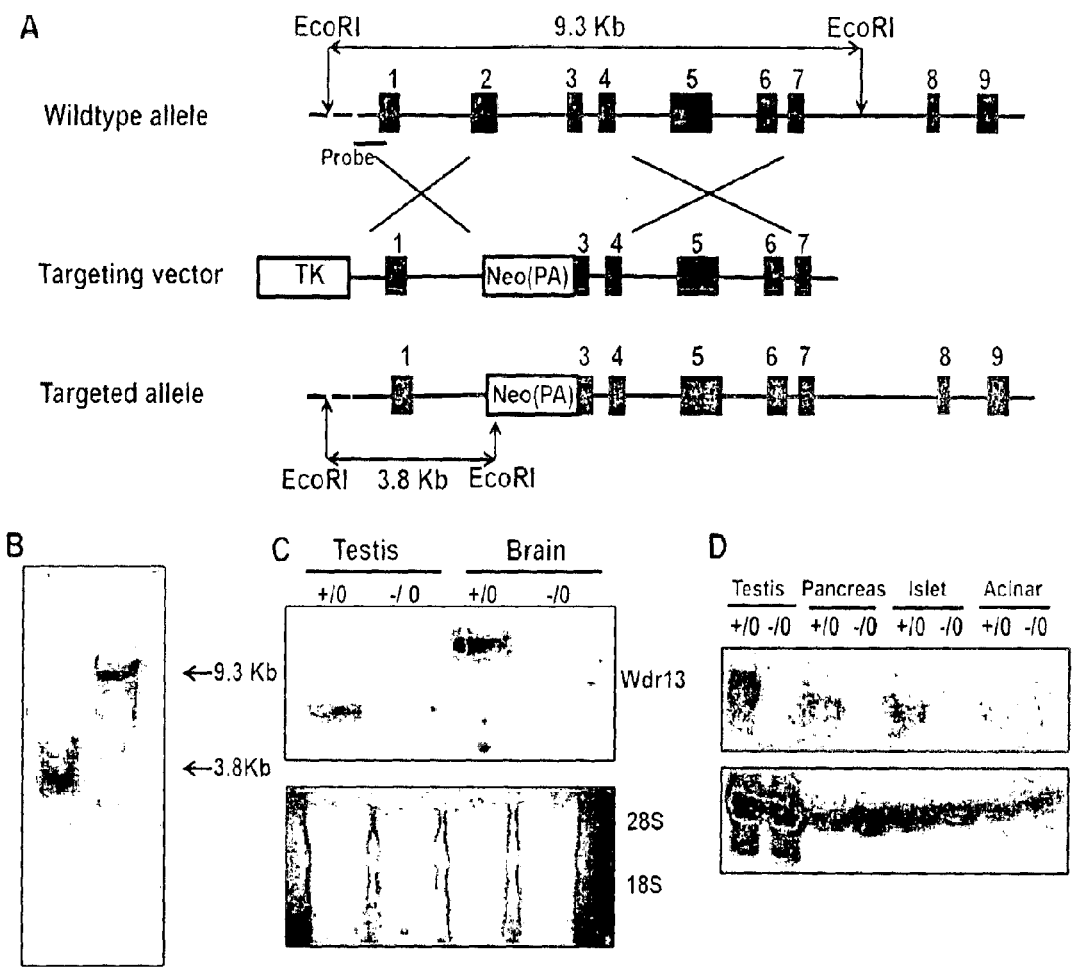

2 Claims, 11 Drawing Sheets

SEQUENCE LISTING

```
<160> NUMBER OF SEQ ID NOS: 53

<210> SEQ ID NO 1
<211> LENGTH: 11558
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Wdr13 complete gene sequence

<400> SEQUENCE: 1
ctgcagagcc atctcaccag cccccaaata cattttaaa acacattgat tatagtgttc       60
tttatgattt aaaaaaatgt gaaataaag tgtggctcac agatgtgagg gggtgctagt      120
cctctgtgct gtggactcgc atctataaag gagagactgg aaaaggaccc acaacattcc    180
tattaagatt taattggctg gatgtggtga tgaataatgt agtcctggct acttggaagg    240
```

```
ttaagacggg aggatcacaa agtctaggcc agtctggaaa atttagcaag aaagtctcaa      300
aacaaaaaac tggagcctgg tgacaagttt ttaattccag cactgggag ataaaaacag       360 aaggaagggt gagaaattca aggccactct caactgcgta tccagctgaa ggtcagcctg      420
gcctaattaa gactttgtct caaacaaaaa acaataaagg acacttgtga tgatccaata     480
cctaggcagt agagacagga ggaccagctc agttatcctc tgtaacataa tgagttggaa     540
ggcagcctgg gttacatgac acgtcgtttt taaaacaaaa ggtactggct ggcctaggat     600
gtctaaggcc ctgggtccta tcccctgtac aataagaaat tagattaatg catgcaagct    660
acttaaacag tgtccagcac tctatccgat gaatacttag ggtcttgtta aggctacatg    720
tttgtgccaa gaaataattt attcttttta agctatattg caggggatat tttaaaacac    780 tgataggtg acagaggaga taccaatagg attcacttac ctattttta ttcctcactt      840 caggcaacct aaaaagacat tatttagttg atggttagtt ttttgtcagc ttgacacaag    900
ttatggtcac ttggaaagaa ggacccttaa ctgagtctct atcagactgt cctatgggga   960
tacctgcagg ggcattttct tgcctaataa ctgttgtggg caggtgagtc tgggttgaag    1020
aagcaggcta cagcaagcct tgagaagcaa gccgataagc agtgttcctc catgatctct   1080
gcttcagttc ctggcttgat tttcagccct gagctatctc catcctgctt gcttgctttt   1140 ttttctttc tttttttgac acagggtttc tctgtatagc cctggctgtc ctggaactca    1200
ctttgtagac caggctggcc ttgaactcag aaatccgcct gcctctgcct cccaagtgct   1260
gggattaaag gcgtgcgcca ccacgcccgg cgcttgcttg ctatttaaag tatgtagtcc   1320
aggatgtagt cctggatttg actacatagg ccagactgca ttcgaactca tgatcctcct   1380
gccactctat cccctacatc accctcttct aggattacca ttatgctaga ctaaacatct   1440
tgaatttcaa ccttggaatt tctgtttttg acactgagag gaatactcaa gatacaaatt   1500
ctagcttaag gtgaatataa cagacgattg ggatactttc cttcttag gtcacagccc    1560 caaagcttgt tttcctaatt gcatattttt attaagatac tcaagtttcc tagggtaac    1620 cattcaagtc cagttagtcc cagtgaagat acacatggat tcttcccatc gcataggtgt   1680
ttagagattc atcactgcgc taggaactag agaatgttcc aggagtcagt ctctgcatat   1740
attttatttg cctggccaaa tgtgtgctgc taagaagcag cctaaaccac tttcatgaga   1800
aagtcttatt tctgatttt agctagtggt tggcacacgc attcttgtcc ttctgatcac     1860
agtacattat ccctgtgtat acaaaaggtg tcaagaggga aatgaataga actcaagggg   1920
tggagcctcg gtccttgtat gggaaactac agtcctttaa tgcgcctgcg aggctcccac   1980
gccccgggaa aggttcctat cgatttgctc tgtgctccgc agctctttct cgttgcaggc   2040
agccatcttg cctggagctt gagacaggga gaagagagag aaggaaccgg tgacactggg   2100
ctcagggtcg ccgggggggg ggggcgcctc aagagctagg ggtagcccg gaggtggtcc    2160 tggatcctga gctatgctct aggactagaa aaggaaggc ggagggcaga aggcttgatg    2220
ggtggggaat gtcaaacaag acttgctatg ggggggaggg gcgttgctac ggcaactgga   2280
gagggcgggg tcatgtctga actgctgctg tgagtcaccg gagtgctgcc caggaaaggc   2340
agggctgggg tgatgaccac gctaacgacc cagtgggatt tcgcgacatc acctgtgtgg   2400
agggacttcg tgtctatggc aactgtcacc tggtgggcgg aactagattt tctctgcctg   2460
ggacgctgac attccaagcc cttgccctgc aggctcccgc aggcagacaa accaaagaag   2520
gaagccaggg aatggccgcg gtgtggcagc aagtattagc agtggacgcg aggtgaggcg   2580
```

```
tggggttgga gcccatggga gaggaactta ctgtggtgca tgagcaatgg cgataagtgc    2640
agctgggcgg agaagttggc tggtgcggct gcgtgagcat gcgcagtagc ttggtgtggg    2700
atagtcctgc ggttaagtgg cctgggctgg agccggttct aaagagcatg ctgggaaaat    2760
gcggtttgaa atggacatgc gcagactgtc tttgagtggg tagtggaagt caggctggtg    2820
acttcctatc tagtccctca ttgcttatcc tcttccccaa cttttctcga tatcactacc    2880
ctactattat tacaattgct accccatact aacctctacc gttatctgac cctaacctcc    2940
attgttgtac attaccaatc tgacgtatgt catcatgcta gactgatatt acagctggcc    3000
cagactgacc ccaacagagc tgcaaattga ctatattgtc gctagagtga tcttttcatc    3060
ataaccacta attattgcat aattgccccc catcacaatc ccaagagaaa tcccctttg    3120
ctgctcttgt tcactcttac catcccagtc actgccaaac cttgtaccac ctcgagctga    3180
tttattccct ctgtcctgtg cctgctgcct gccctgcctc ctggacccca caggtacaac    3240
gcctaccgta caccaacgtt tccacagttt cggacccagt atatccgccg gcgcagccag    3300
ctgcttcggg agaatgccaa agctggtcac cccccagcat tgcgtcggca gtacctgagg    3360
ctacggggcc agctattggg ccaacggtac gggccactct cagaaccagg cagtgctcgt    3420
gcctatagca acagcattgt ccgcagcagc cgaacaaccc ttgatcgaat ggaggtgagc    3480
tcctagctgc accacccgcc atgtatctcc cctgcctctg tagtcaccat agttttggt    3540
caaacatcag tgatgtacaa agtactgttc caggtcagta gaggactaaa agggaataga    3600
gaagccaagt caatgaacat tgataagcag acagtgaatt agataaacac agagcaggta    3660
agactgatga gttgataatt taccatggta tagtaagcaa tgcaaagata gtaacataca    3720
acagacttaa aaagcaaaaa ggaacacaag tgtttggtgc atggatatag ttcagtaact    3780
agcgtgattg cctagtatgt atgagactga tggttctatt ctcaacatgg ccaagaagaa    3840
tgaaaagtca ctgctttgag ctaaaggagg gagctgtgct taatagggaa gacttgtctg    3900
gggagggaac accgaaacct gacagaagtg agagactgat ttgagtgctt ctctgggaag    3960
aaagtagtca tcccttgtga ggaaagcatg tatgtactaa ggatgtttgg aacaggaaag    4020
gaaggacaga aacaaaggca ctagtgaaga aactgttgaa accacacaag tgagcagtga    4080
cagtggtggc tggcgccatg tgtggtgacg agaagtcagg ccccagattt aagctcatct    4140
cagagattaa tttctatta tttatttatt tatttattat atgtaagtac actgtagctg    4200
tcctcagaca ctccagaaga gggagtcaga tctcgttaca gatggttgtg agccaccatg    4260
tggttgctgg gatttgaact cctgaccttc ggaaaagcag ttgggtgctt ttacccactg    4320
agccatctca ccagcccaat ttctcttctt tttgagacag gatctcaccc agactggcct    4380
caaattcact gtgtagccaa ggcaggcctt gagcacggtg accttcctgc ctcagtttcc    4440
caaagtgctg gaattagagg tatgcaccat ccccaaccct cttctctttg caggactttg    4500
aagatgaccc cagagccctg ggggctcgag acaccgccg atctgtcagc cgaggttcct    4560
accagctgca ggcacaaatg aaccgtgcag tctatgagga caggtacata ccagaggcag    4620
gcagggggtg gagattcacc aggaggagag gggccctggg acgtggcagt ctgaacaccc    4680
atacctacct cctatcaccc cttcccacct cctgttgggg ctcaggcctc ctggcagtgt    4740
ggtacccacg tcggtggcag aggcaagtcg ggccatggcc ggggacacgt cgctgagtga    4800
gaactatgcc tttgcaggca tgtaccatgt ttttgaccaa cacgtggatg aggcaggtga    4860
gctaatgggt ggtagggccc atcaccaaac atttgttcaa acaactaccc aaggcatcct    4920
tttctagaat gcaaggcctc tgacaccata cctcagaagg aggaaatagc actgataaaa    4980
```

```
cctttagcaa agccaagcag tgatggcgca cacctctaat tccagcactc gggaggcagg    5040
tggatttgag ttcgaggcca gcctggtcta cagagtgagt tccaggacag ccagggctac    5100
acagagaaac cctgtctcgg aaaagaaaa agaaaaaaaa aacctttagc aaatgcaaaa     5160
gccctcttgc aaagtggtcc aagaaggttt tggtaatgta ggtactggaa agagctacac    5220
aaacccaaga gagtcctttg tagcaggctg cctgagtgtt tgagtctctt agaagagttc    5280
aaaacctttg ctgatggtaa ctcccttgta gaggccacag tgggccacaa tgtgtggatg    5340
gttttgcaaa ctcctgagag cttgattatt gtaaagtact caataagaca gtacaatttt    5400
tgcattgcaa aagacttttg tagtcctcaa agtgtctgct aagatttaga gagcattttg    5460
gcagtaggcc ttctaagatt acaactgcct tgtcggcca aggaaagtcc tttgttgagg     5520
ctactgttcc ttgtgctcag tgaatgtgtt gactcccaca aatggctcct ggcatttgc     5580 agtcccaagg gtgcgcttcg ccaatgacga ccggcaccgc ctggcctgct gctccctgga    5640
cggcagcatc tccctgtgcc agctggtgcc tgccccaccc actgtgctcc atgtgctacg    5700
gggccataca cgtggcgtct cggacttcgc ctggtccctc tccaatgaca tccttgtgtc    5760
cacctccctc gatgccacca tgcgcatctg ggcctccgag gacggccgct gcatccgtga    5820
gatccctgac cctgatggcg ccgaattgct ctgctgcacc ttccagccag tcaacaacaa    5880
cctcactgtg gtcaggctcc aggacacctg ctcaccaagg gcgggcatgc tgggtctgga    5940
gggctgtcct ggggcactag agaataaggc ttaatacccc caagtcctat cccagccgtc    6000
ctgtggtcag actcaaaggg aaagagacca acgaaaagca cagtttgtgg tctggaatgg    6060
ccttgctgtg tagacttgtg tgtagactcc cgagctggga tggagggggtt gtctcctagc    6120 cctgggattc cactggtccc atccaccaca gtctcacagt tttctgtcta caggggctgc    6180
tgctatgggg caggatgatg aggctgaaag ctcatctagt ctgtcagtgg cagccccact    6240
gttgtcagac tccaggacag actggccaga gggcagagga aggacatgga aagtctggca    6300
tgacctgggg ggtagggagt tgaaatatag gggaacaaca ggccatgagt gagctagcgc    6360
ttggggctct gtctctttgt aatggtagca gctcatgggc ttcaggaggg gacagtccag    6420
ggtataaggg aaagatgtaa aggtgtcaca aggcgaggtt ttcagactca gagactaaga    6480
ctgctttggt ctcgtgagac caactattgt gggcattttg agggcacagc taaggagtag    6540
gaattgtgcc tgggtcacct tctggtatac ctggcctggt cccactgtgt taaacacaaa    6600
ggactagatg gctcagaatg atggtgtatg cctgtcaccc acaggtgggg aacgccaagc    6660
acaacgtgca tgtcatgaac atctccacag gcaagaaagt gaagggtggc tccagcaagc    6720
tcaccggccg cgtcctcgcc ctgtcctttg atgcccctgg tcggctgctc tgggcaggcg    6780
atgaccgcgg cagtgtcttc tccttttctct ttgacatggc cacaggtagg cagaccacag    6840
acttcgggtt cggtacccct ggttttcatt ctcccaggac tcagtccttg tcctccactg    6900
attcaggaaa gctgaccaaa gccaagcgac tagtagtgca tgaaggcagc cctgtaacca    6960
gcatttctgc ccggtcctgg gtcagccgtg aagcacggga cccctctctg ctcatcaatg    7020
cctgcctcaa caagctgcta ctctacaggt gggttcctcc cccagagtgg aacaagaacc    7080
tgtctctgtc acattaattt caccaaggac agaggacctc ataatatgat gaggataggg    7140
tcggagatgt aacttagtgg cagagtgctg atctagctgg tacagagctc tgtgttccat    7200
ccccagaaac acgccacata cacacacaca ctatatatct atatctatgt ctatgtctat    7260
atatttgtgt gtgtatatat atacacacat atatatacat acatatatat atatatatat    7320
```

```
atttatatag tgattcctta cctactatat atatatatac tatgcaataa tggtgatatc     7380
aatagcaaca taaataggaa tagcagtaat aagactctac atgaacattg ctatggctag     7440
gtcccattca aagcactttg tatatatcac cttatttaat cttcacaatc agtggtagag     7500
cactcgccta gcatgtataa ggctgtgggt tccactctca acattataac taaagaaaaa     7560
accaccagca cctattcctc tttccttgtt ttgaattttt cacgtgtgtg tgtgtgtgtg     7620
tgtgtatgct tgcataccat ggagcatata cggagggagg tcagaggaca acttgtggca     7680
gtctgttctg ttcttcatgt aggttctagg aatggaagtc aaggaattgg cagccaaggt     7740
tctaggaatt ggcagcctgg cagcgtgtgt ctttatccac ttgagtcatc tctacagttc     7800
cctttcttta tttttgtttc ttttgtctgg gaattgaacc cagaaccttg cacatgctag     7860
taacacacgt caccactgag atatacccac agcctatatt attgtgttga tttgatttgg     7920
ggacagaatt cactcttccc actcgcttct gtcacggtac gattcttcag ctggggtgta     7980
taaaatgata ggcagagctc cttttggaag gtgtgctgct cgcactgggc ataataagct     8040
catgtacagt acttgagagg cggaagcagg ttgatctatg tgaattcaag atgagcctga     8100
cctacctaca tagcaagttt caggttagcc tgaactacac agcaagaccc tgtcctaaaa     8160
taaacaagca aacaaaacct aaggggctgg agagatggct cagcagcagt taagaacact     8220
tgttgctctt tcagacgact gaggttcagt tcccagcagt catgccagct tacacctgtc     8280
tgtaattcca gctccaggaa tctaaccccc cttctggcct cttctagtac tatacacacg     8340
tggtgaacag acgcaatgct ggtaaaacag ccatacacat aaagtgaaaa tacataagta     8400
taaagaaaag ttagcgtgat gatacacacc tatgatgcca gcactcaaag gcctgatgca     8460
ggaggatcat tgagtgcagg agctcagact caacttggac aacaaaataa ggctctgtct     8520
ccaaaggaaa aggaaaatcg aaattgtttg tacattgtaa atatctgaga tgcgggattc     8580
agagcgtata ctggcccata actcgtcgtc tcctgaggct gaggctgtgc cctgaccttc     8640
tcttttgctt tctcttcaga gtggtggaca acgaaggggc gctacagctg aagagaagct     8700
tccccattga acagagttcc caccctgtac gcagtatctt ctgcccccto atgtccttcc     8760 gccaggggc ctgtgtgggt aagtactag gctctgagga cctgcagcca gcctggttcc     8820
aacagcatga cacccgtgat tcctgggcc ctgtggtctc ttgtgcccta acagtgttat     8880 gcctagagc tttaaacatg gagccacaaa cagtttgaga acgccacagc tgagacacag     8940
agcccgcact gtcctcaaac ctcacatact cctcaccgaa ccaaaggagg cagatgagct     9000
cctatctagg gatggttcct tgtagactac cccaagctac ctgaggccct cacacctcac     9060
ataacctcaa gacttcatag tgggggtgtc acctagcccc ctgatcgcct ttccctctca     9120
tccggacagt gacaggcagt gaagatatgt gcgttcactt cttttgacgtg agcgggcag     9180 ccaaggctgc tgttaacaag ctgcagggcc acagcgcgcc cgtgcttgac gtcagcttca     9240
actgtgacga gagtctgctg gcctccagtg atgccagtgg catggtcatc gtctggagac     9300
gagagcaaaa gtagggttct gtcaccctgt gctgcccact gatccctcct ccttcactcc     9360
agtcttgcgt tataaattaa attcctgtgg ttgtgttgaa gggctctcag ctctcccacc     9420
aggaggcagt agggagctct caggcctcca gtggagtggg gaccagttcc tcgattgtgc     9480
agtgatgtgc tcatccattc aacaagcact tgctgagcat ctgctgtgat gtatcacgta     9540
ggcatgcagt cagtagaagg agggaggggta ccaactgtgg tcaggagctg ttctgggaag     9600
tagggataca gctatggctt caactgaaat tcctacccct gtgggctggc atcccagcag     9660
aggcaagcat acaggagaca gacgttctga gctgttctgg gaagtaggga tacagctgtg     9720
```

```
gcttcaactg acagaaattc ctacccctgt gggctggcat cccaatagag gcaagcacat    9780
gggagacgaa agtacagcca ttccttggtg tagaatttgc tttataattt ttcaacttta    9840 taaattttg  accttccagt ggtagcgaac cacacgcata tacccagttc tggttttctc    9900
ctttcagtat ggtgttcagt aaattatgtg agctagtcac tttgttataa aatagacttt    9960
gcattaggta agtttgccta actgtagaat aatgtcagcg ttgtgggcac atttaaggta   10020
ggtgacacta agctagggtg ttcggtaggt taggtatatt tatgcatttt caacataaga   10080
cagttcaaga cagatttgtt ggggtctaac cccgtgtgat gaagtcacat ctgtatataa   10140
tagagttaaa gatgagtgct aggaagaaaa gcaaagggcc agatgagctt gcacaaaagg   10200
gaggggcaaa gtcatcagga agagtgttcc caaccagatg acagttttaa agatctgagt   10260
gaaatagagc ctggaataat gtgattgggc ggagtgtatg agatgatggg agacaggtct   10320
ttgggacatc ttgggccata gcaaggaagg aagctttcct tattccctga gtgaggaagg   10380
tgaggaaggc tcagacagca gtagggaaat taggtgcaga atgttaagtt caaccacggg   10440
gctttcacca ggttaggttg tcaaactccc caacattggc agctactgtt tgggtggacc   10500
ccacacttgc ctgtgcgttg agttgtgtcc cacaagcagt gagcagaagt gtcgagttct   10560
tggagctaga ttagcatgca tacagccatg aactctgggg ctgagccaca gttcctgctg   10620
tggggtggaa gaaacagaaa atctctaagc tcacccctgt ctcctgccat gtctatctgg   10680
ggcccttatt tcagtcctgg acctgctcag agaccaaata ctaatgttca ttattgagta   10740
ttggcaagga gataaattac taaatgactc ttggtaatta ggtcatgacg aaatgtgaag   10800
gtttgaagaa tcaccaggag ttcttgcagc tcccatatgc tactacattt gtagcaattg   10860
gaactttggc taacatcctg gaaccgctga gtcttgccaa cctggtgatc tatagaacta   10920
acagcagctc tttgaggaaa aaagatgatt tcctatttgt ttcgtttctt gtttaagagt   10980
atggtcactt ccagccaaaa catttctgac tccatcagtc agattttagg caaatggtta   11040
ttagattgga atgttagtga gctggactgg tcattgtagt caagatcata tatgtgtgcc   11100
aacatcccta atccagcttc agggtcagtg attttttctat gaggactgta acttactata   11160
gcaaagggtg ccagacagca attaagtgct aatctcttta aagaccctcc caaggttagc   11220
agttcagacc tgtgcactgg ctcttctgta ccaaatggat gcacttattc agccaaggtc   11280
tgggggtagc aacagaattt gggtacataa cagttttctc taactttctc cttttcttca   11340
ctctctccat tttctttaat gagtctggtt tcaggatgat tggtgatgaa tattgtttgc   11400
atgattttgg gggggttcct tgtgcaattt ttgaggtggc agagttgaca ttaaattatc   11460
tactttaaat tatcttggtg acacttttgt ctcacaacct gaaggaaaat aaacactgag   11520
caaacaagaa agaataaaaa ataatgttgc tggttaga                           11558
```

<210> SEQ ID NO 2
<211> LENGTH: 6934
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Wdr13 Targeting Vector with artificially
      inserted sequences from position 1616 - 2756 in place of partial-
      intron1, exon 2, intron 2 and partial-exon 3 of the Wdr13 gene
<220> FEATURE:
<221> NAME/KEY: modified_base
<222> LOCATION: (3756)..(3756)
<223> OTHER INFORMATION: a, c, t or g

<400> SEQUENCE: 2

```
aagcttgttt tcctaattgc atatttttat taagatactc caagtttcct aggggtaacc      60
attcaagtcc agttagtccc agtgaagata cacatggatt cttcccatcg cataggtgtt     120
tagagattca tcactgcgct aggaactaga gaatgttcca ggagtcagtc tctgcatata     180
ttttatttgc ctggccaaat gtgtgctgct aagaagcagc ctaaaccact ttcatgagaa     240
agtcttattt ctgattttta gctagtggtt ggcacacgca ttcttgtcct tctgatcaca     300
gtacattatc cctgtgtata caaaaggtgt caagagggaa atgaatagaa ctcaaggggt     360
ggagcctcgg tccttgtatg ggaaactaca gtcctttaat gcgcctgcga ggctcccacg     420
ccccgggaaa ggttcctatc gatttgctct gtgctccgca gctctttctc gttgcaggca     480
gccatcttgc ctggagcttg agacagggag aagagagaga aggaaccggt gacactgggc     540
tcagggtcgc ggggggggg ggggcgcctc aagagctagg ggtagccccg gaggtggtcc     600
tggatcctga gctatgctct aggactagaa aaggaaggc ggagggcaga aggcttgatg     660
ggtggggaat gtcaaacaag acttgctatg ggggggaggg gcgttgctac ggcaactgga     720
gagggcgggg tcatgtctga actgctgctg tgagtcaccg gagtgctgcc caggaaaggc     780
agggctgggg tgatgaccac gctaacgacc cagtgggatt tcgcgacatc acctgtgtgg     840
agggacttcg tgtctatggc aactgtcacc tggtgggcgg aactagattt tctctgcctg     900
ggacgctgac attccaagcc cttgccctgc aggctcccgc aggcagacaa accaaagaag     960
gaagccaggg aatggccgcg tgtggcagc aagtattagc agtggacgcg aggtgaggcg    1020
tggggttgga gcccatggga gaggaactta ctgtggtgca tgagcaatgg cgataagtgc    1080
agctgggcgg aaaagttggc tggtgcggct gcgtgagcat gcgcagtagc ttggtgtggg    1140
atagtcctgc ggttaagtgg cctgggctgg agccggttct aaagagcatg ctgggaaaat    1200
gcggtttgaa atgacatgc gcagactgtc tttgagtggg tagtggaagt caggctggtg    1260
acttcctatc tagtccctca ttgcttatcc tcttccccaa cttttctcga tatcactacc    1320
ctactattat tacaattgct acccccatact aacctctacc gttatctgac cctaacctcc    1380
attgttgtac attaccaatc tgacgtatgt catcatgcta gactgatatt acagctggcc    1440
cagactgacc ccaacagagc tgcaaattga ctatattgtc gctagagtga tcttttcatc    1500
ataaccacta attattgcat aattgccccc catcacaatc ccaagagaaa tcccccttg    1560
ctgctcttgt tcactcttac catcccagtc actgccaaac cttgtaccac ctcgagcagt    1620
gtggttttca agaggaagca aaaagcctct ccacccaggc ctggaatgtt tccacccaat    1680
gtcgagcagt gtggttttgc aagaggaagc aaaaagcctc tccacccagg cctggaatgt    1740
ttccacccaa tgtcgagcaa accccgccca gcgtcttgtc attggcgaat cgaacacgc    1800
agatgcagtc ggggcggcgc ggtcccaggt ccacttcgca tattaaggtg acgcgtgtgg    1860
cctcgaacac cgagcgaccc tgcagccaat atgggatcgg ccattgaaca agatggattg    1920
cacgcaggtt ctccggccgc ttgggtggag aggctattcg gctatgactg gcacaacag    1980
acaatcggct gctctgatgc cgccgtgttc cggctgtcag cgcaggggcg cccggttctt    2040
tttgtcaaga ccgacctgtc cggtgccctg aatgaactgc aggacgaggc agcgcggcta    2100
tcgtggctgg ccacgacggg cgttccttgc gcagctgtgc tcgacgttgt cactgaagcg    2160
ggaagggact ggctgctatt gggcgaagtg ccggggcagg atctcctgtc atctcacctt    2220
gctcctgccg agaaagtatc catcatggct gatgcaatgc ggcggctgca tacgcttgat    2280
```

```
ccggctacct gcccattcga ccaccaagcg aaacatcgca tcgagcgagc acgtactcgg    2340
atggaagccg gtcttgtcga tcaggatgat ctggacgaag agcatcaggg gctcgcgcca    2400
gccgaactgt tcgccaggct caaggcgcgc atgcccgacg gcgaggatct cgtcgtgacc    2460
catggcgatg cctgcttgcc gaatatcatg gtggaaaatg gccgcttttc tggattcatc    2520
gactgtggcc ggctgggtgt ggcggaccgc tatcaggaca tagcgttggc tacccgtgat    2580
attgctgaag agcttggcgg cgaatgggct gaccgcttcc tcgtgcttta cggtatcgcc    2640
gctcccgatt cgcagcgcat cgccttctat cgccttcttg acgagttctt ctgaggggat    2700
cggcaataaa aagacagaat aaaacgcacg ggtgttgggt cgtttgttcg gatccgtcga    2760
ggacaccgcc gatctgtcag ccgaggttcc taccagctgc aggcacaaat gaaccgtgca    2820
gtctatgagg acaggtacat accagaggca ggcaggggt ggagattcac caggaggaga     2880
ggggccctgg gacgtggcag tctgaacacc catacctacc tcctatcacc ccttcccacc    2940
tcctgttggg gctcaggcct cctggcagtg tggtacccac gtcggtggca gaggcaagtc    3000
gggccatggc cggggacacg tcgctgagtg agaactatgc ctttgcaggc atgtaccatg    3060
tttttgacca acacgtggat gaggcaggtg agctaatggg tggtagggcc catcaccaaa    3120
catttgttca aacaactacc caaggcatcc ttttctagat ctagaatgca aggcctctga    3180
caccatacct cagaaggagg aaatagcact gataaaacct ttagcaaagc caagcagtga    3240
tggcgcacac ctctaattcc agcactcggg aggcaggtgg atttgagttc gaggccagcc    3300
tggtctacag agtgagttcc aggacagcca gggctacaca gagaaaccct gtctcggaaa    3360
aagaaaaaga aaaaaaaac ctttagcaaa tgcaaaagcc ctcttgcaaa gtggtccaag     3420
aaggttttgg taatgtaggt actggaaaga gctacacaaa cccaagagag tcctttgtag    3480
caggctgcct gagtgtttga gtctcttaga agagttcaaa acctttgctg atggtaactc    3540
ccttgtagag gccacagtgg gccacaatgt gtggatggtt ttgcaaactc ctgagagctt    3600
gattattgta aagtactcaa taagacagta caattttgtgc attgcaaaag acttttgtag   3660
tcctcaaagt gtctgctaag atttagagag catttggca gtaggccttc taagattaca     3720
actgccttg tcggccaagg aaagtccttt gttgangcta ctgttccttg tgctcagtga     3780
atgtgttgac tcccacaaat ggctcttggc atttgcagtc ccaagggtgc gcttcgccaa    3840
tgacgaccgg caccgcctgg cctgctgctc cctggacggc agcatctccc tgtgccagct    3900
ggtgcctgcc ccacccactg tgctccatgt gctacggggc catacgtg gcgtctcgga      3960
cttcgcctgg tccctctcca atgacatcct tgtgtccacc tccctcgatg ccaccatgcg    4020
catctgggcc tccgaggacg gccgctgcat ccgtgagatc cctgaccctg atggcgccga    4080
attgctctgc tgcaccttcc agccagtcaa caacaacctc actgtggtca ggctccagga    4140
cactgctcac caagggcggg catgctgggt ctggagggct gtcctggggc actagagaat    4200
aaggcttaat accccaagt cctatcccag ccgtcctgtg gtcagactca aagggaaaga     4260
gaccaacgaa aagcacagtt tgtggtctgg aatggccttg ctgtgtagac ttgtgtgtag    4320
actcccgagc tgggatggag gggttgtctc ctagccctgg gattccactg gtcccatcca    4380
ccacagtctc acagttttct gtctacaggg gctgctgcta ggggcagga tgatgaggct     4440
gaaagctcat ctagtctgtc agtggcagcc ccactgttgt cagactccag acagactgg     4500
ccagagggca gaggaaggac atggaaagtc tggcatgacc tggggggtag ggagttgaaa    4560
tataggggaa caacaggcca tgagtgagct agcgcttggg gctctgtctc tttgtaatgg    4620
tagcagctca tgggcttcag gaggggacag tccagggtat aagggaaaga tgtaaaggtg    4680
```

```
tcacaaggcg aggttttcag actcagagac taagactgct ttggtctcgt gagaccaact    4740
attgtgggca ttttgagggc acagctaagg agtaggaatt gtgcctgggt caccttctgg    4800
tatacctggc ctggtcccac tgtgttaaac acaaaggact agatggctca gaatgatggt    4860
gtatgcctgt cacccacagg tggggaacgc caagcacaac gtgcatgtca tgaacatctc    4920
cacaggcaag aaagtgaagg gtggctccag caagctcacc ggccgcgtcc tcgccctgtc    4980
ctttgatgcc cctggtcggc tgctctgggc aggcgatgac cgcggcagtg tcttctcctt    5040
tctctttgac atggccacag gtaggcagac cacagacttc gggttcggta cccctggttt    5100
tcattctccc aggactcagt ccttgtcctc cactgattca ggaaagctga ccaaagccaa    5160
gcgactagta gtgcatgaag gcagccctgt aaccagcatt ctgcccggt cctgggtcag     5220
ccgtgaagca cgggacccct ctctgctcat caatgcctgc ctcaacaagc tgctactcta    5280
caggtgggtt cctcccccag agtggaacaa gaacctgtct ctgtcacatt aatttcacca    5340
aggacagagg acctcataat atgatgagga tagggtcgga gatgtaactt agtggcagag    5400
tgctgatcta gctggtacag agctgtgtgt tccatcccca gaaacacgcc acatacacac    5460
acacagtata tatctatatc tatgtctatg tctatatatt tgtgtgtgta tatatatata    5520
cacatatata tacatacata tatatatata tatatttata tagtgattcc ttacctacta    5580
tatatatata tactatgcaa taatggtgat atcaatagca acataaatag gaatagcagt    5640
aataagactc tacatgaaca ttgctatggc taggtcccat tcaaagcact ttgtatatat    5700
cacctatttt aatcttcaca atcagtggta gagcactcgc ctagcatgta taaggctgtg    5760
ggttccactc tcaacattat aactaaagaa aaaaccacca gcacctattc ctctttcctt    5820
gttttgaatt tttcacgtgt gtgtgtgtgt gtgtgtgtat gcttgcatac catggagcat    5880
atacggaggg aggtcagagg acaacttgtg gcagtctgtt ctgttcttca tgtaggttct    5940
aggaatggaa gtcaaggaat tggcagccaa ggttctagga attggcagcc tggcagcgtg    6000
tgtctttatc cacttgagtc atctctacag ttcccttct ttatttttgt ttcttttgtc     6060
tgggaattga acccagaacc ttgcacatgc tagtaacaca cgtcaccact gagatatacc    6120
cacagcctat attattgtgt tgatttgatt tggggacaga attcactctt cccactcgct    6180
tctgtcacgg tacgattctt cagctggggt gtataaaatg ataggcagag ctcctttgg    6240
aaggtgtgct gctcgcactg gcataataa gctcatgtac agtacttgag aggcggaagc     6300
aggttgatct atgtgaattc aagatgagcc tgacctacct acatagcaag tttcaggtta    6360
gcctgaacta cacagcaaga ccctgtccta aataaacaa gcaaacaaaa cctaaggggc     6420
tggagagatg gctcagcagc agttaagaac acttgttgct ctttcagacg actgaggttc    6480
agttcccagc agtcatgcca gcttacacct gtctgtaatt ccagctccag gaatctaacc    6540
cctcttctgg cctcttctag tactatacac acgtggtgaa cagacgcaat gctggtaaaa    6600
cagccataca cataaagtga aaatacataa gtataaagaa aagttagcgt gatgatacac    6660
acctatgatg ccagcactca aaggcctgat gcaggaggat cattgagtgc aggagctcag    6720
actcaacttg gacaacaaaa taaggctctg tctccaaagg aaaaggaaaa tcgaaattgt    6780
ttgtacattg taaatatctg agatgcagga ttcagagcgt atactggccc ataactcgtc    6840
gtctcctgag gctgaggctg tgccctgacc ttctcttttg ctttctcttc agagtggtgg    6900
acaacgaagg ggcgctacag ctgaagagaa gctt                                 6934
```

<210> SEQ ID NO 3

<211> LENGTH: 6875
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pCMV-FLAG-Wdr13 from position 922 to 2443 - for overexpression of FLAG tagged WDR13 protein

<400> SEQUENCE: 3

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccatggacta | caaggacgac | gatgacaagg | aattccggat | 960 |
| ggccgcggtg | tggcagcaag | tattagcagt | ggacgcgagg | tacaacgcct | accgtacacc | 1020 |
| aacgtttcca | cagtttcgga | cccagtatat | ccgccggcgc | agccagctgc | ttcgggagaa | 1080 |
| tgccaaagct | ggtcaccccc | cagcattgcg | tcggcagtac | ctgaggctac | ggggccagct | 1140 |
| attgggccaa | cggtacgggc | cactctcaga | accaggcagt | gctcgtgcct | atagcaacag | 1200 |
| cattgtccgc | agcagccgaa | caaccctgga | tcgaatggag | gactttgaag | atgaccccag | 1260 |
| agccctgggg | gctcgaggac | accgccgatc | tgtcagccga | ggttcctacc | agctgcaggc | 1320 |
| acaaatgaac | cgtgcagtct | atgaggacag | gcctcctggc | agtgtggtac | ccacgtcggt | 1380 |
| ggcagaggca | agtcgggcca | tggccgggga | cacgtcgctg | agtgagaact | atgcctttgc | 1440 |
| aggcatgtac | catgttttg | accaacacgt | ggatgaggca | gtcccaaggg | tgcgcttcgc | 1500 |
| caatgacgac | cggcaccgcc | tggcctgctg | ctcccctgga | ggcagcatct | ccctgtgcca | 1560 |
| gctggtgcct | gccccaccca | ctgtgctcca | tgtgctacgg | ggccatacac | gtggcgtctc | 1620 |
| ggacttcgcc | tggtccctct | ccaatgacat | ccttgtgtcc | acctccctcg | atgccaccat | 1680 |
| gcgcatctgg | gcctccgagg | acggccgctg | catccgtgag | atccctgacc | ctgatggcgc | 1740 |
| cgaattgctc | tgctgcacct | tccagccagt | caacaacaac | ctcactgtgg | tggggaacgc | 1800 |
| caagcacaac | gtgcatgtca | tgaacatctc | cacaggcaag | aaagtgaagg | gtggctccag | 1860 |
| caagctcacc | ggccgcgtcc | tcgccctgtc | ctttgatgcc | cctggtcggc | tgctctgggc | 1920 |
| aggcgatgac | cgcggcagtg | tcttctcctt | tctctttgac | atggccacag | gaaagctgac | 1980 |
| caaagccaag | cgactagtag | tgcatgaagg | cagccctgta | accagcattt | ctgcccggtc | 2040 |

```
ctgggtcagc cgtgaagcac gggacccctc tctgctcatc aatgcctgcc tcaacaagct    2100
gctactctac agagtggtgg acaacgaagg ggcgctacag ctgaagagaa gcttccccat    2160
tgaacagagt tcccaccctg tacgcagtat cttctgcccc ctcatgtcct tccgccaggg    2220
ggcctgtgtg gtgacaggca gtgaagtat gtgcgttcac ttctttgacg tggagcgggc    2280
agccaaggct gctgttaaca agctgcaggg ccacagcgcg cccgtgcttg acgtcagctt    2340
caactgtgac gagagtctgc tggcctccag tgatgccagt ggcatggtca tcgtctggag    2400
acgagagcaa aagtagggtt ctgtcaccct gtgctgctct agagggcccg tttaaacccg    2460
ctgatcagcc tcgactgtgc cttctagttg ccagccatct gttgtttgcc ctcccccgt    2520 gccttccttg accctggaag gtgccactcc cactgtcctt tcctaataaa atgaggaaat    2580
tgcatcgcat tgtctgagta ggtgtcattc tattctgggg ggtggggtgg ggcaggacag    2640
caagggggag gattgggaag acaatagcag gcatgctggg gatgcggtgg gctctatggc    2700
ttctgaggcg gaaagaacca gctggggctc taggggtat ccccacgcgc cctgtagcgg    2760
cgcattaagc gcggcgggtg tggtggttac gcgcagcgtg accgctacac ttgccagcgc    2820
cctagcgccc gctcctttcg ctttcttccc ttcctttctc gccacgttcg ccggctttcc    2880
ccgtcaagct ctaaatcggg ggctcccttt agggttccga tttagtgctt tacggcacct    2940
cgaccccaaa aaacttgatt agggtgatgg ttcacgtagt gggccatcgc cctgatagac    3000
ggtttttcgc cctttgacgt tggagtccac gttctttaat agtggactct gttccaaac    3060 tggaacaaca ctcaaccta tctcggtcta ttctttgat ttataaggga ttttgccgat    3120
ttcggcctat tggttaaaaa atgagctgat ttaacaaaaa tttaacgcga attaattctg    3180
tggaatgtgt gtcagttagg gtgtggaaag tccccaggct ccccagcagg cagaagtatg    3240
caaagcatgc atctcaatta gtcagcaacc aggtgtggaa agtccccagg ctccccagca    3300
ggcagaagta tgcaaagcat gcatctcaat tagtcagcaa ccatagtccc gcccctaact    3360
ccgcccatcc cgcccctaac tccgcccagt tccgcccatt ctccgcccca tggctgacta    3420
atttttttta tttatgcaga ggccgaggcc gcctctgcct ctgagctatt ccagaagtag    3480
tgaggaggct tttttggagg cctaggcttt tgcaaaaagc tcccgggagc ttgtatatcc    3540
attttcggat ctgatcaaga gacaggatga ggatcgtttc gcatgattga acaagatgga    3600
ttgcacgcag gttctccggc cgcttgggtg gagaggctat tcggctatga ctgggcacaa    3660
cagacaatcg gctgctctga tgccgccgtg ttccggctgt cagcgcaggg gcgcccggtt    3720 cttttgtca agaccgacct gtccggtgcc ctgaatgaac tgcaggacga ggcagcgcgg    3780
ctatcgtggc tggccacgac gggcgttcct tgcgcagctg tgctcgacgt tgtcactgaa    3840
gcgggaaggg actggctgct attgggcgaa gtgccgggc aggatctcct gtcatctcac    3900
cttgctcctg ccgagaaagt atccatcatg gctgatgcaa tgcggcggct gcatacgctt    3960
gatccggcta cctgcccatt cgaccaccaa gcgaaacatc gcatcgagcg agcacgtact    4020
cggatggaag ccggtcttgt cgatcaggat gatctggacg aagagcatca ggggctcgcg    4080
ccagccgaac tgttcgccag gctcaaggcg cgcatgcccg acggcgagga tctcgtcgtg    4140
acccatggcg atgcctgctt gccgaatatc atggtggaaa atggccgctt ttctggattc    4200
atcgactgtg gccggctggg tgtggcggac cgctatcagg acatagcgtt ggctacccgt    4260
gatattgctg aagagcttgg cggcgaatgg gctgaccgct tcctcgtgct ttacggtatc    4320
gccgctcccg attcgcagcg catcgccttc tatcgccttc ttgacgagtt cttctgagcg    4380
```

```
ggactctggg gttcgaaatg accgaccaag cgacgcccaa cctgccatca cgagatttcg    4440
attccaccgc cgccttctat gaaaggttgg gcttcggaat cgttttccgg gacgccggct    4500
ggatgatcct ccagcgcggg gatctcatgc tggagttctt cgcccacccc aacttgttta    4560
ttgcagctta taatggttac aaataaagca atagcatcac aaatttcaca ataaagcat    4620 ttttttcact gcattctagt tgtggtttgt ccaaactcat caatgtatct tatcatgtct    4680
gtataccgtc gacctctagc tagagcttgg cgtaatcatg gtcatagctg tttcctgtgt    4740
gaaattgtta tccgctcaca attccacaca acatacgagc cggaagcata agtgtaaag    4800 cctggggtgc ctaatgagtg agctaactca cattaattgc gttgcgctca ctgcccgctt    4860
tccagtcggg aaacctgtcg tgccagctgc attaatgaat cggccaacgc gcggggagag    4920
gcggtttgcg tattgggcgc tcttccgctt cctcgctcac tgactcgctg cgctcggtcg    4980
ttcggctgcg gcgagcggta tcagctcact caaaggcggt aatacggtta tccacagaat    5040
caggggataa cgcaggaaag aacatgtgag caaaaggcca gcaaaaggcc aggaaccgta    5100
aaaaggccgc gttgctggcg tttttccata ggctccgccc ccctgacgag catcacaaaa    5160
atcgacgctc aagtcagagg tggcgaaacc cgacaggact ataaagatac caggcgtttc    5220
cccctggaag ctccctcgtg cgctctcctg ttccgaccct gccgcttacc ggatacctgt    5280
ccgcctttct cccttcggga agcgtggcgc tttctcatag ctcacgctgt aggtatctca    5340
gttcggtgta ggtcgttcgc tccaagctgg gctgtgtgca cgaaccccc gttcagcccg    5400 accgctgcgc cttatccggt aactatcgtc ttgagtccaa cccggtaaga cacgacttat    5460
cgccactggc agcagccact ggtaacagga ttagcagagc gaggtatgta ggcggtgcta    5520
cagagttctt gaagtggtgg cctaactacg gctacactag aagaacagta tttggtatct    5580
gcgctctgct gaagccagtt accttcggaa aaagagttgg tagctcttga tccggcaaac    5640
aaaccaccgc tggtagcggt ttttttgttt gcaagcagca gattacgcgc agaaaaaaag    5700
gatctcaaga agatcctttg atcttttcta cggggtctga cgctcagtgg aacgaaaact    5760
cacgttaagg gattttggtc atgagattat caaaaaggat cttcacctag atcctttta    5820 attaaaaatg aagttttaaa tcaatctaaa gtatatatga gtaaacttgg tctgacagtt    5880
accaatgctt aatcagtgag gcacctatct cagcgatctg tctatttcgt tcatccatag    5940
ttgcctgact ccccgtcgtg tagataacta cgatacggga gggcttacca tctggcccca    6000
gtgctgcaat gataccgcga gacccacgct caccggctcc agatttatca gcaataaacc    6060
agccagccgg aagggccgag cgcagaagtg gtcctgcaac tttatccgcc tccatccagt    6120
ctattaattg ttgccgggaa gctagagtaa gtagttcgcc agttaatagt ttgcgcaacg    6180
ttgttgccat tgctacaggc atcgtggtgt cacgctcgtc gtttggtatg gcttcattca    6240
gctccggttc ccaacgatca aggcgagtta catgatcccc catgttgtgc aaaaaagcgg    6300
ttagctcctt cggtcctccg atcgttgtca agtaagtt ggccgcagtg ttatcactca    6360
tggttatggc agcactgcat aattctctta ctgtcatgcc atccgtaaga tgcttttctg    6420
tgactggtga gtactcaacc aagtcattct gagaatagtg tatgcggcga ccgagttgct    6480
cttgcccggc gtcaatacgg gataataccg cgccacatag cagaacttta aaagtgctca    6540
tcattggaaa acgttcttcg ggcgaaaac tctcaaggat cttaccgctg ttgagatcca    6600
gttcgatgta acccactcgt gcacccaact gatcttcagc atcttttact ttcaccagcg    6660
tttctgggtg agcaaaaaca ggaaggcaaa atgccgcaaa aaagggaata agggcgacac    6720
ggaaatgttg aatactcata ctcttccttt ttcaatatta ttgaagcatt tatcagggtt    6780
```

```
attgtctcat gagcggatac atatttgaat gtatttagaa aaataaacaa atagggttc      6840 cgcgcacatt tccccgaaaa gtgccacctg acgtc                                 6875

<210> SEQ ID NO 4
<211> LENGTH: 6906
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pCMV-Myc-Wdr13 FROM POSITION 900 - 2448- for
      overexpression of Myc tagged WDR13 protein

<400> SEQUENCE: 4
gacggatcgg gagatctccc gatccctat ggtcgactct cagtacaatc tgctctgatg       60
ccgcatagtt aagccagtat ctgctccctg cttgtgtgtt ggaggtcgct gagtagtgcg     120
cgagcaaaat taagctaca acaaggcaag gcttgaccga caattgcatg aagaatctgc      180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gcttggtacc    900
atggaggagc agaagctgat ctcagaggag gacctgcata tggccatgga ggccgaattc    960
cggatggccg cggtgtggca gcaagtatta gcagtggacg cgaggtacaa cgcctaccgt   1020
acaccaacgt ttccacagtt tcggacccag tatatccgcc ggcgcagcca gctgcttcgg   1080
gagaatgcca agctggtca ccccccagca ttgcgtcggc agtacctgag gctacggggc    1140
cagctattgg gccaacggta cgggccactc tcagaaccag gcagtgctcg tgcctatagc    1200
aacagcattg tccgcagcag ccgaacaacc cttgatcgaa tggaggactt tgaagatgac   1260
cccagagccc tggggctcg aggacaccgc cgatctgtca gccgaggttc ctaccagctg    1320
caggcacaaa tgaaccgtgc agtctatgag acaggcctc ctggcagtgt ggtacccacg    1380
tcggtggcag aggcaagtcg ggccatggcc gggacacgt cgctgagtga aactatgcc    1440 tttgcaggca tgtaccatgt ttttgaccaa cacgtggatg aggcagtccc aagggtgcgc   1500
ttcgccaatg acgaccggca ccgcctggcc tgctgctccc tggacggcag catctccctg   1560
tgccagctgg tgcctgcccc acccactgtg ctccatgtgc acggggcca tacacgtggc    1620 gtctcggact cgcctggtc cctctccaat gacatccttg tgtccacctc cctcgatgcc    1680
accatgcgca tctgggcctc cgaggacggc cgctgcatcc gtgagatccc tgaccctgat   1740
ggcgccgaat tgctctgctg caccttccag ccagtcaaca caacctcac tgtggtgggg    1800
```

-continued

```
aacgccaagc acaacgtgca tgtcatgaac atctccacag gcaagaaagt gaagggtggc    1860
tccagcaagc tcaccggccg cgtcctcgcc ctgtcctttg atgcccctgg tcggctgctc    1920
tgggcaggcg atgaccgcgg cagtgtcttc tcctttctct ttgacatggc cacaggaaag    1980
ctgaccaaag ccaagcgact agtagtgcat gaaggcagcc ctgtaaccag catttctgcc    2040
cggtcctggg tcagccgtga agcacgggac ccctctctgc tcatcaatgc ctgcctcaac    2100
aagctgctac tctacagagt ggtggacaac aagggggcgc tacagctgaa gagaagcttc    2160
cccattgaac agagttccca ccctgtacgc agtatcttct gcccctcat gtccttccgc     2220 caggggcct gtgtggtgac aggcagtgaa gatatgtgcg ttcacttctt tgacgtggag     2280
cgggcagcca aggctgctgt taacaagctg cagggccaca gcgcgcccgt gcttgacgtc    2340
agcttcaact gtgacgagag tctgctggcc tccagtgatg ccagtggcat ggtcatcgtc    2400
tggagacgag agcaaaagta gggttctgtc accctgtgct gctctagagg gccctattct    2460
atagtgtcac ctaaatgcta gagctcgctg atcagcctcg actgtgcctt ctagttgcca    2520
gccatctgtt gtttgcccct cccccgtgcc ttccttgacc ctggaaggtg ccactcccac    2580
tgtcctttcc taataaaatg aggaaattgc atcgcattgt ctgagtaggt gtcattctat    2640
tctggggggt ggggtggggc aggacagcaa gggggaggat tgggaagaca atagcaggca    2700
tgctggggat gcggtgggct ctatggcttc tgaggcggaa agaaccagct ggggctctag    2760
ggggtatccc cacgcgccct gtagcggcgc attaagcgcg gcgggtgtgg tggttacgcg    2820
cagcgtgacc gctacacttg ccagcgccct agcgcccgct cctttcgctt tcttcccttc    2880 cttttctcgcc acgttcgccg gctttccccg tcaagctcta aatcggggca tccctttagg    2940
gttccgattt agtgctttac ggcacctcga ccccaaaaaa cttgattagg gtgatggttc    3000
acgtagtggg ccatcgccct gatagacggt ttttcgccct ttgacgttgg agtccacgtt    3060
ctttaatagt ggactcttgt tccaaactgg aacaacactc aaccctatct cggtctattc    3120
ttttgattta aagggatttt tggggattttc ggcctattgg ttaaaaaatg agctgattta    3180
acaaaaattt aacgcgaatt aattctgtgg aatgtgtgtc agttagggtg tggaaagtcc    3240
ccaggctccc caggcaggca gaagtatgca aagcatgcat ctcaattagt cagcaaccag    3300
gtgtggaaag tccccaggct ccccagcagg cagaagtatg caaagcatgc atctcaatta    3360
gtcagcaacc atagtcccgc ccctaactcc gcccatcccg ccctaactc cgcccagttc     3420 cgcccattct ccgccccatg gctgactaat ttttttttatt tatgcagagg ccgaggccgc    3480
ctctgcctct gagctattcc agaagtagtg aggaggcttt tttggaggcc taggcttttg    3540
caaaaagctc ccgggagctt gtatatccat tttcggatct gatcaagaga caggatgagg    3600
atcgtttcgc atgattgaac aagatggatt gcacgcaggt tctccggccg cttgggtgga    3660
gaggctattc ggctatgact gggcacaaca gacaatcggc tgctctgatg ccgccgtgtt    3720
ccggctgtca gcgcagggc gcccggttct ttttgtcaag accgacctgt ccggtgccct     3780
gaatgaactg caggacgagg cagcgcggct atcgtggctg gccacgacgg gcgttccttg    3840
cgcagctgtg ctcgacgttg tcactgaagc gggaagggac tggctgctat gggcgaagt     3900 gccggggcag gatctcctgt catctcacct tgctcctgcc gagaaagtat ccatcatggc    3960
tgatgcaatg cggcggctgc atacgcttga tccggctacc tgcccattcg accaccaagc    4020
gaaacatcgc atcgagcgag cacgtactcg gatggaagcc ggtcttgtcg atcaggatga    4080
tctggacgaa gagcatcagg ggctcgcgcc agccgaactg ttcgccaggc tcaaggcgcg    4140
catgcccgac ggcgaggatc tcgtcgtgac ccatggcgat gcctgcttgc cgaatatcat    4200
```

```
ggtggaaaat ggccgctttt ctggattcat cgactgtggc cggctgggtg tggcggaccg    4260
ctatcaggac atagcgttgg ctacccgtga tattgctgaa gagcttggcg gcgaatgggc    4320
tgaccgcttc ctcgtgcttt acggtatcgc cgctcccgat cgcagcgca tcgccttcta    4380 tcgccttctt gacgagttct tctgagcggg actctgcggt tcgaaatgac cgaccaagcg    4440
acgcccaacc tgccatcacg agatttcgat tccaccgccg ccttctatga aggttgggc    4500 ttcggaatcg tttttccggga cgccggctgg atgatcctcc agcgcgggga tctcatgctg    4560
gagttcttcg cccacccccaa cttgtttatt gcagcttata atggttacaa ataaagcaat    4620
agcatcacaa atttcacaaa taaagcattt ttttcactgc attctagttg tggttttgtcc    4680 aaactcatca atgtatctta tcatgtctgt ataccgtcga cctctagcta gagcttggcg    4740
taatcatggt catagctgtt tcctgtgtga aattgttatc cgctcacaat tccacacaac    4800
atacgagccg aagcataaa gtgtaaagcc tggggtgcct aatgagtgag ctaactcaca    4860
ttaattgcgt tgcgctcact gcccgctttc cagtcgggaa acctgtcgtg ccagctgcat    4920
taatgaatcg gccaacgcgc ggggagaggc ggtttgcgta ttgggcgctc ttccgcttcc    4980
tcgctcactg actcgctgcg ctcggtcgtt cggctgcggc gagcggtatc agctcactca    5040
aaggcggtaa tacggttatc cacagaatca ggggataacg caggaaagaa catgtgagca    5100
aaaggccagc aaaaggccag gaaccgtaaa aaggccgcgt tgctggcgtt tttccatagg    5160
ctccgccccc ctgacgagca tcacaaaaat cgacgctcaa gtcagaggtg gcgaaacccg    5220
acaggactat aaagatacca ggcgtttccc cctggaagct ccctcgtgcg ctctcctgtt    5280
ccgaccctgc cgcttaccgg atacctgtcc gcctttctcc cttcgggaag cgtggcgctt    5340
tctcaatgct cacgctgtag gtatctcagt tcggtgtagg tcgttcgctc caagctgggc    5400
tgtgtgcacg aaccccccgt tcagcccgac cgctgcgcct tatccggtaa ctatcgtctt    5460
gagtccaacc cggtaagaca cgacttatcg ccactggcag cagccactgg taacaggatt    5520
agcagagcga ggtatgtagg cggtgctaca gagttcttga agtggtggcc taactacggc    5580
tacactagaa ggacagtatt tggtatctgc gctctgctga agccagttac cttcggaaaa    5640
agagttggta gctcttgatc cggcaaacaa accaccgctg gtagcggtgg tttttttgtt    5700
tgcaagcagc agattacgcg cagaaaaaaa ggatctcaag aagatccttt gatcttttct    5760
acggggtctg acgctcagtg gaacgaaaac tcacgttaag ggattttggt catgagatta    5820
tcaaaaagga tcttcaccta gatcctttta aattaaaaat gaagttttaa atcaatctaa    5880
agtatatatg agtaaacttg gtctgacagt taccaatgct taatcagtga ggcacctatc    5940
tcagcgatct gtctatttcg ttcatccata gttgcctgac tccccgtcgt gtagataact    6000
acgatacggg agggcttacc atctggcccc agtgctgcaa tgataccgcg agacccacgc    6060
tcaccggctc cagatttatc agcaataaac cagccagccg aagggccga gcgcagaagt    6120 ggtcctgcaa ctttatccgc ctccatccag tctattaatt gttgccggga agctagagta    6180
agtagttcgc cagttaatag tttgcgcaac gttgttgcca ttgctacagg catcgtggtg    6240
tcacgctcgt cgtttggtat ggcttcattc agctccggtt cccaacgatc aaggcgagtt    6300
acatgatccc ccatgttgtg caaaaaagcg gttagctcct tcggtcctcc gatcgttgtc    6360
agaagtaagt tggccgcagt gttatcactc atggttatgg cagcactgca taattctctt    6420
actgtcatgc catccgtaag atgcttttct gtgactggtg agtactcaac caagtcattc    6480
tgagaatagt gtatgcggcg accgagttgc tcttgcccgg cgtcaatacg ggataatacc    6540
```

-continued

| | |
|---|---|
| gcgccacata gcagaacttt aaaagtgctc atcattggaa aacgttcttc ggggcgaaaa | 6600 |
| ctctcaagga tcttaccgct gttgagatcc agttcgatgt aacccactcg tgcacccaac | 6660 |
| tgatcttcag catcttttac tttcaccagc gtttctgggt gagcaaaaac aggaaggcaa | 6720 |
| aatgccgcaa aaaagggaat aagggcgaca cggaaatgtt gaatactcat actcttcctt | 6780 |
| tttcaatatt attgaagcat ttatcagggt tattgtctca tgagcggata catatttgaa | 6840 |
| tgtatttaga aaaataaaca aataggggtt ccgcgcacat ttccccgaaa agtgccacct | 6900 |
| gacgtc | 6906 |

<210> SEQ ID NO 5
<211> LENGTH: 10967
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pCMV-Myc-PHIP1 from position 900 - 6509 for
      overexpression of Myc tagged PHIP1 protein

<400> SEQUENCE: 5

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gcttggtacc | 900 |
| atggaggagc agaagctgat ctcagaggag gacctgcata tggccatgga ggccgaattc | 960 |
| ctctcggagc tgcgatcgga gctctacttc ctcatcgccc ggttcctgga agatggaccc | 1020 |
| tgtcagcagg cggctcaggt gctgatccgc gaagtggccg agaaggagct gctgccccgg | 1080 |
| cgcaccgact ggaccgggaa ggagcacccc aggacctacc agaatctggt gaagtattat | 1140 |
| agacaccttg cacctgatca cttgctgcaa atatgtcatc ggctaggacc tcttcttgag | 1200 |
| caagaaattc ctcagagtgt tcctggagta cagactttac taggagctgg aagacagtcc | 1260 |
| ttgctacgaa caaataaaag ctgcaagcat gtggtatgga aggatctgc cctggctgca | 1320 |
| ctgcactgtg ggaggccgcc agagtctcca gttaactacg gtagcccacc tagcattgcg | 1380 |
| gatactctgt tttcaaggaa gctgaatggg aaatacagac ttgaacgact tgttccaact | 1440 |
| gcagtttatc agcacatgaa gatgcataag cgaattcttg acacttatc atcggtgtac | 1500 |
| tgtgtaactt ttgatcgaac tggcaggcgg atatttactg gttctgatga ttgtcttgtg | 1560 |

```
aaaatctggg ccacagacga tggaagattg ctagctactt taagaggaca tgctgctgaa   1620
atatcagaca tggctgtaaa ctatgagaat actatgatag cagctggaag ttgtgataaa   1680
atgattcgtg tctggtgtct tcgaacctgt gcacctttgg ctgttcttca gggacatagt   1740
gcatctatta catcactaca gttctcacca ttgtgcagtg gctcaaagag atacctgtct   1800
tctacagggg cggacggcac tatttgcttt tggctttggg atgctggaac ccttaaaata   1860
aatccaagac ccacaaaatt tacagagcgt cctcggcctg gagtgcaaat gatatgttct   1920
tcgttcagtg ctggtgggat gttttttggcc actggaagca ctgaccatat tattagagtt   1980
```
aaaatctggg ccacagacga tggaagattg ctagctactt taagaggaca tgctgctgaa   1620
atatcagaca tggctgtaaa ctatgagaat actatgatag cagctggaag ttgtgataaa   1680
atgattcgtg tctggtgtct tcgaacctgt gcacctttgg ctgttcttca gggacatagt   1740
gcatctatta catcactaca gttctcacca ttgtgcagtg gctcaaagag atacctgtct   1800
tctacagggg cggacggcac tatttgcttt tggctttggg atgctggaac ccttaaaata   1860
aatccaagac ccacaaaatt tacagagcgt cctcggcctg gagtgcaaat gatatgttct   1920
tcgttcagtg ctggtgggat gttttttggcc actggaagca ctgaccatat tattagagtt   1980
tatttttttg gatcaggtca gccagaaaaa atatcagaat tggagtttca tactgacaaa   2040
gttgacagta tccagttttc aacactagt aacaggtttg tgagtggtag tcgtgatggg   2100
acagcacgaa tttggcagtt taaacgaagg gaatggaaaa gcattttgtt agatatggct   2160
actcgtccag caggccaaaa tcttcaaggc atagaagaca aaatcacaaa aatgaaagta   2220
actatggtag cttgggatcg acatgacaac acagttataa ctgcagttaa taacatgact   2280
ctgaaagttt ggaattctta tactggtcaa ctgatacatg ttctaatggg tcatgaagat   2340
gaggtgtttt tcttgagcc acacccattt gatcctagag ttctcttctc tgctggtcat   2400
gatggaaatg tgatagtgtg ggatctagca agaggagtca aagttcgatc ttatttcaat   2460
atgattgaag acaaggaca tggtgcagtg tttgactgca aatgctcccc tgatggtcag   2520
cactttgcat gtacagactc tcatggacat cttttaattt ttggttttgg gtccagtagc   2580
aagtatgaca agatagcaga tcagatgttt tttcacagtg attatcggcc tcttatccgt   2640
gatgcgaaca attttgtatt agatgagcag acgcagcagg cacctcacct catgcctccc   2700
ccttttctgg ttgatgttga tggaaatcct catccatcaa ggtaccagcg attggttcct   2760
ggtcgggaga actgcaggga ggagcagctc attcctcaga tgggagtaac ttcttcagga   2820
ttgaaccaag ttttgagcca gcaagcaaac caggatatta gtcctttaga cagcatgatt   2880
caaagactgc agcaggagca ggacctgagg cgttcgggtg aagcaggtgt tagtaatgcc   2940
agccgtgtga acagaggctc agtaagttct acctccgaag ttcattcacc accaaatata   3000
ggattaaggc gcagtggcca aatcgaaggt gtacggcaga tgcacagcaa tgctccgaga   3060
agtgaaatag ccacagagcg agatcttgtt gcttggagtc ggagggtagt agtgcctgag   3120
ctctcggctg gtgtggctag tagacaagaa gaatggagaa ctgcaaaggg agaagaggaa   3180
ataaagagtt atagatcaga agagaaaagg aaacacttaa ctgttgcaaa agagaataaa   3240
atacttactg tctcaaagaa tcatgctcat gagcatttcc tggatcttgg ggattctaaa   3300
aagcagcaag cgaatcagca caattaccgt acaagatctg cactggaaga aacacccagg   3360
cccttagagg agctagaaaa cggaactagt tcttcagatg aaggtgaagt acttgctgtc   3420
agtggtggga cttctgagga agaggagcga gcatggcaca gtgatggcag ctccagtgac   3480
tactccagtg attattctga ttggacagca gatgctggaa ttaacttgca gccaccaaag   3540
aaagttccta agcataaaac caagaaacca gaaagtagtt cagatgaaga agaagaatct   3600
gaaaaccaga agcaaaaaca tattaaaaag gaaagaaaaa aagcaaatga agaaaaagat   3660
ggaccaacat caccaaagaa aaaaaagccc aagaaagaa aacaaaagag attggctgta   3720
ggagaactaa ctgagaatgg cctaacgtta gaagagtggt tgccttcagc ttggattaca   3780
gacacacttc ccaggagatg tccatttgtg ccacagatgg gtgatgaggt ttattatttt   3840
cgacaagggc atgaagcata tgttgaaatg gcccggaaaa ataaaattta tagtatcaat   3900

```
cctaaaaagc agccatggca taagatggaa ctaagggaac aagaactaat gaaaattgtt   3960
ggtataaagt atgaagtggg gttgcctacc ctttgctgcc ttaaacttgc ttttctagat   4020
cctgatactg gcaaactgac cggtggatca tttaccatga ataccatga tatgcctgac    4080 gtcatagatt ttctagtctt gagacaacaa tttgatgatg caaagtatag acgatggaat   4140
ataggtgacc gcttcagatc tgtcatagat gatgcctggt ggtttggaac aattgaaagt   4200
caagagcctc ttcaacctga gtaccctgat agtttgtttc agtgttataa tgtatgttgg   4260
gacaatggag atacagaaaa gatgagtcct tgggatatga aattaatacc taataatgct   4320
gtctttccag aagaactggg taccagtgtt cctttaactg atgttgaatg taggtcgcta   4380
atttataaac ctcttgatgg agaatgggga gccaatccca gggatgaaga atgtgaaaga   4440
attgttggag gaataaatca gctgatgaca ctagatattg cgtctgcatt tgttgcccct   4500
gtggaccttc aagcttatcc catgtattgc actgtggtgg cctatccaac ggatctaagt   4560
acaattaaac aaagactgga gaacaggttt tacaggcgct tttcatcact aatgtgggaa   4620
gttcgatata tagaacataa tacacgaaca ttcaatgagc caggaagccc aattgtgaaa   4680
tctgctaaat ttgtgactga tcttctcctg cattttataa aggatcagac ttgttataac   4740
ataattccac tttacaactc aatgaagaag aaagttttgt ctgactctga ggaagaagag   4800
aaagatgctg atgttccagg gacttctacc agaaagcgca aggatcatca acctagaaga   4860
aggttacgca acagagctca gtcttacgat attcaggcat ggaagaaaca atgtcaagaa   4920
ttactgaatc tcatatttca atgtgaagac tcagaacctt tcgacagcc agtggatctt    4980 cttgaatatc cagactacag agacatcatt gacactccaa tggactttgc cactgttaga   5040
gagactttag aggctgggaa ttatgagtca cccatggagt tatgtaaaga tgtcaggctc   5100
attttcagta attctaaagc atacacacca agcaagagat caaggattta cagcatgagt   5160
ttacgcctgt ctgctttctt tgaagaacat attagttcag ttttgtcaga ttataaatct   5220
gctcttcgtt ttcataaaag aaacaccata agcaagaaga ggaagaagcg aaacaggagc   5280
agttccctgt ccagcagtgc tgcctcaagc cctgaaagga aaaaaggat cttaaaaccc     5340 cagctaaagt cagaagtatc tacctctcca ttctccatac ctacaagatc agtactacca   5400
agacataatg ctgcgcaaat gaatggtaaa ccagaatcca gttctgtggt tcgaactagg   5460
agcaaccgtg tagctgtaga tccagttgtc accgagcagc cctctacatc atcagccaca   5520
aaagcttttg tttcaaaaac taatacatct gccatgccag aaaagcaat gctagagaat    5580 tctgtgagac attccaaagc cttgagcaca ctttccagcc ctgatccgct cacattcagc   5640
catgctacaa agaataattc tgcaaaagaa acatggaaa aggaaaagcc tgtcaaacgt    5700
aaaatgaagt cttctgtgtt ttcaaaagca tctccacttc caaagtcagc cgcagtcata   5760
gagcaaggag agtgtaagaa caatgttctt ataccaggaa ccattcaagt aaatggccat   5820
ggaggacaac catcaaaact cgtgaagaga ggacctggga ggaagcccaa ggtagaagtt   5880
aacaccagca gtggtgaagt gacacacaag aaaagaggta gaaagcccaa gaatctgcag   5940
tgtgcaaagc aggaaaactc tgagcaaaat aacatgcatc ccatcagggc tgacgtgctt   6000
ccttcttcaa catgcaactt cctttctgaa actaatgctg tcaaggagga tttgttacag   6060
aaaaagagtc gtggaggcag aaaacccaaa aggaagatga aaactcacaa cctagattca   6120
gaactcatag ttcctacaaa tgttaaagtg ttaaggagaa gtaaccggaa aaaaacagat   6180
gatcctatag atgaggaaga ggagtttgaa gaactcaaag gctctgagcc tcacatgaga   6240
actagaaatc agggtcgaag gacagctttc tataatgagg atgactcgga ggaagaacag   6300
```

```
agacagctgt tgttcgagga cacctccttg acatttggaa cttctagtag aggacgagtc   6360
cgaaagttga ctgaaaaagc aaaggctaat ttaattggtt ggtaacttga agcaaaatat   6420
tgcattttaa aaaatctgta acgcaggtac agttaaggag taagtagaac taaggtctct   6480
gcttccttgc tgctatgacg gattctagag ggccctattc tatagtgtca cctaaatgct   6540
agagctcgct gatcagcctc gactgtgcct tctagttgcc agccatctgt tgtttgcccc   6600 tccccgtgc cttccttgac cctggaaggt gccactccca ctgtcctttc ctaataaaat   6660
gaggaaattg catcgcattg tctgagtagg tgtcattcta ttctgggggg tggggtgggg   6720
caggacagca aggggagga ttgggaagac aatagcaggc atgctgggga tgcggtgggc   6780
tctatggctt ctgaggcgga agaaccagc tggggctcta gggggtatcc ccacgcgccc   6840
tgtagcggcg cattaagcgc ggcgggtgtg gtggttacgc gcagcgtgac cgctacactt   6900
gccagcgccc tagcgcccgc tcctttcgct ttcttccctt cctttctcgc cacgttcgcc   6960
ggctttcccc gtcaagctct aaatcggggc atccctttag ggttccgatt tagtgcttta   7020
cggcacctcg accccaaaaa acttgattag ggtgatggtt cacgtagtgg gccatcgccc   7080
tgatagacgt ttttcgccc tttgacgttg gagtccacgt tctttaatag tggactcttg   7140
ttccaaactg gaacaacact caaccctatc tcggtctatt cttttgattt ataagggatt   7200
ttggggattt cggcctattg gttaaaaaat gagctgattt aacaaaaatt taacgcgaat   7260
taattctgtg gaatgtgtgt cagttagggt gtggaaagtc ccaggctcc ccaggcaggc   7320 agaagtatgc aaagcatgca tctcaattag tcagcaacca ggtgtggaaa gtccccaggc   7380
tccccagcag gcagaagtat gcaaagcatg catctcaatt agtcagcaac catagtcccg   7440
cccctaactc cgcccatccc gcccctaact ccgcccagtt ccgcccattc tccgccccat   7500
ggctgactaa ttttttttat ttatgcagag gccgaggccg cctctgcctc tgagctattc   7560
cagaagtagt gaggaggctt ttttggaggc ctaggctttt gcaaaaagct cccgggagct   7620
tgtatatcca ttttcggatc tgatcaagag acaggatgag gatcgtttcg catgattgaa   7680
caagatggat tgcacgcagg ttctccggcc gcttgggtgg agaggctatt cggctatgac   7740
tgggcacaac agacaatcgg ctgctctgat gccgccgtgt tccggctgtc agcgcagggg   7800
cgcccggttc ttttttgtcaa gaccgacctg tccggtgccc tgaatgaact gcaggacgag   7860
gcagcgcggc tatcgtggct ggccacgacg ggcgttcctt gcgcagctgt gctcgacgtt   7920
gtcactgaag cgggaaggga ctggctgcta ttgggcgaag tgccggggca ggatctcctg   7980
tcatctcacc ttgctcctgc cgagaaagta tccatcatgg ctgatgcaat gcggcggctg   8040
catacgcttg atccggctac ctgcccattc gaccaccaag cgaaacatcg catcgagcga   8100
gcacgtactc ggatggaagc cggtcttgtc gatcaggatg atctggacga agagcatcag   8160
gggctcgcgc cagccgaact gttcgccagg ctcaaggcgc gcatgcccga cggcgaggat   8220
ctcgtcgtga cccatggcga tgcctgcttg ccgaatatca tggtggaaaa tggccgcttt   8280
tctggattca tcgactgtgg ccggctgggt gtggcggacc gctatcagga catagcgttg   8340
gctacccgtg atattgctga agagcttggc ggcgaatggg ctgaccgctt cctcgtgctt   8400
tacggtatcg ccgctcccga ttcgcagcgc atcgccttct atcgccttct tgacgagttc   8460
ttctgagcgg gactctgggg ttcgaaatga ccgaccaagc gacgcccaac ctgccatcac   8520
gagatttcga ttccaccgcc gccttctatg aaaggttggg cttcggaatc gttttccggg   8580
acgccggctg gatgatcctc cagcgcgggg atctcatgct ggagttcttc gcccacccca   8640
```

```
acttgtttat tgcagcttat aatggttaca aataaagcaa tagcatcaca aatttcacaa    8700
ataaagcatt tttttcactg cattctagtt gtggtttgtc caaactcatc aatgtatctt    8760
atcatgtctg tataccgtcg acctctagct agagcttggc gtaatcatgg tcatagctgt    8820
ttcctgtgtg aaattgttat ccgctcacaa ttccacacaa catacgagcc ggaagcataa    8880
agtgtaaagc ctggggtgcc taatgagtga gctaactcac attaattgcg ttgcgctcac    8940
tgcccgcttt ccagtcggga aacctgtcgt gccagctgca ttaatgaatc ggccaacgcg    9000
cggggagagg cggtttgcgt attgggcgct cttccgcttc ctcgctcact gactcgctgc    9060
gctcggtcgt tcggctgcgg cgagcggtat cagctcactc aaaggcggta atacggttat    9120
ccacagaatc aggggataac gcaggaaaga acatgtgagc aaaaggccag caaaaggcca    9180
ggaaccgtaa aaaggccgcg ttgctggcgt ttttccatag gctccgcccc cctgacgagc    9240
atcacaaaaa tcgacgctca agtcagaggt ggcgaaaccc gacaggacta taaagatacc    9300
aggcgtttcc ccctggaagc tccctcgtgc gctctcctgt tccgaccctg ccgcttaccg    9360
gatacctgtc cgcctttctc ccttcgggaa gcgtggcgct ttctcaatgc tcacgctgta    9420
ggtatctcag ttcggtgtag gtcgttcgct ccaagctggg ctgtgtgcac gaaccccccg    9480
ttcagcccga ccgctgcgcc ttatccggta actatcgtct tgagtccaac ccggtaagac    9540
acgacttatc gccactggca gcagccactg gtaacaggat tagcagagcg aggtatgtag    9600
gcggtgctac agagttcttg aagtggtggc ctaactacgg ctacactaga aggacagtat    9660
ttggtatctg cgctctgctg aagccagtta ccttcggaaa aagagttggt agctcttgat    9720
ccggcaaaca aaccaccgct ggtagcggtg gttttttgt ttgcaagcag cagattacgc    9780
gcagaaaaaa aggatctcaa gaagatcctt tgatctttc tacggggtct gacgctcagt    9840
ggaacgaaaa ctcacgttaa gggattttgg tcatgagatt atcaaaaagg atcttcacct    9900
agatccttt aaattaaaaa tgaagtttta atcaatcta agtatatat gagtaaactt    9960
ggtctgacag ttaccaatgc ttaatcagtg aggcacctat ctcagcgatc tgtctatttc    10020
gttcatccat agttgcctga ctccccgtcg tgtagataac tacgatacgg gagggcttac    10080
catctggccc cagtgctgca atgataccgc gagacccacg ctcaccggct ccagatttat    10140
cagcaataaa ccagccagcc ggaagggccg agcgcagaag tggtcctgca actttatccg    10200
cctccatcca gtctattaat tgttgccggg aagctagagt aagtagttcg ccagttaata    10260
gtttgcgcaa cgttgttgcc attgctacag gcatcgtggt gtcacgctcg tcgtttggta    10320
tggcttcatt cagctccggt tcccaacgat caaggcgagt tacatgatcc cccatgttgt    10380
gcaaaaaagc ggttagctcc ttcggtcctc cgatcgttgt cagaagtaag ttggccgcag    10440
tgttatcact catggttatg gcagcactgc ataattctct tactgtcatg ccatccgtaa    10500
gatgcttttc tgtgactggt gagtactcaa ccaagtcatt ctgagaatag tgtatgcggc    10560
gaccgagttg ctcttgcccg gcgtcaatac gggataatac cgcgccacat agcagaactt    10620
taaaagtgct catcattgga aaacgttctt cggggcgaaa actctcaagg atcttaccgc    10680
tgttgagatc cagttcgatg taacccactc gtgcacccaa ctgatcttca gcatctttta    10740
ctttcaccag cgtttctggg tgagcaaaaa caggaaggca aaatgccgca aaaagggaa    10800
taagggcgac acggaaatgt tgaatactca tactcttcct ttttcaatat tattgaagca    10860
tttatcaggg ttattgtctc atgagcggat acatatttga atgtatttag aaaaataaac    10920
aaataggggt tccgcgcaca tttccccgaa aagtgccacc tgacgtc                 10967
```

```
<210> SEQ ID NO 6
<211> LENGTH: 7131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pCMV-Myc-ER from position 900 - 2673 - for
      overexpression of Myc tagged ER protein

<400> SEQUENCE: 6
```

| | | | | | |
|---|---|---|---|---|---|
| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gcttggtacc | 900 |
| atggaggagc | agaagctgat | ctcagaggag | gacctgcata | tggccatgga | ggccgaattc | 960 |
| cggatgtcca | tctgtgcctc | ttctcacaag | gattttctc | agctgagacc | tacgcaagac | 1020 |
| atggagatca | aaaactcacc | atcaagcctt | acttcccctg | cttcttataa | ctgtagccag | 1080 |
| tccatcctac | ccttggagca | tggtcccatc | tatatccctt | cctcctatgt | agagagccgt | 1140 |
| cacgaatact | cagccatgac | attctacagt | cctgctgtga | tgaactacag | tgttcccagc | 1200 |
| agcaccggta | acctggaagg | tgggcctgtt | cgccagactg | caagcccaaa | tgtgctatgg | 1260 |
| ccaacttctg | gacacctctc | tcctttagcc | acccactgcc | aatcatcgct | tctctatgca | 1320 |
| gaacctcaaa | agagtccttg | gtgtgaagca | agatcactag | aacacacctt | gcctgtaaac | 1380 |
| agagagaccc | tgaagaggaa | gcttggcggg | agcggttgtg | ccagccctgt | tactagtcca | 1440 |
| agcgccaaga | gggatgctca | cttctgcgcc | gtctgcagtg | attatgcatc | tgggtatcat | 1500 |
| tacggtgtct | ggtcctgtga | aggatgtaag | gccttttta | aaagaagcat | tcaaggacat | 1560 |
| aatgactata | tctgtccagc | cacgaatcag | tgtaccatag | acaagaaccg | gcgtaaaagc | 1620 |
| tgccaggcct | gccgacttcg | caagtgttac | gaagtaggaa | tggtcaagtg | tggatccagg | 1680 |
| agagaaaggt | gtgggtaccg | aatagtacga | agacagagaa | gtgccagcga | gcaggtgcat | 1740 |
| tgcctgaaca | aagccaagag | aaccagtggg | cacacacccc | gggtgaagga | gctactgctg | 1800 |
| aactctctga | gtcccgagca | gctggtgctc | accctgctgg | aagctgagcc | acccaatgtg | 1860 |
| ctagtgagcc | gtcccagcat | gcccttcacc | gaggcctcca | tgatgatgtc | cctcacgaag | 1920 |
| ctggctgaca | aggaactggt | gcacatgatt | ggctgggcca | agaaaatccc | tggctttgtg | 1980 |

```
gagctcagcc tgttggacca agtccgcctc ttggaaagct gctggatgga ggtgctgatg    2040
gtggggctga tgtggcgctc catcgaccac cccggcaagc tcatctttgc tccagacctc    2100
gttctggaca ggtcctcaga agaccctcac tggcacgttg cgcagacgaa gagtgctgtc    2160 ccaaggggatg agggggaagtg cgtggaaggg attctggaaa tctttgacat gctcctggcg    2220
acgacggcac ggttccgtga gttaaaactg cagcacaaag aatatctgtg tgtgaaggcc    2280
atgattctcc tcaactccag tatgtacccc ttggctaccg caagccagga agcagagagt    2340
agccggaagc tgacacacct attgaacgca gtgacagatg ccctggtctg ggtgatttcg    2400
aagagtggaa tctcttccca gcagcagtca gtccgtctgg ccaacctcct gatgcttctt    2460
tctcatgtca ggcacatcag taacaagggc atggaacatc tgctcagcat gaagtgcaaa    2520
aatgtggtcc cggtgtacga cctgctgctg gagatgctga atgctcacac gcttcgaggg    2580
tacaagtcct caatctcggg gtctgagtgc tgctcgacag aggacagtaa gagcaaagag    2640
ggctcccaga acctccagtc acagtgatct agagggccct attctatagt gtcacctaaa    2700
tgctagagct cgctgatcag cctcgactgt gccttctagt tgccagccat ctgttgtttg    2760
cccctccccc gtgccttcct tgaccctgga aggtgccact cccactgtcc tttcctaata    2820
aaatgaggaa attgcatcgc attgtctgag taggtgtcat tctattctgg ggggtggggt    2880
ggggcaggac agcaaggggg aggattggga agacaatagc aggcatgctg gggatgcggt    2940
gggctctatg gcttctgagg cggaaagaac cagctgggc tctaggggt atccccacgc    3000 gccctgtagc ggcgcattaa gcgcggcggg tgtggtggtt acgcgcagcg tgaccgctac    3060
acttgccagc gccctagcgc ccgctccttt cgctttcttc ccttcctttc tcgccacgtt    3120
cgccggcttt ccccgtcaag ctctaaatcg gggcatccct ttagggttcc gatttagtgc    3180
tttacggcac ctcgacccca aaaaacttga ttagggtgat ggttcacgta gtgggccatc    3240
gccctgatag acgttttttc gccctttgac gttggagtcc acgttcttta atagtggact    3300
cttgttccaa actggaacaa cactcaaccc tatctcggtc tattcttttg atttataagg    3360
gattttgggg atttcggcct attggttaaa aaatgagctg atttaacaaa aatttaacgc    3420
gaattaattc tgtggaatgt gtgtcagtta gggtgtggaa agtccccagg ctccccaggc    3480
aggcagaagt atgcaaagca tgcatctcaa ttagtcagca accaggtgtg aaagtcccc    3540 aggctcccca gcaggcagaa gtatgcaaag catgcatctc aattagtcag caaccatagt    3600
cccgccccta actccgccca tcccgcccct aactccgccc agttccgccc attctccgcc    3660
ccatggctga ctaatttttt ttatttatgc agaggccgag gccgcctctg cctctgagct    3720
attccagaag tagtgaggag gcttttttgg aggcctaggc ttttgcaaaa agctcccggg    3780
agcttgtata tccattttcg gatctgatca agagacagga tgaggatcgt ttcgcatgat    3840
tgaacaagat ggattgcacg caggttctcc ggccgcttgg gtggagaggc tattcggcta    3900
tgactgggca caacagacaa tcggctgctc tgatgccgcc gtgttccggc tgtcagcgca    3960
ggggcgcccg gttcttttg tcaagaccga cctgtccggt gccctgaatg aactgcagga    4020
cgaggcagcg cggctatcgt ggctggccac gacgggcgtt ccttgcgcag ctgtgctcga    4080
cgttgtcact gaagcgggaa gggactggct gctattgggc gaagtgccgg ggcaggatct    4140
cctgtcatct caccttgctc ctgccgagaa agtatccatc atggctgatg caatgcggcg    4200
gctgcatacg cttgatccgg ctacctgccc attcgaccac caagcgaaac atcgcatcga    4260
gcgagcacgt actcggatgg aagccggtct tgtcgatcag gatgatctgg acgaagagca    4320
tcaggggctc gcgccagccg aactgttcgc caggctcaag gcgcgcatgc ccgacggcga    4380
```

```
ggatctcgtc gtgacccatg gcgatgcctg cttgccgaat atcatggtgg aaaatggccg    4440
cttttctgga ttcatcgact gtggccggct gggtgtggcg gaccgctatc aggacatagc    4500
gttggctacc cgtgatattg ctgaagagct tggcggcgaa tgggctgacc gcttcctcgt    4560
gctttacggt atcgccgctc ccgattcgca gcgcatcgcc ttctatcgcc ttcttgacga    4620
gttcttctga gcgggactct ggggttcgaa atgaccgacc aagcgacgcc caacctgcca    4680
tcacgagatt tcgattccac cgccgccttc tatgaaaggt tgggcttcgg aatcgttttc    4740
cgggacgccg gctggatgat cctccagcgc ggggatctca tgctggagtt cttcgcccac    4800
cccaacttgt ttattgcagc ttataatggt tacaaataaa gcaatagcat cacaaatttc    4860
acaaataaag cattttttc actgcattct agttgtggtt tgtccaaact catcaatgta    4920
tcttatcatg tctgtatacc gtcgacctct agctagagct tggcgtaatc atggtcatag    4980
ctgtttcctg tgtgaaattg ttatccgctc acaattccac acaacatacg agccggaagc    5040
ataaagtgta aagcctgggg tgcctaatga gtgagctaac tcacattaat tgcgttgcgc    5100
tcactgcccg ctttccagtc gggaaacctg tcgtgccagc tgcattaatg aatcggccaa    5160
cgcgcgggga gaggcggttt gcgtattggg cgctcttccg cttcctcgct cactgactcg    5220
ctgcgctcgg tcgttcggct gcggcgagcg gtatcagctc actcaaaggc ggtaatacgg    5280
ttatccacag aatcagggga taacgcagga aagaacatgt gagcaaaagg ccagcaaaag    5340
gccaggaacc gtaaaaaggc cgcgttgctg gcgtttttcc ataggctccg ccccctgac    5400 gagcatcaca aaaatcgacg ctcaagtcag aggtggcgaa acccgacagg actataaaga    5460
taccaggcgt ttccccctgg aagctccctc gtgcgctctc ctgttccgac cctgccgctt    5520
accggatacc tgtccgcctt tctcccttcg ggaagcgtgg cgctttctca atgctcacgc    5580
tgtaggtatc tcagttcggt gtaggtcgtt cgctccaagc tgggctgtgt gcacgaaccc    5640
cccgttcagc ccgaccgctg cgccttatcc ggtaactatc gtcttgagtc caacccggta    5700
agacacgact tatcgccact ggcagcagcc actggtaaca ggattagcag agcgaggtat    5760
gtaggcggtg ctacagagtt cttgaagtgg tggcctaact acggctacac tagaaggaca    5820
gtatttggta tctgcgctct gctgaagcca gttaccttcg aaaaagagt tggtagctct    5880 tgatccggca aacaaaccac cgctggtagc ggtggttttt ttgtttgcaa gcagcagatt    5940
acgcgcagaa aaaaaggatc tcaagaagat cctttgatct tttctacggg gtctgacgct    6000
cagtggaacg aaaactcacg ttaagggatt ttggtcatga gattatcaaa aaggatcttc    6060
acctagatcc ttttaaatta aaaatgaagt tttaaatcaa tctaaagtat atatgagtaa    6120
acttggtctg acagttacca atgcttaatc agtgaggcac ctatctcagc gatctgtcta    6180
tttcgttcat ccatagttgc ctgactcccc gtcgtgtaga taactacgat acgggagggc    6240
ttaccatctg gccccagtgc tgcaatgata ccgcgagacc cacgctcacc ggctccagat    6300
ttatcagcaa taaaccagcc agccggaagg gccgagcgca gaagtggtcc tgcaacttta    6360
tccgcctcca tccagtctat taattgttgc cgggaagcta gagtaagtag ttcgccagtt    6420
aatagtttgc gcaacgttgt tgccattgct acaggcatcg tggtgtcacg ctcgtcgttt    6480
ggtatggctt cattcagctc cggttcccaa cgatcaaggc gagttacatg atcccccatg    6540
ttgtgcaaaa aagcggttag ctccttcggt cctccgatcg ttgtcagaag taagttggcc    6600
gcagtgttat cactcatggt tatggcagca ctgcataatt ctcttactgt catgccatcc    6660
gtaagatgct tttctgtgac tggtgagtac tcaaccaagt cattctgaga atagtgtatg    6720
```

| cggcgaccga gttgctcttg cccggcgtca atacgggata ataccgcgcc acatagcaga | 6780 |
| actttaaaag tgctcatcat tggaaaacgt tcttcggggc gaaaactctc aaggatctta | 6840 |
| ccgctgttga gatccagttc gatgtaaccc actcgtgcac ccaactgatc ttcagcatct | 6900 |
| tttactttca ccagcgtttc tgggtgagca aaaacaggaa ggcaaaatgc cgcaaaaaag | 6960 |
| ggaataaggg cgacacggaa atgttgaata ctcatactct tcctttttca atattattga | 7020 |
| agcatttatc agggttattg tctcatgagc ggatacatat ttgaatgtat ttagaaaaat | 7080 |
| aaacaaatag gggttccgcg cacatttccc cgaaaagtgc cacctgacgt c | 7131 |

<210> SEQ ID NO 7
<211> LENGTH: 6628
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pCMV-FLAG-NR2E1 from position 922 - 2196- for
      overexpression of FLAG tagged NR2E1 protein

<400> SEQUENCE: 7

| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccatggacta caaggacgac gatgacaagg aattccggat | 960 |
| gagcaagccc gccggatcaa caagccgcat tttagatatc ccttgcaaag tgtgtggtga | 1020 |
| ccgcagctcc gggaagcact acgggtcta cgcttgcgac ggctgctccg gattcttcaa | 1080 |
| gaggagcatt cgaaggaata ggacctatgt ctgcaagtct ggaaaccagg aggatgccc | 1140 |
| cgtagacaag acacacagaa accaatgcag gcgtgtcga ctgaagaagt gtttggaagt | 1200 |
| caacatgaac aaagatgccg tgcagcacga gcgggtcct cggacgtcca ccatccgcaa | 1260 |
| acaggtggct ctctacttcc gtggacacaa ggaagacaat ggggccgctg cgcacttccc | 1320 |
| ctccacggcg ctgccagccc ctgctttctt cacagcggtc acgcagctgg agccgcacgg | 1380 |
| tctggagttg gccgctgtgt ctgccactcc tgaacggcag actctcgtga gcctggctca | 1440 |
| gcccacgccc aagtatcccc atgaagtgaa tgggacccca atgtatctct acgaagtggc | 1500 |
| cactgagtcc gtgtgtgaat cagctgccag gcttctcttt atgagcatca gtgggcaaaa | 1560 |

```
gagtgtgcca gccttttcca ctttgtcttt acaagatcag ctgatgcttt tggaagacgc    1620
gtggagagaa ctgtttgttc taggaatagc acaatgggcc attccggttg atgctaacac    1680
tctactggct gtatctggca tgaatactga acacagac tcccagaagc tgaacaagat      1740
catatctgaa atacaggctt tgcaagaggt ggtggctcgg ttcagacagc tccgattaga    1800
cgccactgaa tttgcctgtc tgaaatgtat tgtcactttc aaagctgttc ctacacacag    1860
tggttctgaa ctgagaagtt tccggaatgc tgccgccatt gccgctctcc aagatgaggc    1920
tcagctaact ctcaacagct acattcatac cagatacccc acccaaccct gccgattcgg    1980
gaaactcctg ttgcttttac cagctttacg gtcaattagc ccatctacca tagaagaagt    2040 gttttttcaaa aaaaccatcg gcaatgtgcc gattacaaga ctactttcag atatgtacaa   2100
atccagtgac atctaagggc tccagtaccc acttttccaa gatggggcag tattagatgg    2160
acatctacat gcaggtcaag cctcaaaagc tctagagggc ccgtttaaac ccgctgatca    2220
gcctcgactg tgccttctag ttgccagcca tctgttgttt gcccctcccc cgtgccttcc    2280
ttgaccctgg aaggtgccac tcccactgtc ctttcctaat aaaatgagga aattgcatcg    2340
cattgtctga gtaggtgtca ttctattctg ggggtgggg tggggcagga cagcaagggg     2400
gaggattggg aagacaatag caggcatgct ggggatgcgg tgggctctat ggcttctgag    2460
gcggaaagaa ccagctgggg ctctaggggg tatccccacg cgccctgtag cggcgcatta    2520
agcgcggcgg gtgtggtggt tacgcgcagc gtgaccgcta cacttgccag cgccctagcg    2580
cccgctcctt tcgctttctt cccttccttt ctcgccacgt tcgccggctt tccccgtcaa    2640
gctctaaatc gggggctccc tttagggttc cgatttagtg ctttacggca cctcgacccc    2700
aaaaaacttg attagggtga tggttcacgt agtgggccat cgccctgata gacggttttt    2760
cgccctttga cgttggagtc cacgttcttt aatagtggac tcttgttcca aactggaaca    2820
acactcaacc ctatctcggt ctattctttt gatttataag ggattttgcc gatttcggcc    2880
tattggttaa aaaatgagct gatttaacaa aaatttaacg cgaattaatt ctgtggaatg    2940
tgtgtcagtt agggtgtgga aagtccccag gctccccagc aggcagaagt atgcaaagca    3000
tgcatctcaa ttagtcagca accaggtgtg gaaagtcccc aggctcccca gcaggcagaa    3060
gtatgcaaag catgcatctc aattagtcag caaccatagt cccgccccta actccgccca    3120
tcccgcccct aactccgccc agttccgccc attctccgcc ccatggctga ctaattttttt  3180 ttatttatgc agaggccgag gccgcctctg cctctgagct attccagaag tagtgaggag    3240
gcttttttgg aggcctaggc ttttgcaaaa agctcccggg agcttgtata tccatttcg     3300 gatctgatca agagacagga tgaggatcgt ttcgcatgat tgaacaagat ggattgcacg    3360
caggttctcc ggccgcttgg gtggagaggc tattcggcta tgactgggca acagacaa     3420 tcggctgctc tgatgccgcc gtgttccggc tgtcagcgca ggggcgcccg gttctttttg    3480
tcaagaccga cctgtccggt gccctgaatg aactgcagga cgaggcagcg cggctatcgt    3540
ggctggccac gacgggcgtt ccttgcgcag ctgtgctcga cgttgtcact gaagcgggaa    3600
gggactggct gctattgggc gaagtgccgg ggcaggatct cctgtcatct caccttgctc    3660
ctgccgagaa agtatccatc atggctgatg caatgcggcg gctgcatacg cttgatccgg    3720
ctacctgccc attcgaccac caagcgaaac atcgcatcga gcgagcacgt actcggatgg    3780
aagccggtct tgtcgatcag gatgatctgg acgaagagca tcaggggctc gcgccagccg    3840
aactgttcgc caggctcaag gcgcgcatgc ccgacggcga ggatctcgtc gtgacccatg    3900
```

```
gcgatgcctg cttgccgaat atcatggtgg aaaatggccg cttttctgga ttcatcgact    3960
gtggccggct gggtgtggcg gaccgctatc aggacatagc gttggctacc cgtgatattg    4020
ctgaagagct tggcggcgaa tgggctgacc gcttcctcgt gctttacggt atcgccgctc    4080
ccgattcgca gcgcatcgcc ttctatcgcc ttcttgacga gttcttctga gcgggactct    4140
ggggttcgaa atgaccgacc aagcgacgcc caacctgcca tcacgagatt tcgattccac    4200
cgccgccttc tatgaaaggt tgggcttcgg aatcgttttc cgggacgccg gctggatgat    4260
cctccagcgc ggggatctca tgctggagtt cttcgcccac cccaacttgt ttattgcagc    4320
ttataatggt tacaaataaa gcaatagcat cacaaatttc acaaataaag cattttttc    4380 actgcattct agttgtggtt tgtccaaact catcaatgta tcttatcatg tctgtatacc    4440
gtcgacctct agctagagct tggcgtaatc atggtcatag ctgtttcctg tgtgaaattg    4500
ttatccgctc acaattccac acaacatacg agccggaagc ataaagtgta aagcctgggg    4560
tgcctaatga gtgagctaac tcacattaat tgcgttgcgc tcactgcccg ctttccagtc    4620
gggaaacctg tcgtgccagc tgcattaatg aatcggccaa cgcgcgggga gaggcggttt    4680
gcgtattggg cgctcttccg cttcctcgct cactgactcg ctgcgctcgg tcgttcggct    4740
gcggcgagcg gtatcagctc actcaaaggc ggtaatacgg ttatccacag aatcaggga    4800 taacgcagga aagaacatgt gagcaaaagg ccagcaaaag gccaggaacc gtaaaaaggc    4860
cgcgttgctg gcgtttttcc ataggctccg ccccccctgac gagcatcaca aaaatcgacg    4920
ctcaagtcag aggtggcgaa acccgacagg actataaaga taccaggcgt ttccccctgg    4980
aagctccctc gtgcgctctc ctgttccgac cctgccgctt accggatacc tgtccgcctt    5040
tctcccttcg ggaagcgtgg cgctttctca tagctcacgc tgtaggtatc tcagttcggt    5100
gtaggtcgtt cgctccaagc tgggctgtgt gcacgaaccc cccgttcagc ccgaccgctg    5160
cgccttatcc ggtaactatc gtcttgagtc aacccggta agacacgact tatcgccact    5220
ggcagcagcc actggtaaca ggattagcag agcgaggtat gtaggcggtg ctacagagtt    5280
cttgaagtgg tggcctaact acggctacac tagaagaaca gtatttggta tctgcgctct    5340
gctgaagcca gttaccttcg gaaaaagagt tggtagctct tgatccggca acaaaccac    5400 cgctggtagc ggtttttttg tttgcaagca gcagattacg cgcagaaaaa aaggatctca    5460
agaagatcct ttgatctttt ctacgggtc tgacgctcag tggaacgaaa actcacgtta    5520
agggattttg gtcatgagat tatcaaaaag gatcttcacc tagatccttt taaattaaaa    5580
atgaagtttt aaatcaatct aaagtatata tgagtaaact tggtctgaca gttaccaatg    5640
cttaatcagt gaggcaccta tctcagcgat ctgtctattt cgttcatcca tagttgcctg    5700
actccccgtc gtgtagataa ctacgatacg ggagggctta ccatctggcc ccagtgctgc    5760
aatgataccg cgagacccac gctcaccggc tccagattta tcagcaataa accagccagc    5820
cggaagggcc gagcgcagaa gtggtcctgc aactttatcc gcctccatcc agtctattaa    5880
ttgttgccgg gaagctagag taagtagttc gccagttaat agtttgcgca acgttgttgc    5940
cattgctaca ggcatcgtgg tgtcacgctc gtcgtttggt atggcttcat tcagctccgg    6000
ttcccaacga tcaaggcgag ttacatgatc ccccatgttg tgcaaaaaag cggttagctc    6060
cttcggtcct ccgatcgttg tcagaagtaa gttggccgca gtgttatcac tcatggttat    6120
ggcagcactg cataattctc ttactgtcat gccatccgta agatgctttt ctgtgactgg    6180
tgagtactca accaagtcat tctgagaata gtgtatgcgg cgaccgagtt gctcttgccc    6240
ggcgtcaata cgggataata ccgcgccaca tagcagaact ttaaaagtgc tcatcattgg    6300
```

```
aaaacgttct tcggggcgaa aactctcaag gatcttaccg ctgttgagat ccagttcgat    6360
gtaacccact cgtgcaccca actgatcttc agcatctttt actttcacca gcgtttctgg    6420
gtgagcaaaa acaggaaggc aaaatgccgc aaaaaggga ataagggcga cacggaaatg     6480
ttgaatactc atactcttcc ttttcaata ttattgaagc atttatcagg gttattgtct     6540
catgagcgga tacatatttg aatgtattta gaaaaataaa caaatagggg ttccgcgcac    6600
atttccccga aaagtgccac ctgacgtc                                        6628

<210> SEQ ID NO 8
<211> LENGTH: 4921
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: ERE-TATA-LUC from position 28 - 144 - to
      measure estrogen receptor mediated activity

<400> SEQUENCE: 8
ggtaccgagc tcttacgcgt gctagcccga gcttaggtca ctgtgacctg agcttaggtc      60
actgtgacct gagcttaggt cactgtgacc tgcatgcctg caggtatacg tcgactctag     120
agggtatata atggatccag atctgcgatc taagtaagct tggcattccg gtactgttgg     180
taaagccacc atggaagacg ccaaaaacat aaagaaaggc ccggcgccat tctatccgct     240
ggaagatgga accgctggag agcaactgca taaggctatg aagagatacg ccctggttcc     300
tggaacaatt gcttttacag atgcacatat cgaggtggac atcacttacg ctgagtactt     360
cgaaatgtcc gttcggttgg cagaagctat gaaacgatat gggctgaata caaatcacag     420
aatcgtcgta tgcagtgaaa actctcttca attctttatg ccggtgttgg gcgcgttatt     480
tatcggagtt gcagttgcgc ccgcgaacga catttataat gaacgtgaat tgctcaacag     540
tatgggcatt tcgcagccta ccgtggtgtt cgttccaaa aaggggttgc aaaaaatttt     600
gaacgtgcaa aaaagctcc caatcatcca aaaaattatt atcatggatt ctaaaacgga     660
ttaccaggga tttcagtcga tgtacacgtt cgtcacatct catctacctc ccggttttaa     720
tgaatacgat tttgtgccag agtccttcga tagggacaag acaattgcac tgatcatgaa     780
ctcctctgga tctactggtc tgcctaaagg tgtcgctctg cctcatagaa ctgcctgcgt     840
gagattctcg catgccagag atcctatttt tggcaatcaa atcattccgg atactgcgat     900
tttaagtgtt gttccattcc atcacggttt tggaatgttt actacactcg gatatttgat     960
atgtggattt cgagtcgtct taatgtatag atttgaagaa gagctgtttc tgaggagcct    1020
tcaggattac aagattcaaa gtgcgctgct ggtgccaacc ctattctcct tcttcgccaa    1080
aagcactctg attgacaaat acgatttatc taatttacac gaaattgctt ctggtggcgc    1140
tcccctctct aaggaagtcg gggaagcggt tgccaagagg ttccatctgc caggtatcag    1200
gcaaggatat gggctcactg agactacatc agctattctg attacacccg agggggatga    1260
taaaccgggc gcggtcggta aagttgttcc attttttgaa gcgaaggttg tggatctgga    1320
taccgggaaa acgctgggcg ttaatcaaag aggcgaactg tgtgtgagag gtcctatgat    1380
tatgtccggt tatgtaaaca atccggaagc gaccaacgcc ttgattgaca aggatggatg    1440
gctacattct ggagacatag cttactggga cgaagacgaa cacttcttca tcgttgaccg    1500
cctgaagtct ctgattaagt acaaaggcta tcaggtggct cccgctgaat tggaatccat    1560
```

-continued

```
cttgctccaa caccccaaca tcttcgacgc aggtgtcgca ggtcttcccg acgatgacgc    1620
cggtgaactt cccgccgccg ttgttgtttt ggagcacgga aagacgatga cggaaaaaga    1680
gatcgtggat tacgtcgcca gtcaagtaac aaccgcgaaa aagttgcgcg gaggagttgt    1740
gtttgtggac gaagtaccga aaggtcttac cggaaaactc gacgcaagaa aaatcagaga    1800
gatcctcata aaggccaaga agggcggaaa gatcgccgtg taattctaga gtcggggcgg    1860
ccggccgctt cgagcagaca tgataagata cattgatgag tttggacaaa ccacaactag    1920
aatgcagtga aaaaaatgct ttatttgtga aatttgtgat gctattgctt tatttgtaac    1980
cattataagc tgcaataaac aagttaacaa caacaattgc attcatttta tgtttcaggt    2040
tcagggggag gtgtgggagg ttttttaaag caagtaaaac ctctacaaat gtggtaaaat    2100
cgataaggat ccgtcgaccg atgcccttga gagccttcaa cccagtcagc tccttccggt    2160
gggcgcgggg catgactatc gtcgccgcac ttatgactgt cttctttatc atgcaactcg    2220
taggacaggt gccggcagcg ctcttccgct tcctcgctca ctgactcgct gcgctcggtc    2280
gttcggctgc ggcgagcggt atcagctcac tcaaaggcgg taatacggtt atccacagaa    2340
tcaggggata acgcaggaaa gaacatgtga gcaaaaggcc agcaaaaggc caggaaccgt    2400
aaaaaggccg cgttgctggc gttttttcat aggctccgcc cccctgacga gcatcacaaa    2460
aatcgacgct caagtcagag gtggcgaaac ccgacaggac tataaagata ccaggcgttt    2520
ccccctggaa gctccctcgt gcgctctcct gttccgaccc tgccgcttac cggatacctg    2580
tccgcctttc tcccttcggg aagcgtggcg ctttctcata gctcacgctg taggtatctc    2640
agttcggtgt aggtcgttcg ctccaagctg ggctgtgtgc acgaaccccc cgttcagccc    2700
gaccgctgcg ccttatccgg taactatcgt cttgagtcca acccggtaag acacgactta    2760
tcgccactgg cagcagccac tggtaacagg attagcagag cgaggtatgt aggcggtgct    2820
acagagttct tgaagtggtg gcctaactac ggctacacta agaacagt atttggtatc    2880
tgcgctctgc tgaagccagt taccttcgga aaaagagttg gtagctcttg atccggcaaa    2940
caaaccaccg ctggtagcgg tggtttttt gtttgcaagc agcagattac gcgcagaaaa    3000
aaaggatctc aagaagatcc tttgatcttt tctacggggt ctgacgctca gtggaacgaa    3060
aactcacgtt aagggatttt ggtcatgaga ttatcaaaaa ggatcttcac ctagatcctt    3120
ttaaattaaa aatgaagttt taaatcaatc taaagtatat atgagtaaac ttggtctgac    3180
agttaccaat gcttaatcag tgaggcacct atctcagcga tctgtctatt tcgttcatcc    3240
atagttgcct gactccccgt cgtgtagata actacgatac gggagggctt accatctggc    3300
cccagtgctg caatgatacc gcgagaccca cgctcaccgg ctccagattt atcagcaata    3360
aaccagccag ccggaagggc cgagcgcaga agtggtcctg caactttatc cgcctccatc    3420
cagtctatta attgttgccg ggaagctaga gtaagtagtt cgccagttaa tagtttgcgc    3480
aacgttgttg ccattgctac aggcatcgtg gtgtcacgct cgtcgtttgg tatggcttca    3540
ttcagctccg gttcccaacg atcaaggcga gttacatgat cccccatgtt gtgcaaaaaa    3600
gcggttagct ccttcggtcc tccgatcgtt gtcagaagta agttggccgc agtgttatca    3660
ctcatggtta tggcagcact gcataattct cttactgtca tgccatccgt aagatgcttt    3720
tctgtgactg gtgagtactc aaccaagtca ttctgagaat agtgtatgcg gcgaccgagt    3780
tgctcttgcc cggcgtcaat acgggataat accgcgccac atagcagaac tttaaaagtg    3840
ctcatcattg gaaaacgttc ttcggggcga aaactctcaa ggatcttacc gctgttgaga    3900
tccagttcga tgtaacccac tcgtgcaccc aactgatctt cagcatcttt tactttcacc    3960
```

-continued

```
agcgtttctg ggtgagcaaa acaggaagg caaaatgccg caaaaaaggg aataagggcg    4020
acacggaaat gttgaatact catactcttc cttttttcaat attattgaag catttatcag  4080
ggttattgtc tcatgagcgg atacatattt gaatgtattt agaaaaataa acaaataggg   4140
gttccgcgca catttccccg aaaagtgcca cctgacgcgc cctgtagcgg cgcattaagc   4200
gcggcgggtg tggtggttac gcgcagcgtg accgctacac ttgccagcgc cctagcgccc   4260
gctcctttcg ctttcttccc ttcctttctc gccacgttcg ccggctttcc ccgtcaagct   4320
ctaaatcggg gctcccttt agggttccga tttagtgctt tacggcacct cgaccccaaa    4380
aaacttgatt agggtgatgg ttcacgtagt gggccatcgc cctgatagac ggttttttcgc 4440
cctttgacgt tggagtccac gttctttaat agtggactct tgttccaaac tggaacaaca   4500
ctcaaccccta tctcggtcta ttcttttgat ttataaggga ttttgccgat ttcggcctat  4560
tggttaaaaa atgagctgat ttaacaaaaa tttaacgcga attttaacaa atattaacg    4620
cttacaattt gccattcgcc attcaggctg cgcaactgtt gggaagggcg atcggtgcgg   4680
gcctcttcgc tattacgcca gcccaagcta ccatgataag taagtaatat taaggtacgg   4740
gaggtacttg gagcggccgc aataaaatat ctttatttc attacatctg tgtgttggtt   4800
ttttgtgtga atcgatagta ctaacatacg ctctccatca aaacaaaacg aaacaaaaca   4860
aactagcaaa ataggctgtc cccagtgcaa gtgcaggtgc cagaacattt ctctatcgat   4920
a                                                                  4921
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer Wdr13E2

<400> SEQUENCE: 9
aacgcctacc gtacaccaac                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer Wdr13E2

<400> SEQUENCE: 10
tgctataggc acgagcactg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer Neo

<400> SEQUENCE: 11
gatcggccat tgaacaagat                                              20

<210> SEQ ID NO 12
<211> LENGTH: 20
<212> TYPE: DNA
<213> ORGANISM: Artificial Sequence

```
<220> FEATURE:
<223> OTHER INFORMATION: Description of Artificial Sequence: Synthetic
      reverse primer Neo

<400> SEQUENCE: 12
atactttctc ggcaggagca                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer p21CHIP

<400> SEQUENCE: 13
caggctggtc ttgaacctgt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer p21CHIP

<400> SEQUENCE: 14
aggcattcaa ggtcgttttg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer CHIP CON

<400> SEQUENCE: 15
tggaactgct tctggtgaac                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer CHIP CON

<400> SEQUENCE: 16
atccgcctct ggcattttgg                                              20

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      forward primer T7

<400> SEQUENCE: 17
gctctagagc agcacagggt gacagaacc                                    29

<210> SEQ ID NO 18
<211> LENGTH: 32
<212> TYPE: DNA
<213> ORGANISM: Artificial Sequence
<220> FEATURE:
```

```
<223> OTHER INFORMATION: Description of Artificial Sequence: Synthetic
      forward primer 2E1

<400> SEQUENCE: 18
ccggaattcc ggatgagcaa gcccgccgga tc                                    32

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      reverse primer 2E1

<400> SEQUENCE: 19
gctctagagc ttttgaggct tgacctgcat                                       30

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer PHIP for N terminal WD domain

<400> SEQUENCE: 20
ctcgtgagca cacactgaca                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer PHIP for N terminal WD domain

<400> SEQUENCE: 21
ttccatatcc caaggactca                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer PHIP for C terminal bromo domain

<400> SEQUENCE: 22
cccaggagat gtccatttgt                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer PHIP for C terminal bromo domain

<400> SEQUENCE: 23
aatccgtcat agcagcaagg                                                  20

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
``` forward primer for ER beta cDNA amplification

<400> SEQUENCE: 24
gcaggaattc atgtccatct gtgcctcttc t                             31

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      reverse primer for ER beta cDNA amplification

<400> SEQUENCE: 25
cagtctagat cactgtgact ggaggttctg                               30

<210> SEQ ID NO 26
<211> LENGTH: 7
<212> TYPE: PRT
<213> ORGANISM: Homo sapiens

<400> SEQUENCE: 26

Cys Leu Asn Lys Leu Leu Leu
1               5

<210> SEQ ID NO 27
<211> LENGTH: 5
<212> TYPE: PRT
<213> ORGANISM: Homo sapiens

<400> SEQUENCE: 27

Leu Asn Lys Leu Leu
1               5

<210> SEQ ID NO 28
<211> LENGTH: 8
<212> TYPE: PRT
<213> ORGANISM: Homo sapiens

<400> SEQUENCE: 28

Ala Tyr Ser Asn Ser Ile Val Arg
1               5

<210> SEQ ID NO 29
<211> LENGTH: 8
<212> TYPE: PRT
<213> ORGANISM: Homo sapiens

<400> SEQUENCE: 29

Ile Trp Ala Ser Glu Asp Gly Arg
1               5

<210> SEQ ID NO 30
<211> LENGTH: 15
<212> TYPE: PRT
<213> ORGANISM: Homo sapiens

<400> SEQUENCE: 30

Leu Val Val His Glu Gly Ser Pro Val Thr Ser Ile Ser Ala Arg
1               5                   10                  15

<210> SEQ ID NO 31
<211> LENGTH: 12
<212> TYPE: PRT
<213> ORGANISM: Homo sapiens

<400> SEQUENCE: 31

Ser Phe Pro Ile Glu Gln Ser Ser His Pro Val Arg
1               5                   10

<210> SEQ ID NO 32
<211> LENGTH: 8
<212> TYPE: PRT
<213> ORGANISM: Homo sapiens

<400> SEQUENCE: 32

Thr Pro Thr Phe Pro Gln Phe Arg
1               5

<210> SEQ ID NO 33
<211> LENGTH: 11
<212> TYPE: PRT
<213> ORGANISM: Homo sapiens

<400> SEQUENCE: 33

Tyr Gly Pro Leu Ser Glu Pro Gly Ser Ala Arg
1               5                   10

<210> SEQ ID NO 34
<211> LENGTH: 14
<212> TYPE: PRT
<213> ORGANISM: Homo sapiens

<400> SEQUENCE: 34

Met Ala Ala Val Trp Gln Gln Val Leu Ala Val Asp Ala Arg
1               5                   10

<210> SEQ ID NO 35
<211> LENGTH: 9
<212> TYPE: PRT
<213> ORGANISM: Homo sapiens

<400> SEQUENCE: 35

Met Glu Asp Phe Glu Asp Asp Pro Arg
1               5

<210> SEQ ID NO 36
<211> LENGTH: 13
<212> TYPE: PRT
<213> ORGANISM: Homo sapiens

<400> SEQUENCE: 36

His Asn Val His Val Met Asn Ile Ser Thr Gly Lys Lys
1               5                   10

<210> SEQ ID NO 37
<211> LENGTH: 7
<212> TYPE: PRT
<213> ORGANISM: Homo sapiens

<400> SEQUENCE: 37

Tyr Leu Tyr Glu Ile Ala Arg
1               5

<210> SEQ ID NO 38
<211> LENGTH: 13
<212> TYPE: PRT
<213> ORGANISM: Homo sapiens

<400> SEQUENCE: 38

Asp Val Phe Leu Gly Met Phe Leu Tyr Glu Tyr Ala Arg
1               5                   10

<210> SEQ ID NO 39
<211> LENGTH: 15
<212> TYPE: PRT
<213> ORGANISM: Homo sapiens

<400> SEQUENCE: 39

Lys Val Pro Gln Val Ser Thr Pro Thr Leu Val Glu Val Ser Arg
1               5                   10                  15

<210> SEQ ID NO 40
<211> LENGTH: 18
<212> TYPE: PRT
<213> ORGANISM: Homo sapiens

<400> SEQUENCE: 40

Thr Val Thr Asn Ala Val Val Thr Val Pro Ala Tyr Phe Asn Asp Ser
1               5                   10                  15

Gln Arg

<210> SEQ ID NO 41
<211> LENGTH: 12
<212> TYPE: PRT
<213> ORGANISM: Homo sapiens

<400> SEQUENCE: 41

Arg Phe Asp Asp Ala Val Val Gln Ser Asp Met Lys
1               5                   10

<210> SEQ ID NO 42
<211> LENGTH: 13
<212> TYPE: PRT
<213> ORGANISM: Homo sapiens

<400> SEQUENCE: 42

Thr Thr Pro Ser Tyr Val Ala Phe Thr Asp Thr Glu Arg
1               5                   10

<210> SEQ ID NO 43
<211> LENGTH: 9
<212> TYPE: PRT
<213> ORGANISM: Homo sapiens

<400> SEQUENCE: 43

Leu Leu Gln Asp Phe Phe Asn Gly Arg
1               5

<210> SEQ ID NO 44
<211> LENGTH: 11
<212> TYPE: PRT
<213> ORGANISM: Homo sapiens

<400> SEQUENCE: 44

Leu Val Asn His Phe Val Glu Glu Phe Lys Arg
1               5                   10

<210> SEQ ID NO 45
<211> LENGTH: 13
<212> TYPE: PRT
<213> ORGANISM: Homo sapiens

<400> SEQUENCE: 45

```
Thr Thr Pro Ser Tyr Val Ala Phe Thr Asp Thr Glu Arg
1               5                   10
```

```
<210> SEQ ID NO 46
<211> LENGTH: 8
<212> TYPE: PRT
<213> ORGANISM: Homo sapiens

<400> SEQUENCE: 46

Ile Trp Ala Thr Asp Asp Gly Arg
1               5
```

```
<210> SEQ ID NO 47
<211> LENGTH: 14
<212> TYPE: PRT
<213> ORGANISM: Homo sapiens

<400> SEQUENCE: 47

Arg Val Val Val Pro Glu Leu Ser Ala Gly Val Ala Ser Arg
1               5                   10
```

```
<210> SEQ ID NO 48
<211> LENGTH: 8
<212> TYPE: PRT
<213> ORGANISM: Homo sapiens

<400> SEQUENCE: 48

Val Thr Met Val Ala Trp Asp Arg
1               5
```

```
<210> SEQ ID NO 49
<211> LENGTH: 10
<212> TYPE: PRT
<213> ORGANISM: Homo sapiens

<400> SEQUENCE: 49

Lys Gln Gln Thr Asn Gln His Asn Tyr Arg
1               5                   10
```

```
<210> SEQ ID NO 50
<211> LENGTH: 10
<212> TYPE: PRT
<213> ORGANISM: Homo sapiens

<400> SEQUENCE: 50

Leu Asp Ala Thr Glu Phe Ala Cys Leu Lys
1               5                   10
```

```
<210> SEQ ID NO 51
<211> LENGTH: 12
<212> TYPE: PRT
<213> ORGANISM: Homo sapiens

<400> SEQUENCE: 51

Thr Val His Pro Asn Ser Pro Gly Ile Pro Tyr Arg
1               5                   10
```

```
<210> SEQ ID NO 52
<211> LENGTH: 9
<212> TYPE: PRT
<213> ORGANISM: Homo sapiens

<400> SEQUENCE: 52

Ser Ala Lys Pro Ser Glu Lys Pro Arg
```

```
<210> SEQ ID NO 53
<211> LENGTH: 8
<212> TYPE: PRT
<213> ORGANISM: Homo sapiens

<400> SEQUENCE: 53

Ser Cys Gln Ala Cys Arg Leu Arg
1               5
```

WDR13 AS A NOVEL BIOMARKER USEFUL FOR TREATING DIABETES AND CANCER

SEQUENCE LISTING

The instant application contains a Sequence Listing which has been submitted electronically in ASCII format and is hereby incorporated by reference in its entirety. Said ASCII copy, created on Feb. 5, 2014, is named KAS-13-1583_SL.txt and is 92,057 bytes in size.

FIELD OF THE DISCLOSURE

The present disclosure relates to a biomarker useful as a drug target for treating diabetes and cancer. Further, inhibiting Wdr13 can treat oligospermia and azoospermia conditions. The present disclosure relates to the creation and characterization of mutant mouse strain lacking Wdr13 gene leading to higher insulin levels and increased islet mass as a result of the enhanced beta cell proliferation, which resulted in age dependent mild obesity phenotype. Further, over expression of this protein leads to up regulation of p21 protein levels and results in cell growth retardation.

BACKGROUND

WD-repeat proteins belong to a large family of structurally related proteins, members of which have diverse functions such as cell cycle regulation, transcription, chromatin organization and protein trafficking [1,2]. These proteins provide a platform for protein-protein interactions. WDR13 protein is a member of this family and localizes to the nucleus [3]. Wdr13 gene is highly conserved in vertebrates and is expressed in most of the tissues [4], the highest level of expression being in pancreas, brain, testis and ovaries. This gene is located on the X-chromosome at locus Xp11.23 and XA1.1 in human and mouse, respectively. In human, X chromosomal deletions including this gene have been associated with mental retardation, obesity and xeroderma [5,6,7,8]. Several WD-repeat proteins have been identified which express in pancreatic beta cells and have roles in beta cell proliferation [9,10].

The beta cell mass is regulated by the balance between neogenesis/proliferation and apoptosis/necrosis. In mice, differentiation of islet precursor and expansion are responsible for beta cell neogenesis until the first week of life [11,12]. Thereafter, expansion of existing beta cells is the main source of newly formed beta cells [13,14]. In pathological conditions there can be alpha to beta cell trans-differentiation [15]. Various cell cycle regulators have been identified which have role in pancreatic beta cell proliferation [16]. Cell cycle progression in pancreatic islet is controlled by cyclins, cyclin dependent kinases (CDKs), cyclin dependent kinase inhibitors and hormones, namely: androgen and estrogen [16,17]. Estrogen enhances pancreatic beta cell mass by protecting them from apoptosis [17,18,19,20].

Pancreatic islet mass, insulin production and body weight are inter-related [12,21]. Insulin levels have been positively correlated with obesity in humans [22] and rodents [23]. Generally, obesity leads to higher demand for insulin production and the same is met by the increase in beta cell mass. Obesity is also a major risk factor for the onset of peripheral insulin resistance [24]. Insulin resistance leads to further higher demand for insulin from beta cells triggering beta cell failure. This leads to beta cell survival defects, insufficient beta cell mass and deterioration of key beta cell function such as glucose stimulated insulin secretion, and ultimately type 2 diabetes. Thus, the mass of insulin producing beta cells changes dynamically according to the metabolic conditions [25,26]. Alternatively, obesity may be a consequence of higher insulin levels [27,28,29] as insulin has stimulatory effect on adipogenesis by increasing the lipid accumulation in adipocytes [30,31,32]. Insulin is also involved in adipocyte survival [33]. Adipose tissue-specific insulin receptor knock-out protects against obesity, emphasizing that insulin signaling to adipocytes is important for development of obesity [31]. Hyper insulin secretion in MOR-1 opioid receptor knockout mice results in more body weight gain with age [29] whereas CHOP knockout mice become obese by increasing insulin secretion although without affecting glucose tolerance [34].

To understand the in vivo role of Wdr13 gene, we have created a mouse strain lacking this gene and show that these mice have higher pancreatic islet mass as a result of higher beta cell proliferation, develop hyperinsulinemia and mild obesity. We have also identified several interacting partners of WDR13 protein and provide evidence that this protein may be working as a repressor of transcription.

DEFINITIONS

WD-Repeat Proteins

The proteins containing structural conserved motif, generally ending with a di-peptide, tryptophan-aspartic acid at c-terminal. However the number of repeats may vary from 4-16 in a given WD-repeat protein.

Chimaeras

Chimera is single organism having two types of genetically distinct cells in its various tissues.

Knockout Mice

A genetically engineered mice in which an endogenous gene on chromosome is inactivated by replacing or disrupting it with a piece of DNA introduced by human intervention.

Obesity

Obesity is a medical condition in which body accumulates excess fat such the excess fat may have a negative health outcome.

Pancreatic Beta Cells

Insulin producing cells in pancreatic islets are known as pancreatic beta cells.

SUMMARY

Accordingly, the present disclosure relates to the use of WDR13 protein as a drug target for curing diabetes and cancer. To address the in vivo function of Wdr13 gene, a member of WD-repeat gene family, we created a mouse strain lacking this gene. In the present study we show that WDR13 is a novel negative regulator of beta cell proliferation. The mutant mice showed significantly higher islet mass, elevated blood insulin levels, age dependent mild obesity and better glucose clearance without any indication of insulin resistance. The enhanced beta cell proliferation in the mutant mice may be due to down regulation of p21, a known cell cycle inhibitor. Consistent with these findings, overexpression of WDR13 in MIN6 cells leads to upregulation of p21 and retardation of cell proliferation. Finally, we show that WDR13 is a novel negative regulator of beta cell proliferation WDR13 acts as a repressor of estrogen receptors mediated transcription both in HDAC-dependent and HDAC-independent manner.

In an embodiment of the present disclosure a biomarker having SEQ ID No: 1 useful for treating diabetes and cancer.

In another embodiment of the present disclosure an expression construct having SEQ ID) NO: 2 useful for targeting WDR13 gene consisting of:
 a. Neomycin with polyA as positive selection marker.
 b. HSV-tk as negative selection marker.
 c. 1.6 kb 5' homology region for 5' recombination.
 d. 4.1 kb 3' homology region for 3' recombination.

In another embodiment of the present disclosure a method of preparing a murine tumor model system comprising:
 a. providing SEQ ID NO: 1 as claimed in claim 1
 b. preparing WDR13 targeting construct
 c. electroporating WDR13 targeting construct as claimed in step b in ES cells,
 d. selecting targeted ES cell clones obtained in step c by southern blot,
 e. generating knockout mice from targeted ES cell clones obtained in step d by known methods,
 f. breeding of knockout mice obtained in step e for getting germ-line transmission by known methods,
 g. obtaining mouse tumor model In another embodiment of the present disclosure a tumor model system useful for studying the progression of cancer at their multistage.

In another embodiment of the present disclosure a method of treating Cancer comprising overexpressing the gene sequence as claimed in claim 1 using adenoviral system (100MOI) in MIN6 cells.

In another embodiment of the present disclosure a method of treating diabetes and enhancing beta cell proliferation by disrupting the biomarker in the beta cells.

In another embodiment of the present disclosure a use of WDR13 as a negative regulator of beta cell proliferation.

In another embodiment of the present disclosure a use of WDR13 as a repressor of estrogen receptors in HDAC dependent (ERα) and in HDAC independent (ERβ) manner.

In another embodiment of the present disclosure a use of WDR13 protein and its downstream targets for modulation of beta cells and testicular spermatogonial cells proliferation in vivo.

In another embodiment of the present disclosure a use of WDR13 protein and its downstream targets in discovery of drugs for modulation of cell proliferation as claimed in 9.

In another embodiment of the present disclosure a use of the WDR13 knockout mice model system in studying the effect of drugs selected from the group comprising of drugs having anti proliferative activity.

An aspect of the present disclosure is to provide a biomarker WDR13 protein having (SEQ ID NO: 1) useful for treating diabetes and cancer.

Another aspect of the present disclosure is to provide WDR13 gene targeting vector (SEQ ID NO: 2)

Another aspect of the present disclosure is to provide a method of treatment of diabetes by enhancing beta cell proliferation.

Another aspect of the present disclosure is to provide a method of treatment of cancer.

Another aspect of the present disclosure is to provide use of WDR13 as a novel negative regulator of beta cell proliferation and its application.

Another aspect of the present disclosure is to provide use of WDR13 as a repressor of estrogen receptors mediated transcription.

Another aspect of the present disclosure is to provide use of WDR13 protein and its downstream targets for modulation of pancreatic beta cells and testicular spermatogonial cells.

Another aspect of the present disclosure is to provide use of WDR13 knockout mice model system in studying the progression of cancer at their multistage.

Another aspect of the present disclosure is to provide use of WDR13 knockout mice model system in studying the effect of drugs selected from the group comprising of having anti proliferative activity.

Another aspect of the present disclosure is to generate a murine tumor model system comprising:
 a. Providing WDR13 gene having SEQ ID NO: 1
 b. Targeting ES with the gene obtained in step a.
 c. Generation of Knockout mice from targeted ES cells
 d. Breeding of knockout mice
 e. Obtaining mouse tumor model Another aspect of the present disclosure is to use this method for preparing a murine tumor model system.

Another aspect of the present disclosure is to generate a mouse tumor model system.

BRIEF DESCRIPTION OF THE DRAWINGS AND TABLES

FIG. 1. Generation of Wdr13 knockout mice. A) Targeting scheme: intron1 (partial) exon2, intron2 and exon3 (partial) of Wdr13 gene are replaced by neomycin resistant marker gene. B) Southern blot analysis showing 9.3 kb EcoRI fragment from the wild type allele and 3.8 kb fragment from the mutant allele using a 700 bp probe from 5' end of the locus. C) Northern blot analysis by Wdr13 cDNA probe showing the absence of Wdr13 transcript in Wdr13−/0 mice (upper panel) and ethidium bromide staining as loading control (lower panel). D) Western blot analysis from testis, pancreas and purified islets using anti-WDR13 rabbit polyclonal antibody (upper panel) showing the absence of WDR13 protein in Wdr13−/0 mice, and anti-beta actin as loading control (lower panel).

Figure 2:
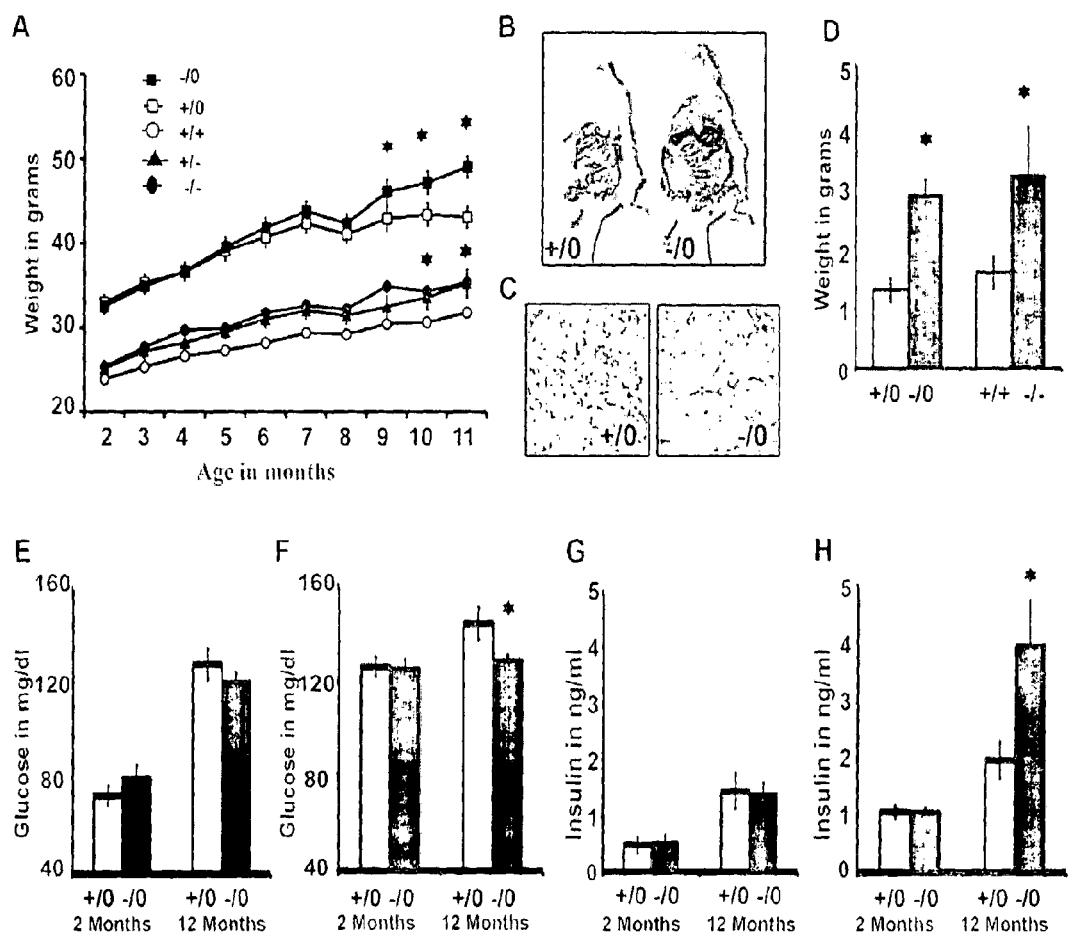

FIG. 2. Body weight, body composition, and glucose and insulin levels of Wdr13 knockout mice fed on normal chow. A) Growth curve of Wdr13+/0 male, Wdr13−/0 male, Wdr13+/+ female, Wdr13+/− female and Wdr13−/− female (n=12) on normal chow. B) Increased adipose tissue mass in Wdr13+/0 mice. C) H&E staining of a section of epididymal fat pad of Wdr13−/0 mouse showing hypertrophy of adipose tissues D) Weight of epididymal fat pad in male and ovarian fat pad in female at 12 months (n=6). E) Sixteen hours fasting glucose level in Wdr13 knockout mice at 2 months and 12 months. F) Random fed glucose level in Wdr13 knockout mice at 2 months and 12 months G) Fasting insulin level in Wdr13 knockout mice at 2 months and 12 months H) Random fed insulin level in Wdr13 knockout mice at 2 months and 12 months.

Figure 3:
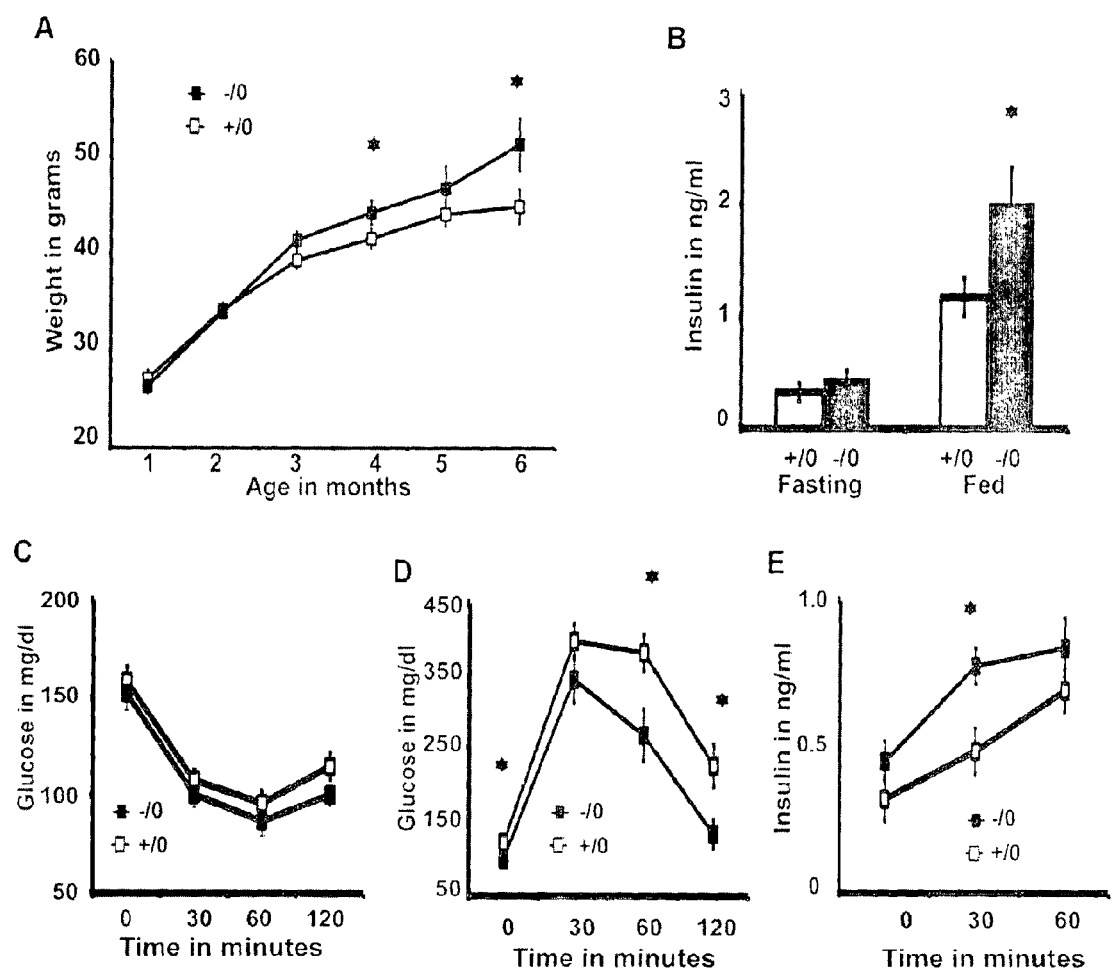

FIG. 3. Body weight and glucose and insulin levels of Wdr13 knockout mice fed on high fat diet. A) Growth curve of Wdr13+/0 male and Wdr13−/0 male on high fat diet (n=10 to 12). B) Fasting and fed insulin level in Wdr13−/0 mice and in their wild type littermates at 6 months. C) Insulin tolerance test at 6 months (n=8). D) Glucose tolerance test at 6 months (n=8). E) In vivo insulin secretion in response to glucose at 6 months (n=4 to 6).

Figure 4:
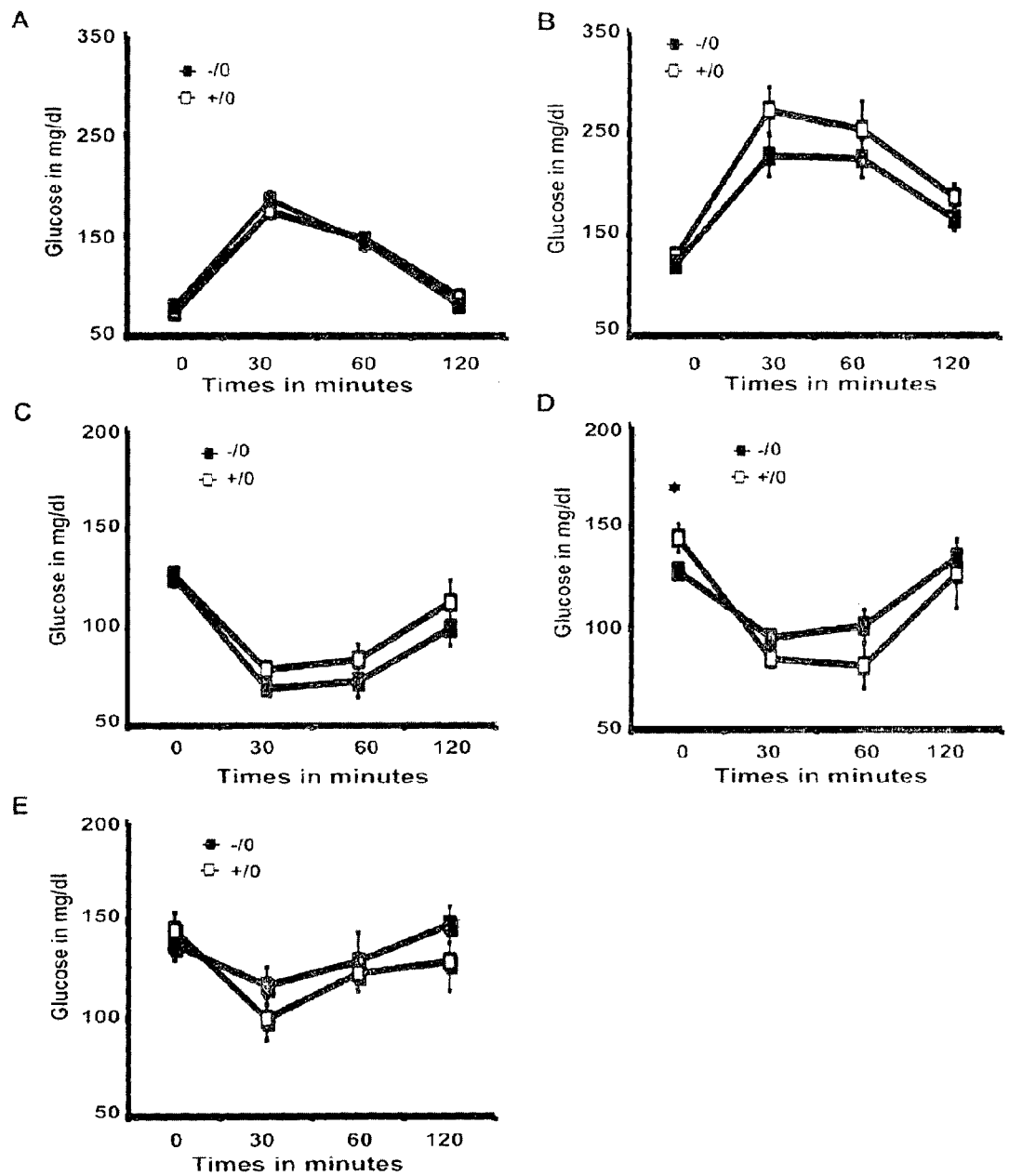

FIG. 4. GTT and ITT of wildtype and Wdr13 knockout mice. A) GTT at age of 2 months on chow. B) GTT at age of 12 months on chow. C) ITT at age of 2 months on chow. D) ITT at age of 12 months on chow. E) ITT at age of 9 months on high fat diet.

Figure 5:
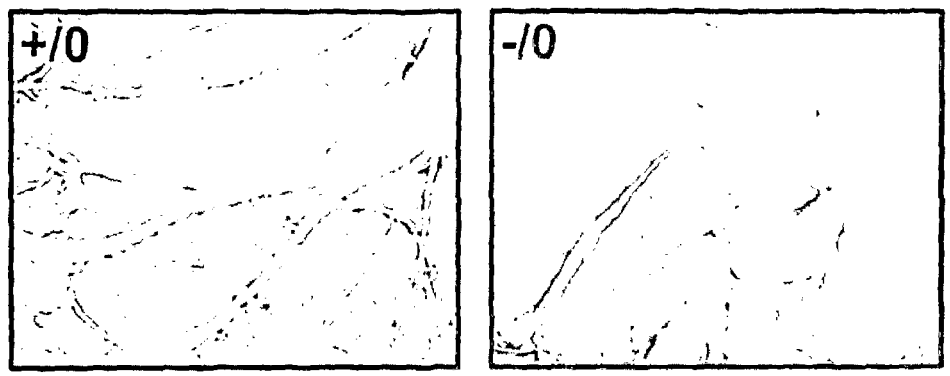
Figure 5:
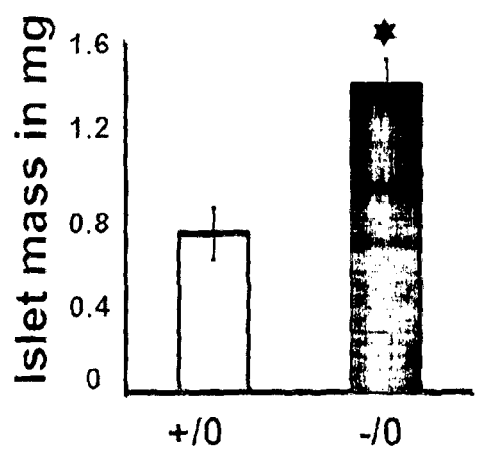
Figure 5:
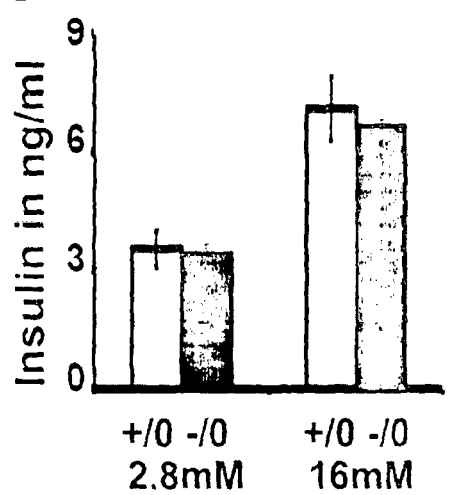

FIG. 5. Histology of pancreatic islets and in-vitro insulin secretion from Wdr13 knockout mice. A) Islet morphology showing increased islet mass by H&E staining. B) Islet mass in mg at 6 months on high fat diet showing increased total islet mass in Wdr13 knockout mice (n=4). C) In vitro insulin secretion from isolated pancreatic islets of the wild type and Wdr13 knockout mice at 2.8 mM and 16 mM glucose concentration.

Figure 6:
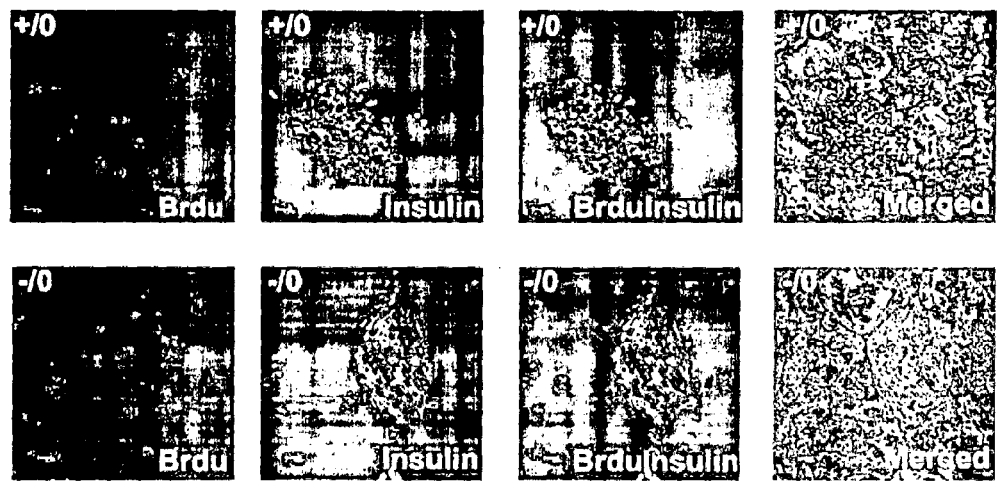
Figure 6:
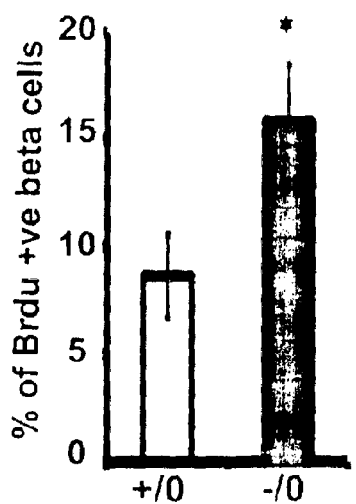
Figure 6:
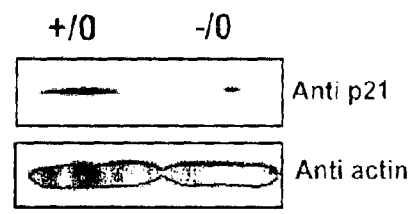

FIG. 6. Pancreatic beta cell proliferation and relative expression of cell cycle regulator p21 in Wdr13 knockout mice. A) Pancreatic beta cells proliferation analysis by BrdU labeling B) Percent of dividing cells in islets by BrdU labeling (n=309-517). C) Expression of the cell cycle inhibitor p21 in pancreatic islets of Wdr13 knockout mice and their wild type litter mates by western blot at 6 months on high fat diet. p21 expression is less in the islets of knockout mice.

Figure 7:
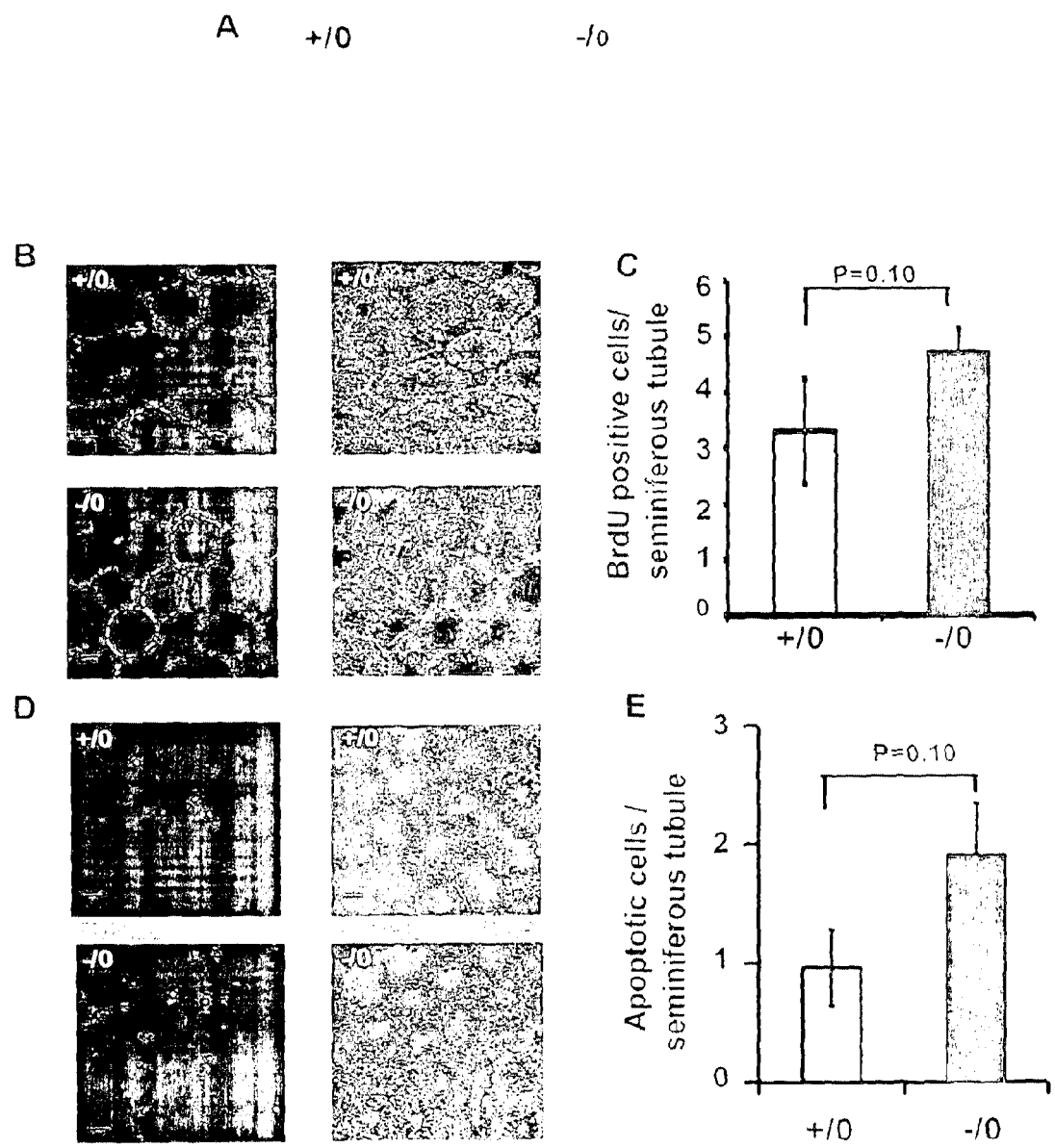

FIG. 7. Spermatogonial cell proliferation and apoptosis in Wdr13−/0 mice. A) Seminiferous tubule morphology by H & E staining. B) Spermatogonial cell proliferation in seminiferous tubule by BrdU labelling. C) BrdU labeling index in seminiferous tubules D) Apoptotic cells in semiferous tubule by TUNEL staining. E) Apoptotic index in seminiferous tubule.

Figure 8:
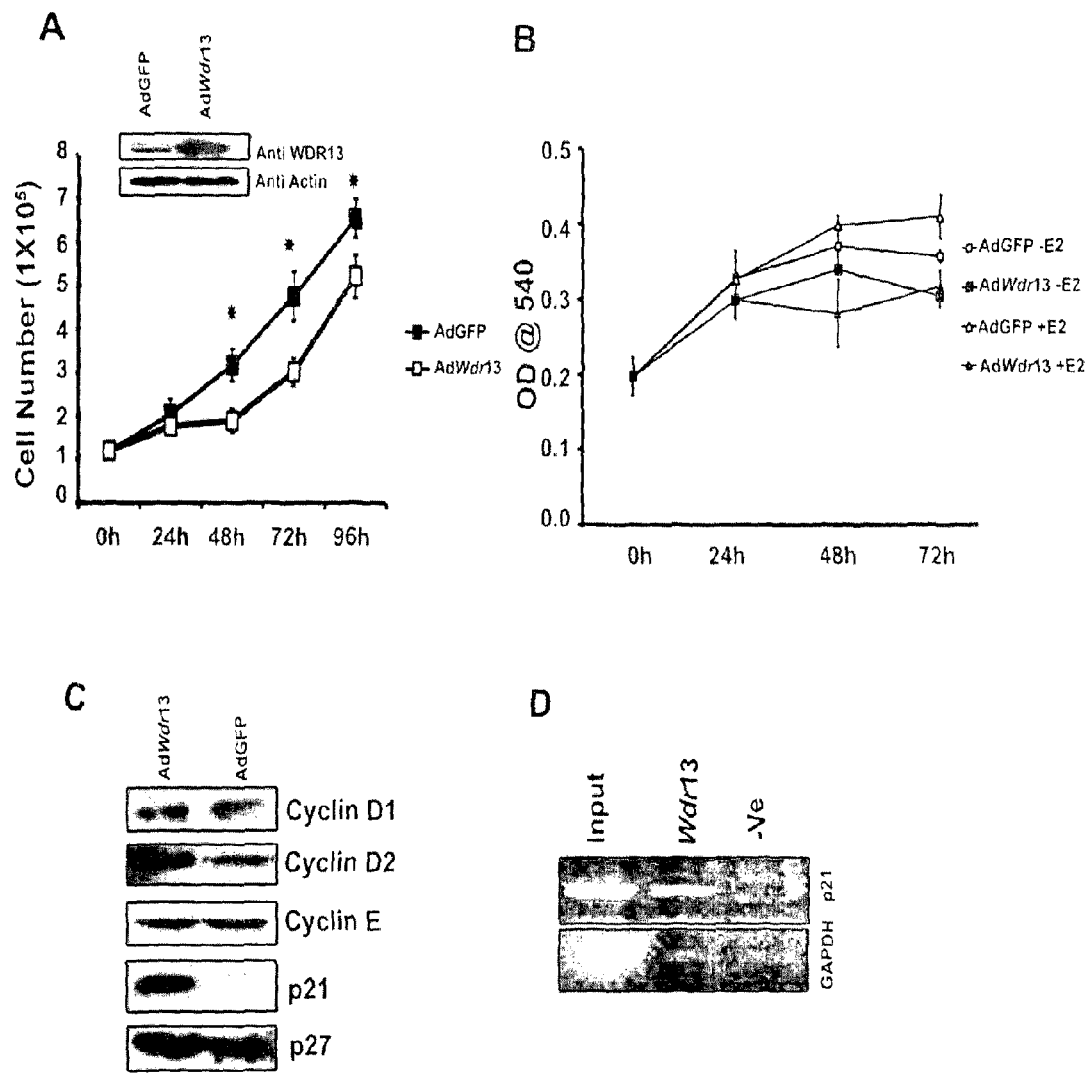

FIG. 8. Overexpression of WDR13 protein in MIN6 and MCF7 cell line and its effect on the rate of cell proliferation. A) Transfection with AdWdr13 and AdGFP viruses shows overexpression of WDR13 protein in MIN6 cells as visualized by immunoblotting using anti WDR13 antibody. Lower panel shows actin as loading control. Overexpression of WDR13 protein results in retardation in the rate of cell proliferation (both by MTT assay and cell counting) after 72 h with 100 MOI. B) Overexpression of WDR13 protein results in retardation in the rate of cell proliferation (MTT assay) after 72 h of transfection with 100 MOI in MCF7 cells which was independent of estradiol. C) Overexpression of WDR13 protein results in accumulation of p21 whereas Cyclin D1, Cyclin D2, Cyclin E1 and p27 levels remain unaffected. D) Occupancy by WDR13 at p21 promoter revealed by chromatin immunoprecipitation using specific primers for p21 and control.

Figure 9:
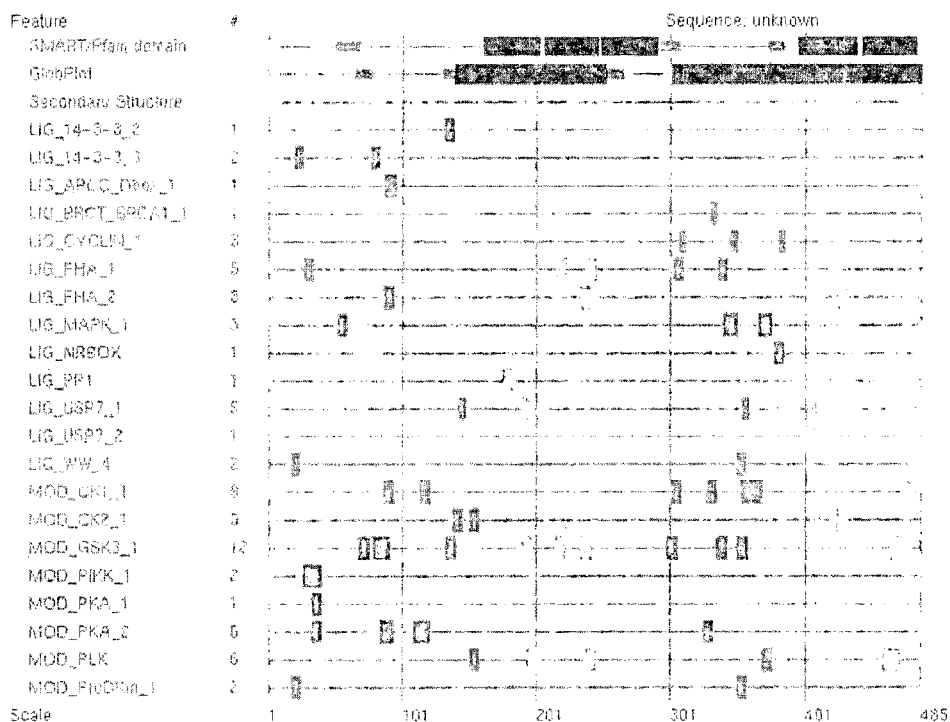

FIG. 9. Presence of LxxLL motif in WDR13 protein. Results of ELM motif search after globular domain filtering, structural filtering and context filtering shows NRBOX [377-383] CLNKLLL (SEQ ID NO: 26) in WDR13 protein.

Figure 10:
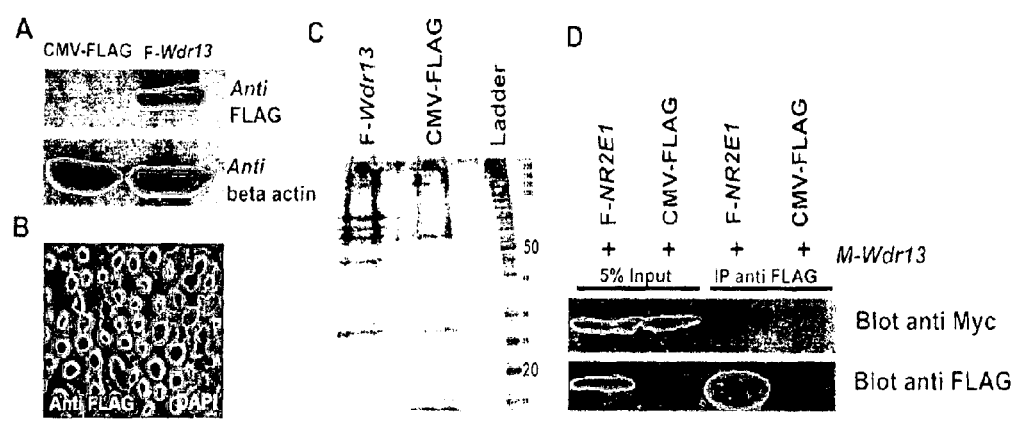

FIG. 10. Identification of proteins interacting with WDR13. A) Western blot using anti FLAG antibody shows overexpression of WDR13 protein in HELA cells upon transfected by pCMV-FLAG control vector and pCMV-FLAG-Wdr13 vector having SEQ ID NO: 3. Lower panel shows beta actin as loading control. B) Immunolocalization of WDR13 protein in HELA cells transfected with pCMV-FLAG-Wdr13 (SEQ ID NO: 3) vector using anti FLAG antibody. C) Silver stained gel of immunoprecipitated proteins using anti FLAG antibody from HELA cells transfected with pCMV-FLAG control and pCMV-FLAG-Wdr13 vectors having SEQ ID NO: 3. D) HEK 293 cell lysate of FLAG-NR2E1 (from the position 922-2196 in SEQ ID NO: 7)/Myc-Wdr13 co-transfected cells immunoprecipitated with anti FLAG antibody followed by immunoblotting with anti Myc antibody does not show interaction of NR2E1 with WDR13 protein. 5% input shows protein expression in cell lysate with FLAG or Myc specific antibody.

Figure 11:
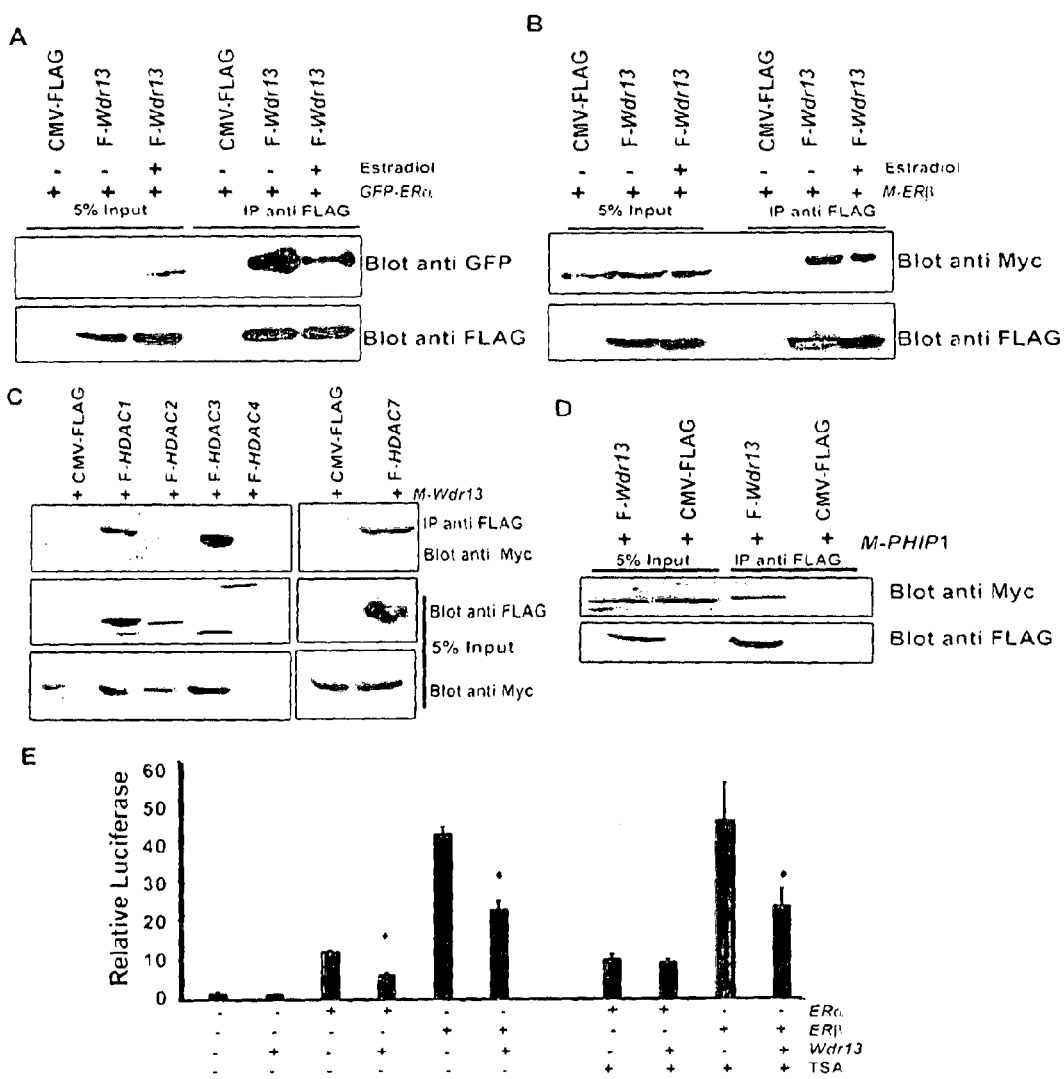

FIG. 11. Interactions of WDR13 with ERs, HDACs and PHIP1 A) HEK 293 cells were co-transfected with FLAG-Wdr13 (from the position 922 to 2443 in SEQ ID NO: 3) and GFP-ERα, grown in the presence or absence of estradiol. The cell lysate was immunoprecipitated with anti FLAG antibody and immunoblotted with anti GFP antibody. 5% input shows protein expression with FLAG or GFP specific antibody. B) HEK 293 cells were co-transfected with FLAG-Wdr13 (from the position 922 to 2443 in SEQ ID NO: 3) and Myc-ERβ I (from the position 900-2673 in SEQ ID NO: 6), grown in the presence or absence of estradiol. The cell lysate was immunoprecipitated with anti FLAG antibody and immunoblotted with anti Myc antibody. 5% input shows protein expression with FLAG or Myc specific antibody. C) HEK 293 cells were co-transfected with Myc-Wdr13 (from the position 900 to 2448 in SEQ ID NO: 4)/various FLAG-HDACs and the cell lysate was immunoprecipitated with anti FLAG antibody and immunoblotted with anti Myc antibody. 5% input shows protein expression with FLAG or Myc specific antibody D) HEK 293 cells were co-transfected with FLAG-Wdr13/Myc-PHIP1 and the cell lysate was immunoprecipitated with anti FLAG antibody and immunoblotted with anti Myc antibody. 5% input shows protein expression with FLAG or Myc specific antibody E) Repression of ERE-TATA-LUC reporter gene by WDR13 in HEK 293 cells in the presence of ERα or ERβ. TSA, a HDACs inhibitor relieves this repressor in case of ERα. Cells were transfected with ERE-TATA-LUC (250 ng), β gal (50 ng), ERα or ERβ (50 ng), Wdr13 (250 ng) in 24-well plates in triplicates and the luciferase and β gal activities were measured 30 h post transfection. The luciferase values were normalized with β gal values.

DETAILED DESCRIPTION

Examples

The following examples are given by way of illustration of the present disclosure and therefore should not be construed to limit the scope of the present disclosure.

Example 1

Generation of Wdr13 Knockout Mice

Wdr13 is a single copy gene located on X-chromosome [4]. The targeting strategy was designed to substitute intron 1 (partial), exon 2, intron 2 and exon 3 (partial) of the endogenous gene with neomycin gene cassette containing polyA (FIG. 1A). To construct the Wdr13 gene targeting vector SEQ ID NO: 1, a 7.1 kb HindIII fragment from this gene including exon1 to exon7 was sub-cloned in pBluescript II KS vector (Stratagene). A 1.35 kb region from this fragment spanning exon 2 and exon 3 (partial) was replaced by XhoI-SalI fragment of pMC1neo Poly A (Stratagene). To further enrich for the targeting events, a negatively selectable HSV-tk gene was placed before the 5' end of homologous sequences from Wdr13 gene. The resulting vector had homologies of 1.6 kb and 4.1 kb at the 5' and 3' ends, respectively. Forty micrograms of linearized targeting vector DNA was electroporated into R1 ES cells. The ES cells were selected with G418 (0.25 mg/ml) and ganciclovir (2 μM). To identify targeted clones, genomic DNA was isolated from ES cells and southern hybridization was performed using a 700 bp EcoRV-BamHI fragment as a probe from the 5' end of this locus (FIG. 1B). One of the targeted clones was injected into 3.5-dpc C57BL/6 blastocysts and the latter were transferred into the uteri of CD1 pseudopregnant females. To obtain germline transmission of the mutant allele, chimaric male mice were mated with CD1 female. Germ line transmission was confirmed by southern analysis. PCR was used for regular screening of mutant mice using a primer pair (Table 1) from the Wdr13 locus and another primer pair from neomycin gene.

TABLE 1

List of primers

| S.No. | Primer name | Primer sequences 5'-3' |
|---|---|---|
| 1 | Wdr13E2F (SEQ ID NO 9) | AACGCCTACCGTACACCAAC |
|  | Wdr13E2R (SEQ ID NO: 10) | TGCTATAGGCACGAGCACTG |
| 2 | NeoF (SEQ ID NO 11) | GATCGGCCATTGAACAAGAT |
|  | NeoR (SEQ ID NO: 12) | ATACTTTCTCGGCAGGAGCA |
| 3 | p21CHIPF (SEQ ID NO: 13) | CAGGCTGGTCTTGAACCTGT |
|  | p21CHIPR (SEQ ID NO: 14) | AGGCATTCAAGGTCGTTTTG |
| 4 | CHIP CON F (SEQ ID NO: 15) | TGGAACTGCTTCTGGTGAAC |
|  | CHIP CON R (SEQ ID NO: 16) | ATCCGCCTCTGGCATTTGG |

To further confirm the targeting of Wdr13 gene northern blot and western blot was performed. Various tissues were snap frozen in liquid nitrogen and stored at −80° C. till further use. Total RNA was isolated using RNeasy Mini Kit (Qiagen). For Northern analysis, RNA was electrophoresed on 1% agarose gel containing 2.2M formaldehyde and blotted on hybond N+ membrane with 50 mM NaOH. Wdr13 cDNA was radio labeled with αdATP using random priming kit. Hybridization was performed overnight at 65° C. in 0.5M phosphate buffer/7% SDS/1 mM EDTA and the membranes were then washed 3× at 65° C. in 40 mM phosphate buffer/1% SDS/1 mM EDTA. The membranes were exposed to X-ray sheets (Fuji films) and developed. Northern blot analysis using Wdr13 cDNA probe revealed the lack of 4 kb and 2 kb transcripts from brain and testis of knockout mice, respectively as compared to the wild type tissues (FIG. 1C). Proteins were extracted from various tissues, separated on 10% SDS-PAGE, blotted on PVDF membranes and western blots were performed. Anti-WDR13 purified antibody (Sigma) was used for visualization of the protein. Western blot using anti WDR13 antibody showed the absence of WDR13 protein in various tissues of the knockout mice (FIG. 1D). These results confirmed that targeting of Wdr13 gene had led to the generation of a null allele.

Example 2

Wdr13 Knockout Mice were Viable and Fertile

Wdr13−/0 male and Wdr13−/− female knockout mice were viable and fertile. Given the comparatively high level of expression of Wdr13 gene in spermatogonia and spermatocytes, and the presence of a different size transcript in testis [4], we analysed the litter size from various matings involving mutant and wild type mice. The genotypes of the parents had no effects on the litter size (Table 2). The sperm number from Wdr13−/0 males (40.6±5.49 million/ml) was similar to that of Wdr13+/0 (37.9±3.05 million/ml).

TABLE 2

Effect of Wdr13 genotype on litter size

| Mating type | Number of matings | Average litter size |
|---|---|---|
| Wdr13−/0 × Wdr13−/+ | 6 | 11.7 |
| Wdr13+/0 × Wdr13−/+ | 7 | 10.6 |
| Wdr13−/0 × Wdr13+/+ | 5 | 10.4 |
| Wdr13−/0 × Wdr13−/− | 6 | 09.8 |

Example 3

Increased Body Weight of Wdr13 Knockout Mice

Mice were housed in temperature, humidity and light/dark cycle (12 hrs 6 am-6 pm) controlled animal rooms. Autoclaved normal diet or high fat diet was fed ad libitum, and feed intake was measured weekly. Mice were weighed fortnightly. Wdr13 deficient mice differentiated in body weight from their wild type littermates around nine months of age when fed normal chow. At 11 months the mutant male and female mice had 13% and 11% higher body weights ($P \leq 0.05$), respectively than their littermates (FIGS. 2A, B). To determine the body composition, mice were dissected and weight of various organs was measured. The weight of epididymal fat pad was 2.5-fold more in Wdr13−/0 mice in comparison to that of wild type, whereas the weight of ovarian fat pad was 2-fold more in Wdr13−/− in comparison to that of the wild type (FIG. 2D). Histological examination of epididymal fat pad revealed adipocyte hypertrophy in Wdr13 knockout mice (FIG. 2C). Adipocyte hypertrophy was also noticed in skin sections of mutant mice. Various organs including, brain, lung, heart, liver, pancreas, spleen and testis of mutant and wild type mice were weighed at 12 months. Mutant mice had significantly higher pancreatic weight. Even the pancreatic weight relative to body weight was more in the mutant mice. There was no difference in the weights of other organs (Table 3).

TABLE 3

Weight (in grams) of various organs from Wdr13 mutant mice and their wild type littermates at 12 months

| Genotype | Tissue | | | | | | | |
|---|---|---|---|---|---|---|---|---|
|  | Pancreas | Testis/Uterus | Liver | Brain | Heart | Kidney | Spleen | Lung |
| Wdr13+/0 (n = 8) | 0.22 ± 0.01 | 0.18 ± 0.01 | 1.67 ± 0.05 | 0.48 ± 0.01 | 0.20 ± 0.01 | 0.58 ± 0.02 | 0.06 ± 0.005 | 0.25 ± 0.01 |
| Wdr13−/0 (n = 8) | 0.30 ± 0.01* | 0.18 ± 0.01 | 1.85 ± 0.10 | 0.49 ± 0.01 | 0.21 ± 0.01 | 0.62 ± 0.02 | 0.08 ± 0.004 | 0.27 ± 0.01 |
| Wdr13+/+ (n = 6) | 0.33 ± 0.02 | 0.87 ± .29 | 1.46 ± 0.07 | 0.49 ± 0.01 | 0.18 ± 0.01 | 0.41 ± 0.01 | 0.11 ± 0.008 | 0.22 ± 0.01 |

TABLE 3-continued

Weight (in grams) of various organs from Wdr13 mutant mice and their wild type littermates at 12 months

| | Tissue | | | | | | | |
|---|---|---|---|---|---|---|---|---|
| Genotype | Pancreas | Testis/Uterus | Liver | Brain | Heart | Kidney | Spleen | Lung |
| Wdr13−/− (n = 6) | 0.41 ± 0.06* | 0.63 ± 0.12 | 1.50 ± 0.07 | 0.52 ± 0.01 | 0.18 ± 0.01 | 0.45 ± 0.03 | 0.12 ± 0.007 | 0.31 ± 0.11 |

*Values are statistically different (P < 0.05)

To understand the effect of diet on the higher body weight of mutant mice, one month old mice were kept on a high fat (60%) diet. Interestingly, Wdr13−/0 weighed significantly more at five months (FIG. 3A) indicating the advancement of mild obesity phenotype of mutant mice.

Example 4

Glucose and Insulin Levels in Wdr13 Knockout Mice

Given the age-dependent obesity phenotype, we measured fasting and random blood glucose levels at different age points in mice fed with normal chow (FIGS. 2E, F). Blood glucose was measured with a glucometer using Sensor Comfort strips (Accu-Check). There was no effect of Wdr13 genotype on fasting glucose levels. Similarly, the random glucose levels at 2 months did not differ between the mutant and wild type mice. However, the mutant mice showed lower random glucose at 12 months on normal chow. In the light of lower random glucose at 12 months, we estimated the serum insulin levels using ELISA kits (Linco Research). The fasting insulin levels were similar in the wild type and mutant mice at both age points (FIG. 2G). While random insulin levels in Wdr13 deficient and wild type mice at 2 months were similar, interestingly, at 12 months mutant mice had 2.13 fold more random insulin level on normal chow (FIG. 2H). Similarly, the mutant mice had 1.6-fold more random insulin levels at six months when fed on a high fat diet (FIG. 3B).

Example 5

Increased Glucose Clearance but Unaltered Insulin Sensitivity in Wdr13 Knockout Mice Given the high level of random insulin levels in Wdr13 deficient mice, we challenged these mice with glucose to determine their glucose clearance at 2 months and 12 months on normal chow, and at 6 months on a high fat diet. To compare glucose clearance and insulin secretion, the mice were kept off-feed for 16 hours, glucose was injected intraperitoneally (2.0 grams glucose/Kg body weight) and blood was collected at 0", 30", 60" and 120" intervals for glucose and insulin measurement. The mutant and wild type mice showed similar glucose clearance (FIGS. 4A, B) at 2 months. At 12 months the mutant mice appeared to have better glucose clearance; however, the difference was not statistically significant. The mutant mice showed consistently better glucose clearance at 6 months on a high fat diet (FIG. 3D). Insulin tolerance was estimated by measuring glucose levels at 0", 30", 60" and 120" intervals after injecting human insulin intraperitoneally (1 U/kg). Wdr13−/0 mice responded to extraneous insulin in a manner similar to the wild type, indicating that insulin sensitivity was not different at 2 months (FIG. 4C) and 12 months (FIG. 4D) on normal chow. Similarly, there was no evidence of insulin resistance in the mutant mice at 6 months (FIG. 3C) and 9 months (FIG. 4E) on a high fat diet, notwithstanding significantly higher random insulin levels in these mice (FIG. 3B).

Example 6

Increased Islet Mass and Beta Cell Proliferation in Wdr13 Knockout Mice

Since Wdr13 deficient mice were hyperinsulinemic and mildly obese, we analyzed the pancreatic histology at 6 months in these mice when fed a high fat diet. For histological examination, tissues were fixed overnight in buffered 4% para formaldehyde, embedded in paraffin and sectioned (4 µm thickness). Sections were mounted on positively charge slides (Fisher Scientific) and were stained with hematoxylin-eosin. Pancreatic and islet areas were measured from pancreatic sections from four mice each of the wildtype and mutant genotypes using Axioskop (Axivision software). Islet mass per pancreas was calculated by multiplying relative islet area with wet mass of pancreas. Interestingly, total islet mass was significantly more in Wdr13 knockout mice at 6 months (FIGS. 5A, B). To understand the increased islet mass, we measured beta cell proliferation by in-situ BrdU labeling. Briefly, one month old mice were kept on a high fat diet for three weeks before infusion of BrdU. To assay beta cell proliferation assay Brdu was given to mice in drinking water (1 mg/ml) for 7 days, pancreatic sections were taken and subjected to immunostaining with anti-insulin (R&D System) and anti-Brdu (BD Biosciences) antibodies. Primary antibody was detected by cy3 or FITC-conjugated antibodies. We observed a 2-fold more proliferation of beta cells in Wdr13 mutant mice as compared to their wild type littermates (FIGS. 6A, B). Similarly there was a trend in more spermatogonial cell proliferation in testis of Wdr13 knockout mice (FIG. 7).

Example 7

Higher Insulin Level in Knockout Mice is Due to the Increased Islet Mass Rather than Insulin Secretion Per Unit Islet Given the better glucose clearance in Wdr13−/0 mice, glucose was injected into 6 month old (on high fat diet) fasting mice and the insulin secretion was monitored at different time points (FIG. 3E). Insulin secretion after 30 minutes of glucose injection was 1.8 fold more in Wdr13−/0 mice. The higher insulin levels in the mutant mice might be the result of the increased islet mass observed by us in these mice (FIGS. 5A, B) or might result from higher insulin secretion per unit beta cell in response to glucose stimulation. To rule out the latter possibility, we isolated islets from 3 month old Wdr13−/0 and their wild type littermates (n=3) as described by Ting Wen et. al. [29]. Briefly, 2 mg/ml collagenase type IV (Invitrogen)

dissolved in Hanks' balanced salt solution (HBSS) was injected in common bile duct and the pancreas were incubated at 37° C. for 30 minutes. After collagenase digestion pancreatic tissue was washed twice with cold HBSS and islets were purified by Ficoll gradient. The purified islets were washed two times with HBSS and transferred to RPMI1640 media supplemented with 10% fetal bovine serum 100 U/ml penicillin, and 50 µg/ml streptomycin for overnight recovery. Next morning, islets were transferred to Krebs-Ringer bicarbonate buffer (111 mM NaCl, 4.8 mM KCl, 2.3 mM $CaCl_2$, 1.2 mM $MgSO_4$, 25 mM $NaHCO_3$) supplemented with 10 mM HEES, 2.8 mM glucose, 0.2% BSA and incubated for 90 minutes at 37° C. with 5% $CO_2$. To measure the insulin secretion in vitro, five equal size islets were plated (in triplicate) in a single well of 96-well plate containing either 250 µl Krebs-Ringer bicarbonate buffer/2.8 mM glucose or 250 µl Krebs-Ringer bicarbonate buffer/16.0 mM glucose and were incubated for 1 h at 37° C. with 5% $CO_2$. The supernatant was collected and stored at −80° C. for insulin measurement. There was no difference in the in vitro insulin secretion between the mutant and wild type islets (FIG. 5C).

Example 8

Overexpression of Wdr13 Gene Results in Cell Growth Retardation

To further understand the role of Wdr13 gene in beta cell proliferation, WDR13 protein was overexpressed in MIN6 cell line using pAd Easy system. To overexpress WDR13 protein, Wdr13 adenovirus constructs were generated. In brief, Wdr13 cDNA was amplified from pCMV-FLAG-Wdr13 (SEQ ID NO: 3) vector using T7 forward primer (SEQ ID NO: 17) and reverse primer 5'GCTCTAGAGCAGCA-CAGGGTGACAGAACC3', digested with PmeI and cloned at EcoRV of pAdTrack-CMV vector. AdGFP or AdWdr13 were generated in HEK293 packaging cell lines according to He et al., [35]. MIN6 cells, HEK293 cells and MCF7 cells were obtained from Cell Repository, National Centre for Cell Science, Pune, India. 10,000 Min6 cells were seeded per well of 24 well plates [36] and were transfected either with AdGFP or AdWdr13 using a titre of 20 or 100 MOI. Cell number was monitored by MTT assay as well as by cell counting at 24 h interval. For western blot analysis, MIN6 cells transfected with 100 MOI with AdGFP or AdWdr13 virus and cells were lysed 48 hour post transfection. MIN6 cells were transfected with AdGFP and AdWdr13 with 100 MOI each in 24 well plates. After 48 hours of transfection, overexpression of Wdr13 was confirmed by western blot (FIG. 8A) using anti WDR13 antibody. Further, MIN6 cells growth curve was prepared by cell counting after overexpression of WDR13 at 100 MOI. At 100 MOI there was significant reduction in cell growth after 48 h post transfection (FIG. 8A). The growth retardation phenotype was further observed in MCF7 cells (FIG. 8B). To understand the growth retardation by overexpression of WDR13 various cell cycle regulators were analyzed by western blotting. The protein levels of cyclin D1, cyclin D2, cyclin E and p27 were unaltered, whereas p21 was highly upregulated after overexpression of WDR13 protein (FIG. 8C). Conversely, in the Wdr13 knockout islets, western blot revealed reduction in p21 levels (FIG. 6C). To understand the nature of p21 regulation by WDR13, promoter occupancy of WDR13 protein was analyzed at p21 promoter. MIN6 cells were transfected with AdGFP and AdWdr13 using 20 MOI and allowed to grow for 48 hours. The cells were crosslinked in 1% formaldehyde for 10 minutes at room temperature and scraped in PBS containing protease inhibitors. Chromatin immunoprecipitation was performed using the chromatin immunoprecipitation (ChIP) Assay Kit, Millipore (Catalogue Number: 17-295) as per the manufacturer's instructions. Briefly, cell lysate was precleaned by incubating in agarose beads for 1 h at room temperature followed by immunoprecipitation with anti-FLAG agarose beads for 3 h. The beads were washed and the genomic DNA fragments were eluted for identification of various promoter regions by PCR. Chromatin immunoprecipitation experiment showed interaction of WDR13 with p21 promoter sequences indicating a direct role of WDR13 in p21 regulation (FIG. 8D).

Example: 9

Identification of Proteins Interacting with WDR13

Eukaryotic Linear Motif resource for functional sites in proteins showed that WDR13 protein contains five WD-repeats and a nuclear receptor box (LNKLL) (SEQ ID NO: 27) at position 378-382 (FIG. 9) along with various casein kinase and GSK3 phosphorylation sites, Generally WD-repeat proteins provide a platform for protein-protein interactions. The presence of LxxLL motif further opens up the possibility that WDR13 may interact with nuclear receptor(s) in a ligand dependent or independent manner. To identify its interacting partners, immunoprecipitation was performed (FIG. 10C) in Hela cells which expresses WDR13. To overexpress FLAG-WDR13 fusion protein, pCMV-FLAG-Wdr13 (SEQ ID NO: 3) plasmid was constructed by cloning Wdr13 cDNA [4] at EcoRI and XbaI sites of pCMV-FLAG plasmid. The overexpression of WDR13 was confirmed by western blot and immunolocalization (FIGS. 10A, B). For immunoprecipitation, pCMV-FLAG-Wdr13 (SEQ ID NO: 3) plasmid and control pEF1GFP plasmid DNAs were transfected into HELA cells (plated in ten 100 mm dishes for each plasmid) using Xfect reagent [37]. After 48 h cells were lysed in lysis buffer (50 mM-Tris.HCl, 150 mM-NaCl, 1 mM-EDTA, 1%-Triton X-100 and Protease inhibitor cocktail) or (50 mM-Tris.HCl, 150 mM-NaCl, 1 mM-EDTA, 1%-Triton X-100, 0.1% SDS and Protease inhibitor cocktail). Cell lysate was centrifuged and pre-cleaned with Protein A. Anti-FLAG agarose beads (Sigma) were added into the pre-cleaned lysate and the lysate were incubated for 4 h at room temperature. The immuno complex was washed 4× with wash buffer (50 mM-Tris.HCl, 150 mM-NaCl, 1 mM-EDTA, 0.5%-Triton X-100 and Protease inhibitor cocktail). Immunocomplex was eluted using FLAG peptide (Sigma) and separated on 12% SDS PAGE. The gel was either stained with 0.1% Coomassie Blue R-250 (in 40% methanol and 10% acetic acid) or blotted on PVDF membrane. The gel was cut into 3 slices of roughly equal size and used for tryptic digestion as per manufacturer's instructions (Sigma). Peptides were separated using a capillary liquid chromatography system (Agilent HPLC 1100 Series, Agilent Technologies), which was attached with a reversed-phase column (ZORBAX 300SB-C18, 75 µm×150 mm, 3.5 µm, Agilent Technologies) that was coupled online to a MALDI target spotter (Probot, LC Packings, Dionex). Mass-spectrometric analysis was performed on a 4800 MALDI TOF/TOF Analyzer (Applied Biosystems). All MS/MS-spectra were searched against the Swissprot 2009 Homo sapiens protein sequence database. MASCOT Server (version 2.0) in combination with the GPS-Explorer™ 3.6 software (Applied Biosystems) was used for identification of proteins. Peptides having peptide ion score ≥15 were considered as significant ID. The list of proteins identified from three independent experiments is summarized in Table 4.

TABLE 4

List of candidate interacting proteins identified by LC-MS/MS after purification of WDR13 immunocomplex

| S.No. | Protein name | Accession No. | Ion score | Peptide sequences (SEQ ID NOS 28-53 and 53, respectively, in order of appearance) |
|---|---|---|---|---|
| 1 | WD repeat-containing protein 13 | sp\|Q9H1XZ4\|WDR13_HUMAN | 48 | AYSNSIVR |
|  |  |  | 41 | IWASEDGR |
|  |  |  | 35 | LVVHEGSPVTSISAR |
|  |  |  | 25 | SFPIEQSSHPVR |
|  |  |  | 28 | TPTFPQFR |
|  |  |  | 20 | YGPLSEPGSAR |
|  |  |  | 20 | MAAVWQQVLAVDAR |
|  |  |  | 13 | MEDFEDDPR |
|  |  |  | 12 | HNVHVMNISTGKK |
| 2 | Serum albumin | sp\|P02768\|ALBU_HUMAN | 36 | YLYEIAR |
|  |  |  | 17 | DVFLGMFLYEYAR |
|  |  |  | 8 | KVPQVSTPTLVEVSR |
| 3 | Heat shock cognate 71 kDa protein | sp\|P11142\|HSP7C_HUMAN | 21 | TVTNAVVTVPAYFNDSQR |
|  |  |  | 18 | RFDDAVVQSDMK |
|  |  |  | 7 | TTPSYVAFTDTER |
| 4 | Heat shock 70 kDa protein 1 | sp\|P08107\|HSP71_HUMAN | 28 | LLQDFFNGR |
|  |  |  | 6 | LVNHFVEEFKR |
|  |  |  | 4 | TTPSYVAFTDTER |
| 5 | PH-interacting protein | sp\|Q8WWQ0\|PHIP_HUMAN | 37 | IWATDDGR |
|  |  |  | 17 | RVVVPELSAGVASR |
|  |  |  | 15 | VTMVAWDR |
|  |  |  | 1 | KQQTNQHNYR |
| 6 | Nuclear receptor subfamily 2 group E member 1 | sp\|Q9Y466\|NR2E1_HUMAN | 25 | LDATEFACLK |
| 7 | Histone deacetylase 7a (HDA7a) | sp\|Q8WU14\|HDAC7_HUMAN | 16 | TVHPNSPGIPYR |
|  |  |  | 10 | SAKPSEKPR |
| 8 | Estrogen receptor beta | sp\|Q92731\|ESR2_HUMAN | 13 | SCQACRLR |
|  |  |  | 11 | SCQACRLR |

Ion score of more than 15 were considered significant.

Example 10

WDR13 Interacts with HDAC 1, 3 and 7

LC-MS/MS results (Table 4) indicated that HDAC7 interacted with WDR13. The interaction of HDAC7 and WDR13 was further validated by co-immunoprecipitation experiment in HEK293 cells (FIG. 11C). The interaction of HDAC7 with WDR13 opened up the possibility that this protein might interact with other HDACs, given the structural and functional similarities of various HDACs [38]. To test this hypothesis, both class I and class II HDACs were individually co-immunoprecipitated with WDR13. To overexpress various HDACs pCMX-hHDAC1-FLAG, pCMX-mHDAC2-FLAG, pCMX-hHDAC3-FLAG, pCMX-hHDAC4-FLAG, and pCMX-mHDAC7-FLAG were used and to overexpress Myc WDR13 fusion protein, pCMV-Myc-Wdr13 (SEQ ID NO: 4) plasmid was constructed by cloning of Wdr13 cDNA at EcoRI and XbaI sites pCMV-Myc vector containing Myc peptide sequence at N-terminal. These experiments showed interaction of WDR13 with HDAC1 and HDAC3 but not with HDAC2 and HDAC4 (FIG. 11C).

Example 11

WDR13 Interacts with Nuclear Receptor ERα, ERβ and PHIP1 but not with NR2E1

The LC-MS/MS results (Table 4) indicated interaction of WDR13 with PHIP1, NR2E1 and ERβ (albeit the ion score was low). The presence of LxxLL motif (FIG. 9) in WDR13 protein encouraged us to further examine the interactions of WDR13 with nuclear receptors, namely; ERα, ERβ, NR2E1 and PHIP1 through co-immunoprecipitation. Various overexpression vectors were constructed. For overexpression of Myc NR2E1 fusion protein, the nuclear receptor 2E1 cDNA (SEQ ID NO: 18 and 19) was cloned from brain using 5'CCGGAATTCCGGATGAGCAAGCCCGCCGOATC3' and 5'GCTCTAGAGCTTTTGAGGCTTGACCTGCAT3' primer pairs and cloned at EcoR1 and Xba1 sites of pCMV-Myc plasmid. For overexpression of Myc PHIP1 (Pleckstrin homology domain interacting protein1) fusion protein the PHIP1 cDNA was amplified from testis using forward primer (SEQ ID NO: 20) 5'CTCGTGAGCACACACTGACA3' and reverse primer (SEQ ID NO: 21) 5'TTCCATATCCCAAG- GACTCA3' for N-terminal WD domain and forward primer (SEQ ID NO: 22) 5'CCCAGGAGATGTCCATTTGT3' and reverse primer (SEQ ID NO: 23) 5'AATCCGTCATAGCAG-CAAGG3' for C-terminal bromodomain. pCMV-Myc-PHIP1 (SEQ ID NO: 24) plasmid was generated by ligating these two fragments. For overexpression of ERα, pCI-nGL1-HEGO plasmid was used [39]. To construct Myc-tagged estrogen receptor beta, the ERβ cDNA (SEQ ID NO: 24 and 25) was amplified from testis using 5'GCAGGAATTCAT-GTCCATCTGTGCCTCTCT3' and 5'CAGTCTAGAT-CACTGTGACTGGAGGTTCTG3' primer pairs and cloned at EcoR1 and Xba1 sites of pCMV-Myc vector. The co-immunoprecipitation experiment showed interaction of ERα and ERβ with WDR13 in a ligand-independent manner (FIGS. 11A, B). Further, the co-immunoprecipitation experiment showed interaction of PHIP1 with WDR13 (FIG. 11D). However, we could not detect any interaction of WDR13 with NR2E1 (FIG. 10D) under our experimental conditions.

Example 12

Repression of ERα and ERβ by WDR13

To understand the functional significance interactions of WDR13 with ERα, ERβ and HDACs, a transient luciferase assay was performed (FIG. 11E). 3XERE-TATA-LUC vector (SEQ ID NO: 8) was constructed by cloning estrogen response element and TATA sequence at SmaI, BglII sites of Pgl3 vector [40]. For estradiol (10 nM) and trichostatin A (50 nM) treatment; HEK293 cells were cultured in phenol red free DMEM, 5% charcoal stripped Serum, 50 μg/ml ampicillin and 50 μg/ml streptomycin. Cells were transfected using lipofectamine 2000 (Invitrogen) as per the manufacturer's instructions. Overexpression of WDR13 resulted in ~2-fold reduction in ERE-driven luciferase activity mediated by ERα or ERβ.

This repression in the reporter activity in the case of ERα was relieved by trichostatin A (TSA), a HDACs inhibitor, whereas there was no effect of TSA on ERβ mediated activity, indicating that WDR13 might be repressing the ERα-mediated transcription through HDACs.

Statistical Analysis

The unpaired two-tailed t test was used for statistical analysis. Microsoft Excel software was used for calculation of P values. A P value <0.05 was considered as significant. Data are presented as mean±SEM.

Ethics Statement

All mice experiments were conducted as per the approval of the Institutional Animal Ethics Committee of the Centre for Cellular and Molecular Biology, Hyderabad, India.

Discussion

In the present study, we have examined the in vivo role of one of the WD-repeat proteins, namely, WDR13 by knocking out this gene in mouse. The mutant mice were viable and fertile without any overt phenotype except that the mice were significantly heavier than their wild type littermates at around nine months and continued to weigh more till the termination of the growth experiment at 12 months when fed on normal chow. This age-dependent higher body weight of the mutant mice advanced to five months when these mice were fed on a high fat diet (FIG. 3A). Anatomical and histological examination revealed that the increased body weights of mutant mice were mainly due to increase in the adipose tissue volume/weight resulting from hypertrophy of adipocytes without any indication of change in adipocyte numbers (FIG. 2C).

The Wdr13 knockout mice were mildly obese and hyperinsulinemic at 12 months on normal diet and at 6 months on a high fat diet, whereas fasting insulin levels were normal. Dynamic changes in the insulin producing pancreatic beta cell mass according to metabolic conditions and positive correlations between body weight, insulin production and islet mass are well documented [12,41]. Various studies have shown that the increase in insulin levels may be a compensatory mechanism to the decreased peripheral insulin sensitivity in response to obesity, ultimately leading to islet failure and to type 2 diabetes [42]. On the other hand, it is also known that higher insulin levels result in higher glucose uptake by adipose tissues, which would in turn alter the lipid metabolism and adipogenesis [43]. Consistent with the latter findings, insulin receptor knockout mice exhibited decreased adipose tissue [44]. In Wdr13 knockout mice, islet mass, insulin levels and glucose-stimulated insulin secretion were more at 6 months on a high fat diet. Notwithstanding higher body weights at 6 month and onwards, these mice were having better glucose clearance, whereas insulin sensitivity was normal as evident from ITT results. We suggest that the body weight gain in Wdr13 knockout mice may be related to the general growth stimulatory effect of higher insulin rather than higher insulin levels being a feedback to the mild obesity observed by us in Wdr13 mice. Insulin stimulates hepatic lipogenesis as well as lipid absorption by adipocytes leading to the increased adipose tissue formation [30]. Moreover, insulin receptor glucose transporter-4 pathway helps to convert glucose to lipid in adipose tissues [43]. In addition to the role of insulin in adipogenesis, insulin secretion has been positively correlated with obesity in humans [22], rodents [23] and non mammalian avian models [45]. We did not observe any difference in insulin sensitivity of the mutant mice from that of wild type littermates at least up to 12 months. As discussed above glucose clearance was better in Wdr13 knockout mice, suggesting that higher insulin secretion in these mice is responsible for low glucose levels observed in the present study. Therefore, given that the insulin sensitivity is normal in the knockout mice, insulin hyper secretion appears less likely to be a compensatory response of the islets as a consequence of mild obesity in these mice. Hyperinsulinemia, accompanied by mild obesity in the Wdr13 knockout mice is reminiscent of MOR1 [29] and chop [28,34] knockout, mice where adiposity is enhanced by higher insulin secretion. The food intake was marginally higher in the Wdr13 knockout mice as compared to the wild type littermates but not statistically significant. Since Wdr13 expresses in hypothalamus and other regions of the brain [7], the possibility of Wdr13 gene having a role in feeding behaviour and or in general metabolism cannot be ruled out in other tissues based upon our present study.

We have earlier reported relatively higher level of expression of Wdr13 in pancreas [3], and the expression of this gene in the pancreatic islets is much more as compared to extremely low levels seen in the acinar cells (FIG. 1D). The Wdr13 knockout mice had more pancreatic islet mass when fed on a high fat diet for five months after weaning at one month. To understand the phenomenon of the increased islet mass, we assayed in vivo beta cell proliferation after one-month old mice were fed high a fat diet for three weeks. The Wdr13 knockout mice had enhanced beta cell proliferation as compared to that in their wild type littermates (FIGS. 6A, B). It may be recalled here that the relative weight of pancreatic mass is significantly more in the adult mutant mice. It appears that the increase in beta cell mass in Wdr13 knockout mice may be due to the enhanced beta cell proliferation. This conclusion is further strengthened by reversal of this phenotype i.e. the growth retardation observed by us in the pancreatic MIN6 cells upon overexpression of Wdr13 gene (FIG. 8).

The lack of difference between in vitro insulin secretion capacities of the wild type and knockout pancreatic islets (FIG. 5C) provides further indirect support to the above conclusion.

Various extrinsic and intrinsic factors responsible for beta cell proliferation have been reported [12,16]. Many positive regulators of beta cells exist which include incretins [46], EGF [47], lactogens and growth hormones [48], HNF-4a [49], calcineurin/NFAT [50], Wnt3a [51] and integrins [52]. Various cell cycle inhibitors (p15, p16, p18, p19, p21, p27 and p57) have been identified, which target either various cyclins or cyclin dependent kinases to inhibit progression at various stages of cell cycle [16]. In the present study, overexpression of WDR13 in pancreatic MIN6 cell line resulted in significantly higher protein level of p21, while cyclin D1, cyclin D2, cyclin E and p27 levels remained unaltered (FIG. 8C). Consistent with these results, knockout of Wdr13 gene resulted in downregulation of p21 in pancreatic islets [53] of the knockout mice (FIG. 6C).

Wdr13 is a member of WD-repeat protein family and these proteins are known to play roles in protein-protein interactions [1]. Our coimmunoprecipitation experiments showed that WDR13 interacts with ERα, ERβ, PHIP1 (pleckstrin homology domain-interacting protein1), HDAC1, HDAC3, and HDAC7. The interactions of WDR13 with PHIP1 (contains bromodomain), ERα, ERβ and histone deacetylases suggest a role(s) of WDR13 in chromatin regulation(s).

PHIP1 contains a WD domain at the N-terminal and a bromodomain at the C-terminal along with bipartite nuclear localization signal, resulting in nuclear localization of this protein [9]. Bromodomain-containing proteins have been reported to perform dual function (co-activator and co-repressor) [54]. The overexpression of PHIP1 has been shown to stimulate cell proliferation by enhancing the cyclin D2 levels in pancreatic MIN6 cell line, whereas knockdown of PHIP1 had a reverse effect [9]. However, these studies had not mentioned the levels of other cyclins and CDK1s. In our experiments the overexpression of Wdr13 gene in pancreatic MIN6 cell line showed upregulation of p21 accompanied by growth retardation. Based upon these observations and the evidence of interaction of WDR13 with PHIP1 we propose that these two proteins may be acting together to modulate beta cell proliferation. Further experiments will be needed to understand the functional significance of this interaction in beta cell proliferation and molecular mechanisms thereof.

We have shown that WDR13 interacts with estrogen receptors (α, β) independent of ligand, and in the ERE luciferase reporter assays WDR13 represses the activity of estrogen receptors HDAC-dependent (ERα) and independent (ERβ) manner (FIG. 11). Interactions of WDR13 with ERα/ERβ may be mediated through LxxLL motif present in WDR13 (FIG. 9), however, this needs to be confirmed by site-directed mutational analysis. Other studies have shown that ERα and ERβ function differentially in various tissues [17,55,56]. Protective roles of estrogen and estrogen receptors have been documented in the case of pancreatic beta cells [17]. Increased islet mass and beta cell proliferation in Wdr13 knockout mice may be resulting from removal of repressive actions of Wdr13 on estrogen receptors at some genomic loci. Down regulation of p21 in Wdr13 knockout islets, upregulation of p21 in pancreatic MIN6 cells as a result of overexpression of Wdr13 gene and evidence for p21 promoter occupancy by WDR13 in CHIP experiments in the present study strongly suggest that the p21 gene is a target of WDR13. Interestingly, regulation of p21 by ERα and HDACi (HDAC inhibitors) has been reported [57,58]. ERα suppresses p21 expression in the presence of estrogen by recruiting corepressors in a p53-dependent manner [59]; the use of HDAC inhibitors results in p21 upregulation and retardation of cell proliferation [57]. However, our reporter assay findings with ERE elements suggest that the interaction of ERα with WDR13 suppresses ERα in a HDAC-dependent manner. One way to reconcile these seemingly contradictory data is to hypothesize that the interaction of WDR13 with ERα at p21 promoter represses ERα in HDAC-independent manner. Such a scenario would explain upregulation of p21 by WDR13 observed in our study (FIG. 8C). Several repressor proteins are known that interact with ERα and may act either in HDAC-dependent or HDAC-independent manner in different tissues/target genes [60]. In this context, it is interesting to note that interaction of WDR13 with ERβ at ERE element resulted in repression in a HDAC-independent manner (FIG. 1E).

It may be recalled that Wdr13 gene is expressed in most of the tissues and it is possible that some of the interactions of this protein with its partners may even be tissue-specific, and consequently the precise mechanism of action may differ in different tissues and/or at different target genes. Extensive CHIP experiments will be necessary to unravel various target genes of WDR13 and the mode of action at these loci in various cell types.

In conclusion, we provide evidence that WDR13 deficiency in mice leads to increased beta cell mass, hyperinsulinemia, better glucose clearance and mild obesity. We suggest that these pancreatic-related phenotypic changes observed by us in the mutant mice are consequences of enhanced beta cell proliferation resulting from downregulation of p21 in the absence of WDR13 in these cells. However, further studies are necessary to reveal any other phenotypic changes associated with this mutation. Further, our data provide evidence that WDR13 interacts with ERα, ERβ, PHIP1 and various HDACs i.e. 1, 3 & 7. The interactions of WDR13 with ERs are estradiol independent and lead to their repression as seen in ERE reporter assays. Interestingly, this repression by WDR13 is both HDAC-dependent (ERα) and HDAC-independent (ERβ). Finally, we propose that given the higher insulin levels, better glucose clearance and the lack of evidence for insulin resistance in Wdr13 knockout mice, this protein may be explored as a potential candidate drug target for ameliorating impaired glucose metabolism in diabetes.

Illustrative Advantages:
1. A novel protein having role in glucose homeostasis and cell proliferation has been identified.
2. A novel repressor of estrogen receptor α and estrogen receptor β has been identified.
3. A novel regulator of estrogen receptor ac that regulates in HDAC dependent manner and estrogen receptor β that regulates it in HDAC independent manner has been identified.
4. A novel regulator of p21 expression has been identified.
5. WDR13 is a novel protein which is useful as a drug target in the treatment of diabetes and cancer.

Although the apparatus and methods have been described in connection with specific forms thereof, it will be appreciated that a wide variety of equivalents may be substituted for the specified elements described herein without departing from the spirit and scope of this disclosure as described in the appended claims.

REFERENCES

1. Smith T F, Gaitatzes C, Saxena K, Neer E J (1999) The W D repeat: a common architecture for diverse functions. Trends Biochem Sci 24: 181-185.

2. Smith T F (2008) Diversity of WD-repeat proteins. Subcell Biochem 48: 20-30.
3. Singh B N, Suresh A, UmaPrasad G, Subramanian S, Sultana M, et al. (2003) A highly conserved human gene encoding a novel member of WD-repeat family of proteins (WDR13). Genomics 81: 315-328.
4. Suresh A, Shah V, Rani D S, Singh B N, Prasad G U, et al. (2005) A mouse gene encoding a novel member of the WD family of proteins is highly conserved and predominantly expressed in the testis (Wdr13). Mol Reprod Dev 72: 299-310.
5. Whibley A C, Plagnol V, Tarpey P S, Abidi F, Fullston T, et al. (2010) Fine-scale survey of X chromosome copy number variants and indels underlying intellectual disability. Am J Hum Genet. 87: 173-188.
6. El-Hattab A, Bournat J, Eng P A Wu J B Walker B A, et al. (2010) Microduplication of Xp11.23p11.3 with effects on cognition, behavior, and craniofacial development. Clin Genet.
7. D'Agata V, Schreurs B G, Pascale A, Zohar O, Cavallaro S (2003) Down regulation of cerebellar memory related gene-1 following classical conditioning. Genes Brain Behav 2: 231-237.
8. Price M, Lang M G Frank A T Goetting-Minesky M P, Patel S P, et al. (2003) Seven cDNAs enriched following hippocampal lesion: possible roles in neuronal responses to injury. Brain Res Mol Brain Res 117: 58-67.
9. Podcheko A, Northcott P, Bikopoulos G, Lee A, Bommareddi S R et al. (2007) Identification of a WD40 repeat-containing isoform of PHIP as a novel regulator of beta-cell growth and survival. Mol Cell Biol 27: 6484-6496.
10. Honore B, Baandrup U, Nielsen S, Vorum H (2002) Endonuclein is a cell cycle regulated WD-repeat protein that is up-regulated in adenocarcinoma of the pancreas. Oncogene 21: 1123-1129.
11. Finegood D T, Scaglia L, Bonner-Weir S (1995) Dynamics of beta-cell mass in the growing rat pancreas. Estimation with a simple mathematical model. Diabetes 44: 249-256.
12. Bouwens L, Rooman I (2005) Regulation of pancreatic beta-cell mass. Physiol Rev 85: 1255-1270.
13. Bonner-Weir S (2000) Perspective: Postnatal pancreatic beta cell growth. Endocrinology 141: 1926-1929.
14. Dor Y, Brown J, Martinez O I, Melton D A (2004) Adult pancreatic beta-cells are formed by self-duplication rather than stem-cell differentiation. Nature 429: 41-46.
15. Thorel F, Nepote V, Avril I, Kohno K, Desgraz R, et al. (2010) Conversion of adult pancreatic alpha-cells to beta-cells after extreme beta-cell loss. Nature 464: 1149-1154.
16. Heit J J, Karnik S K, Kim S K (2006) Intrinsic regulators of pancreatic beta-cell proliferation. Annu Rev Cell Dev Biol 22: 311-338.
17. Mauvais-Jarvis F (2011) Estrogen and androgen receptors: regulators of fuel homeostasis and emerging targets for diabetes and obesity. Trends Endocrinol Metab 22: 24-33.
18. Choi S B, Jang J S, Park S (2005) Estrogen and exercise may enhance beta-cell function and mass via insulin receptor substrate 2 induction in ovariectomized diabetic rats. Endocrinology 146: 4786-4794.
19. Le May C, Chu K, Hu M, Ortega C S, Simpson E R, et al. (2006) Estrogens protect pancreatic beta-cells from apoptosis and prevent insulin-deficient diabetes mellitus in mice. Proc Natl Acad Sci USA 103: 9232-9237.
20. Tiano J P, Delghingaro-Augusto V, Le May C, Liu S, Kaw M K, et al. (2011) Estrogen receptor activation reduces lipid synthesis in pancreatic islets and prevents beta cell failure in rodent models of type 2 diabetes. J Clin Invest 121: 3331-3342.
21. Rhodes C J (2005) Type 2 diabetes—a matter of beta-cell life and death? Science 307: 380-384.
22. Lustig R H, Sen S, Soberman J E, Velasquez-Mieyer P A (2004) Obesity, leptin resistance, and the effects of insulin reduction. Int J Obes Relat Metab Disord 28: 1344-1348.
23. Rohner-Jeanrenaud F, Jeanrenaud B (1985) Involvement of the cholinergic system in insulin and glucagon oversecretion of genetic preobesity. Endocrinology 116: 830-834.
24. Muoio D M Newgard C B (2008) Mechanisms of disease: molecular and metabolic mechanisms of insulin resistance and beta-cell failure in type 2 diabetes. Nat Rev Mol Cell Biol 9: 193-205.
25. Hanley S C, Austin E, Assouline-Thomas B, Kapeluto J, Blaichman J, et al. (2010) {beta}-Cell mass dynamics and islet cell plasticity in human type 2 diabetes. Endocrinology 151: 1462-1472.
26. Ritzel R A, Butler A E, Rizza R A, Veldhuis J D, Butler P C (2006) Relationship between beta-cell mass and fasting blood glucose concentration in humans. Diabetes Care 29: 717-718.
27. Willing A E, Walls E K, Koopmans H S (1990) Insulin infusion stimulates daily food intake and body weight gain in diabetic rats. Physiol Behav 48: 893-898.
28. Song B, Scheuner D, Ron D, Pennathur S, Kaufman R J (2008) Chop deletion reduces oxidative stress, improves beta cell function, and promotes cell survival in multiple mouse models of diabetes. J Clin Invest 118: 3378-3389.
29. Wen T, Peng B, Pintar J E (2009) The MOR-1 opioid receptor regulates glucose homeostasis by modulating insulin secretion. Mol Endocrinol 23: 671-678.
30. Girard J, Perdereau D, Foufelle F, Prip-Buus C, Ferre P (1994) Regulation of lipogenic enzyme gene expression by nutrients and hormones. FASEB J 8: 36-42.
31. Bluher M, Michael M D, Peroni O D, Ueki K, Carter N, et al. (2002) Adipose tissue selective insulin receptor knockout protects against obesity and obesity-related glucose intolerance. Dev Cell 3: 25-38.
32. Bruning J C, Michael M D, Winnay J N, Hayashi T, Horsch D, et al. (1998) A muscle-specific insulin receptor knockout exhibits features of the metabolic syndrome of NIDDM without altering glucose tolerance. Mol Cell 2: 559-569.
33. Loftus T M, Kuhajda F P, Lane M D (1998) Insulin depletion leads to adipose-specific cell death in obese but not lean mice. Proc Natl Acad Sci USA 95: 14168-14172.
34. Ariyama Y, Shimizu H, Satoh T, Tsuchiya T, Okada S, et al. (2007) Chop-deficient mice showed increased adiposity but no glucose intolerance. Obesity (Silver Spring) 15: 1647-1656.
35. He T C, Zhou S, da Costa L T, Yu J, Kinzler K W, et al. (1998) A simplified system tbr generating recombinant adenoviruses. Proc Natl Acad Sci USA 95: 2509-2514.
36. Meng Z X, Nie J, Ling J J, Sun J X, Zhu Y X, et al. (2009) Activation of liver X receptors inhibits pancreatic islet beta cell proliferation through cell cycle arrest. Diabetologia 52: 125-135.
37. Denis G V, McComb M E, Faller D V, Sinha A, Romesser P B, et al. (2006) Identification of transcription complexes that contain the double bromodomain protein Brd2 and chromatin remodeling machines. J Proteome Res 5: 502-511.

38. Gregoretti I V, Lee Y M, Goodson H V (2004) Molecular evolution of the histone deacetylase family: functional implications of phylogenetic analysis. J Mol Biol 338: 17-31.
39. Htun H, Holth L T, Walker D, Davie J R, Hager G L (1999) Direct visualization of the human estrogen receptor alpha reveals a role for ligand in the nuclear distribution of the receptor. Mol Biol Cell 10: 471-486.
40. Legler J, van den Brink C E, Brouwer A, Murk A J, van der Saag P T, et al. (1999) Development of a stably transfected estrogen receptor-mediated luciferase reporter gene assay in the human T47D breast cancer cell line. Toxicol Sci 48: 55-66.
41. Lee Y C, Nielsen J H (2009) Regulation of beta cell replication. Mol Cell Endocrinol 297: 18-27.
42. Gerich J E (1998) The genetic basis of type 2 diabetes mellitus: impaired insulin secretion versus impaired insulin sensitivity. Endocr Rev 19: 491-503.
43. Rosen E D Spiegelman B M (2000) Molecular regulation of adipogenesis. Annu Rev Cell Dev Biol 16: 145-171.
44. Cinti S, Eberbach S, Castellucci M, Accili D (1998) Lack of insulin receptors affects the formation of white adipose tissue in mice. A morphometric and ultrastructural analysis. Diabetologia 41: 171-177.
45. Simon J, Leclercq B (1985) Fat and lean chickens: prefattening period and in vivo sensitivity to insulin, atropine, and propranolol. Am J Physiol 249: R393-401.
46. Xu G, Stoffers D A, Habener J F, Bonner-Weir S (1999) Exendin-4 stimulates both beta-cell replication and neogenesis, resulting in increased beta-cell mass and improved glucose tolerance in diabetic rats. Diabetes 48: 2270-2276.
47. Suarez-Pinzon W L, Yan Y, Power R, Brand S J, Rabinovitch A (2005) Combination therapy with epidermal growth factor and gastrin increases beta-cell mass and reverses hyperglycemia in diabetic NOD mice. Diabetes 54: 2596-2601.
48. Nielsen J H, Galsgaard E D, Moldrup A, Friedrichsen B N, Billestrup N, et al. (2001) Regulation of beta-cell mass by hormones and growth factors. Diabetes 50 Suppl 1: S25-29.
49. Gupta R K, Gao N, Gorski R K, White P, Hardy O T, et al. (2007) Expansion of adult beta-cell mass in response to increased metabolic demand is dependent on HNF-4-alpha. Genes Dev 21: 756-769.
50. Heit J J, Apelqvist A A, Gu X, Winslow M M, Neilson J R, et al. (2006) Calcineurin/NFAT signalling regulates pancreatic beta-cell growth and function. Nature 443: 345-349.
51. Rulifson I C, Karnik S K, Heiser P W, ten Berge D, Chen H, et al. (2007) Wnt signaling regulates pancreatic beta cell proliferation. Proc Natl Acad Sci USA 104: 6247-6252.
52. Nikolova G, Jabs N, Konstantinova I, Domogatskaya A, Tryggvason K, et al. (2006) The vascular basement membrane: a niche for insulin gene expression and Beta cell proliferation. Dev Cell 10: 397-405.
53. Cozar-Castellano I, Weinstock M, Haught M, Velazquez-Garcia S, Sipula D, et al. (2006) Evaluation of beta-cell replication in mice transgenic for hepatocyte growth factor and placental lactogen: comprehensive characterization of the G1/S regulatory proteins reveals unique involvement of p21cip. Diabetes 55: 70-77.
54. Denis G V (2010) Bromodomain coactivators in cancer, obesity, type 2 diabetes, and inflammation. Discov Med 10: 489-499.
55. Barros R P, Gabbi C, Morani A, Warner M, Gustafsson J A (2009) Participation of ERalpha and ERbeta in glucose homeostasis in skeletal muscle and white adipose tissue. Am J Physiol Endocrinol Metab 297: E124-133.
56. Barros R P, Machado U F, Warner M, Gustafsson J A (2006) Muscle GLUT4 regulation by estrogen receptors ERbeta and ERalpha. Proc Natl Acad Sci USA 103: 1605-1608.
57. Margueron R, Licznar A, Lazennec G, Vignon F, Cavailles V (2003) Oestrogen receptor alpha increases p21 (WAF1/CIP1) gene expression and the antiproliferative activity of histone deacetylase inhibitors in human breast cancer cells. J Endocrinol 179: 41-53.
58. Liu W, Konduri S D, Bansal S, Nayak B K, Rajasekaran S A, et al. (2006) Estrogen receptor-alpha binds p53 tumor suppressor protein directly and represses its function. J Biol Chem 281: 9837-9840.
59. Konduri S D, Medisetty R, Liu W, Kaipparettu B A, Srivastava P, et al. (2010) Mechanisms of estrogen receptor antagonism toward p53 and its implications in breast cancer therapeutic response and stem cell regulation. Proc Natl Acad Sci USA 107: 15081-15086.
60. Fernandes I, Bastien Y, Wai T, Nygard K, Lin R, et al. (2003) Ligand-dependent nuclear receptor corepressor LCoR functions by histone deacetylase-dependent and -independent mechanisms. Mol Cell 11: 139-150.

The invention claimed is:

1. An expression construct comprising SEQ ID NO: 2 useful for targeting WDR13 gene represented by SEQ ID NO: 1, wherein SEQ ID NO: 2 comprises:
  a) a nucleic acid sequence encoding Neomycin with polyA as positive selection marker,
  b) a 1.6 kb 5' homology region for 5' recombination, and
  c) a 4.1 kb 3' homology region for 3' recombination, and the expression construct further comprises a nucleic acid sequence encoding HSV-tk as negative selection marker.

2. A method of preparing a murine tumor model system comprising:
  a) preparing the expression construct as claimed in claim 1,
  b) introducing the expression construct as claimed in step a into ES cells by electroporation,
  c) selecting targeted ES cell clones obtained in step b by Southern blot, and
  d) generating knockout mice from the targeted ES cell clones obtained in step c.

* * * * *